United States Patent
Maldonado et al.

(10) Patent No.: US 10,434,088 B2
(45) Date of Patent: Oct. 8, 2019

(54) METHODS RELATED TO ADMINISTERING IMMUNOSUPPRESSANTS AND THERAPEUTIC MACROMOLECULES AT A REDUCED PHARMACODYNAMICALLY EFFECTIVE DOSE

(71) Applicant: Selecta Biosciences, Inc., Watertown, MA (US)

(72) Inventors: Roberto A. Maldonado, Jamaica Plain, MA (US); Takashi Kei Kishimoto, Lexington, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 330 days.

(21) Appl. No.: 14/269,047

(22) Filed: May 2, 2014

(65) Prior Publication Data

US 2014/0328854 A1    Nov. 6, 2014

Related U.S. Application Data

(60) Provisional application No. 61/948,384, filed on Mar. 5, 2014, provisional application No. 61/948,313, filed on Mar. 5, 2014, provisional application No. 61/907,177, filed on Nov. 21, 2013, provisional application No. 61/881,851, filed on Sep. 24, 2013, provisional application No. 61/881,913, filed on Sep. 24, 2013, provisional application No. 61/881,921, filed on Sep. 24, 2013, provisional application No. 61/819,517, filed on May 3, 2013.

(51) Int. Cl.

| | | |
|---|---|---|
| *A61K 39/395* | (2006.01) |
| *A61K 31/436* | (2006.01) |
| *A61K 38/19* | (2006.01) |
| *A61K 38/21* | (2006.01) |
| *A61K 38/37* | (2006.01) |
| *A61K 38/43* | (2006.01) |
| *A61K 45/06* | (2006.01) |
| *A61K 31/192* | (2006.01) |
| *A61K 9/00* | (2006.01) |
| *A61K 9/127* | (2006.01) |
| *A61K 9/51* | (2006.01) |
| *C07K 16/18* | (2006.01) |
| *C07K 16/24* | (2006.01) |
| *C07K 16/40* | (2006.01) |
| *A61K 38/47* | (2006.01) |
| *A61K 47/69* | (2017.01) |
| *A61K 39/00* | (2006.01) |

(52) U.S. Cl.
CPC .......... *A61K 31/436* (2013.01); *A61K 9/0019* (2013.01); *A61K 9/127* (2013.01); *A61K 9/5115* (2013.01); *A61K 9/5153* (2013.01); *A61K 9/5192* (2013.01); *A61K 31/192* (2013.01); *A61K 38/19* (2013.01); *A61K 38/21* (2013.01); *A61K 38/37* (2013.01); *A61K 38/43* (2013.01); *A61K 38/47* (2013.01); *A61K 39/3955* (2013.01); *A61K 39/39533* (2013.01); *A61K 45/06* (2013.01); *A61K 47/6923* (2017.08); *A61K 47/6929* (2017.08); *A61K 47/6935* (2017.08); *A61K 47/6937* (2017.08); *C07K 16/18* (2013.01); *C07K 16/241* (2013.01); *C07K 16/40* (2013.01); *A61K 2039/505* (2013.01); *C12Y 305/01001* (2013.01)

(58) Field of Classification Search
None
See application file for complete search history.

(56) References Cited

U.S. PATENT DOCUMENTS

| | | | |
|---|---|---|---|
| 5,100,669 A | 3/1992 | Hyon et al. |
| 5,543,158 A | 8/1996 | Gref et al. |
| 5,679,347 A | 10/1997 | Porcelli et al. |
| 5,762,904 A | 6/1998 | Okada et al. |
| 5,912,017 A | 6/1999 | Mathiowitz et al. |
| 6,060,082 A | 5/2000 | Chen et al. |
| 6,197,229 B1 | 3/2001 | Ando et al. |
| 6,251,957 B1 | 6/2001 | Wilson et al. |
| 6,306,640 B1 | 10/2001 | Nicolette |
| 6,387,397 B1 | 5/2002 | Chen et al. |
| 6,838,089 B1 | 1/2005 | Carlsson et al. |
| 7,045,508 B2 | 5/2006 | Scaria |
| 8,629,151 B2 | 1/2014 | Zepp et al. |
| 8,652,487 B2 | 2/2014 | Maldonado et al. |
| 8,865,487 B2 | 10/2014 | Kostka et al. |
| 9,005,665 B2 | 4/2015 | Gourapura |
| 9,006,254 B2 | 4/2015 | Zepp et al. |
| 9,017,697 B2 | 4/2015 | Thomas |

(Continued)

FOREIGN PATENT DOCUMENTS

| | | |
|---|---|---|
| CN | 101437491 A | 5/2009 |
| CN | 101646418 A | 2/2010 |

(Continued)

OTHER PUBLICATIONS

U.S. Appl. No. 12/788,260, filed May 26, 2010, Zepp et al.

(Continued)

*Primary Examiner* — Yunsoo Kim

(74) *Attorney, Agent, or Firm* — Wolf, Greenfield & Sacks, P.C.

(57) ABSTRACT

Disclosed are compositions and methods that provide pharmacodynamic effects specific to therapeutic macromolecules. The effects may result from reduced doses of therapeutic macromolecules in combination with immunosuppressant doses. The effects may also be enhanced with such compositions.

22 Claims, 19 Drawing Sheets

(56) References Cited

U.S. PATENT DOCUMENTS

| | | |
|---|---|---|
| 9,066,978 B2 | 6/2015 | Ilyinskii et al. |
| 9,265,815 B2 * | 2/2016 | Fraser .................... A61K 39/00 |
| 9,289,476 B2 * | 3/2016 | Kishimoto ............. A61K 39/00 |
| 9,289,477 B2 * | 3/2016 | Fraser .................... A61K 39/00 |
| 9,295,718 B2 * | 3/2016 | Fraser .................... A61K 39/00 |
| 9,764,031 B2 | 9/2017 | Ilyinskii et al. |
| 9,884,112 B2 | 2/2018 | Zepp et al. |
| 9,987,354 B2 | 6/2018 | Fraser et al. |
| 9,993,548 B2 | 6/2018 | Maldonado et al. |
| 9,994,443 B2 | 6/2018 | Zepp et al. |
| 10,004,802 B2 | 6/2018 | Kishimoto et al. |
| 10,039,822 B2 | 8/2018 | Altreuter et al. |
| 10,046,064 B2 | 8/2018 | Kishimoto |
| 10,071,114 B2 | 9/2018 | Kishimoto |
| 2002/0014242 A1 | 2/2002 | Scaria |
| 2002/0019361 A1 | 2/2002 | Scaria |
| 2002/0086049 A1 | 7/2002 | Bolton et al. |
| 2002/0095135 A1 | 7/2002 | Meeker |
| 2004/0204379 A1 | 1/2004 | Cheng et al. |
| 2004/0038406 A1 | 2/2004 | Unger et al. |
| 2004/0043483 A1 | 3/2004 | Qian et al. |
| 2006/0002852 A1 | 1/2006 | Saltzman et al. |
| 2006/0002971 A1 | 1/2006 | Saltzman et al. |
| 2006/0147432 A1 | 7/2006 | Moore et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |
| 2006/0251711 A1 | 11/2006 | Konduri et al. |
| 2006/0269540 A1 | 11/2006 | Robert et al. |
| 2007/0110685 A1 | 5/2007 | Auspitz et al. |
| 2007/0254897 A1 | 11/2007 | Gjorstrup |
| 2008/0031899 A1 | 2/2008 | Reddy et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0074828 A1 | 3/2009 | Alexis et al. |
| 2009/0082260 A1 | 3/2009 | Lamb et al. |
| 2009/0155292 A1 | 6/2009 | Santamaria et al. |
| 2009/0226525 A1 | 9/2009 | de los Rios et al. |
| 2010/0008932 A1 | 1/2010 | Bensussan et al. |
| 2010/0028450 A1 | 2/2010 | Vasu et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0068286 A1 | 3/2010 | Troiano et al. |
| 2010/0069426 A1 | 3/2010 | Zale et al. |
| 2010/0080816 A1 | 4/2010 | Hadeiba et al. |
| 2010/0112077 A1 | 5/2010 | Desai et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0196401 A1 | 8/2010 | Scaria |
| 2010/0233197 A1 | 9/2010 | Wakatsuki Pedersen et al. |
| 2010/0233251 A1 * | 9/2010 | Von Andrian ......... A61K 39/00 424/450 |
| 2010/0273220 A1 | 10/2010 | Yanik et al. |
| 2010/0303850 A1 | 12/2010 | Lipford et al. |
| 2011/0004148 A1 | 1/2011 | Ishii |
| 2011/0020388 A1 | 1/2011 | Zepp et al. |
| 2011/0027217 A1 | 2/2011 | Zepp et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0166172 A1 | 7/2011 | Nan et al. |
| 2011/0171248 A1 | 7/2011 | Pittet et al. |
| 2011/0223201 A1 | 9/2011 | Lipford et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0039989 A1 | 2/2012 | Hubbell et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0076831 A1 | 3/2012 | Miller et al. |
| 2012/0077860 A1 | 3/2012 | Garcia |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 * | 11/2012 | Fraser .................... A61K 39/00 424/193.1 |
| 2012/0276155 A1 * | 11/2012 | Kishimoto ............. A61K 39/00 424/400 |
| 2012/0276156 A1 * | 11/2012 | Fraser .................... A61K 39/00 424/400 |
| 2012/0276157 A1 * | 11/2012 | Fraser .................... A61K 39/00 424/400 |
| 2012/0276158 A1 * | 11/2012 | Fraser .................... A61K 39/00 424/400 |
| 2012/0276159 A1 * | 11/2012 | Fraser .................... A61K 39/00 424/400 |
| 2012/0276160 A1 | 11/2012 | Maldonado et al. |
| 2012/0294888 A1 * | 11/2012 | Kishimoto ............. A61K 39/00 424/196.11 |
| 2012/0301498 A1 * | 11/2012 | Altreuter ................ A61K 39/00 424/193.1 |
| 2012/0301510 A1 * | 11/2012 | Kishimoto ............. A61K 39/00 424/400 |
| 2012/0308563 A1 | 12/2012 | Arya |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0336245 A1 | 11/2014 | Mingozzi et al. |
| 2014/0356361 A1 | 12/2014 | Maldonado et al. |
| 2015/0024007 A1 | 1/2015 | Hesse et al. |
| 2015/0111955 A1 | 4/2015 | High et al. |
| 2015/0320728 A1 * | 11/2015 | Fraser .................... A61K 39/00 424/185.1 |
| 2015/0320856 A1 * | 11/2015 | Altreuter ................ A61K 39/00 424/501 |
| 2015/0320870 A1 | 11/2015 | Maldonado |
| 2015/0320884 A1 * | 11/2015 | Fraser .................... A61K 39/00 424/193.1 |
| 2015/0328300 A1 | 11/2015 | Zepp et al. |
| 2015/0328309 A1 | 11/2015 | Ilyinskii et al. |

(56) References Cited

U.S. PATENT DOCUMENTS

| | | | |
|---|---|---|---|
| 2015/0328333 A1* | 11/2015 | Fraser | A61K 39/00 424/193.1 |
| 2015/0335762 A1* | 11/2015 | Fraser | A61K 39/00 424/193.1 |
| 2015/0359865 A1 | 12/2015 | Kishimoto | |
| 2015/0374815 A1 | 12/2015 | Kishimoto et al. | |
| 2016/0022650 A1* | 1/2016 | Fraser | A61K 39/00 424/185.1 |
| 2016/0030554 A1* | 2/2016 | Kishimoto | A61K 39/00 424/193.1 |
| 2016/0030555 A1* | 2/2016 | Kishimoto | A61K 39/00 424/185.1 |
| 2016/0067228 A1 | 3/2016 | Kishimoto et al. | |
| 2016/0074372 A1 | 3/2016 | Kishimoto | |
| 2016/0074427 A1 | 3/2016 | Kishimoto | |
| 2016/0074531 A1 | 3/2016 | Kishimoto | |
| 2016/0074532 A1 | 3/2016 | Kishimoto | |
| 2016/0128986 A1 | 5/2016 | O'Neil et al. | |
| 2016/0128987 A1 | 5/2016 | Griset et al. | |
| 2016/0220501 A1 | 8/2016 | Fraser et al. | |
| 2016/0243253 A1 | 8/2016 | Fraser et al. | |
| 2016/0256401 A1 | 9/2016 | Fraser et al. | |
| 2016/0279234 A1 | 9/2016 | Kishimoto et al. | |
| 2017/0258927 A1 | 9/2017 | Johnston | |
| 2017/0349433 A1 | 12/2017 | Lipford et al. | |
| 2018/0043023 A1 | 2/2018 | Ilyinski et al. | |
| 2018/0071394 A1 | 3/2018 | O'Neil et al. | |
| 2018/0085319 A1 | 3/2018 | Kishimoto | |
| 2018/0193482 A1 | 7/2018 | Ilyinski et al. | |
| 2018/0256709 A1 | 9/2018 | Zepp et al. | |
| 2018/0289776 A1 | 10/2018 | Johnston et al. | |
| 2019/0076458 A1 | 3/2019 | Kishimoto et al. | |
| 2019/0076522 A1 | 3/2019 | Altreuter et al. | |

FOREIGN PATENT DOCUMENTS

| | | |
|---|---|---|
| CN | 101703781 A | 5/2010 |
| CN | 101861165 A | 10/2010 |
| CN | 102871966 B | 11/2013 |
| EP | 0759941 B1 | 9/2000 |
| EP | 1 932 538 A1 | 6/2008 |
| EP | 2073848 A2 | 7/2009 |
| EP | 2345412 A1 | 7/2011 |
| EP | 2522338 A2 | 11/2012 |
| EP | 2217269 B1 | 4/2017 |
| JP | H01-502909 A | 10/1989 |
| JP | 2005-516893 A | 6/2005 |
| JP | 2006-257095 | 9/2006 |
| JP | 2007-532517 A | 11/2007 |
| JP | 2008-515806 | 5/2008 |
| JP | 2008-532953 A | 8/2008 |
| JP | 2009-531068 | 9/2009 |
| JP | 2010-100578 A | 5/2010 |
| JP | 2010-514805 | 5/2010 |
| JP | 2010-533160 A | 10/2010 |
| JP | 2012-502930 A | 2/2012 |
| KR | 10-2010-0099849 A | 9/2010 |
| WO | WO 88/06451 A1 | 9/1988 |
| WO | WO 95/11696 A1 | 5/1995 |
| WO | WO 96/12406 A1 | 2/1996 |
| WO | WO 96/20698 A2 | 7/1996 |
| WO | WO 98/10056 A1 | 12/1998 |
| WO | WO 99/22762 A1 | 5/1999 |
| WO | WO 99/34826 A1 | 7/1999 |
| WO | WO 02/09770 A1 | 2/2002 |
| WO | WO 02/32404 A2 | 4/2002 |
| WO | WO 02/088304 A2 | 11/2002 |
| WO | WO 2003/033526 A2 | 4/2003 |
| WO | WO 03/094840 A2 | 11/2003 |
| WO | WO 2005/097116 A1 | 10/2005 |
| WO | WO 2006/041890 A2 | 4/2006 |
| WO | WO 2006/094507 A1 | 9/2006 |
| WO | WO 2007/067683 A2 | 6/2007 |
| WO | WO 2007/087341 A2 | 8/2007 |
| WO | WO 2007/098254 A2 | 8/2007 |
| WO | WO 2007/133835 A2 | 11/2007 |
| WO | WO 2008/036374 A2 | 3/2008 |
| WO | WO 2008/043157 A1 | 4/2008 |
| WO | WO 2008/073558 A2 | 6/2008 |
| WO | WO 2008/083331 A2 | 7/2008 |
| WO | WO 2008/109163 A1 | 9/2008 |
| WO | WO 2008/150868 A1 | 12/2008 |
| WO | WO-2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/027471 A2 | 3/2010 |
| WO | WO 2010/037402 A1 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/075072 A2 | 7/2010 |
| WO | WO 2010/116141 A2 | 10/2010 |
| WO | WO 2010/123569 A2 | 10/2010 |
| WO | WO 2010/125565 A2 | 11/2010 |
| WO | WO 2010/138192 A2 | 12/2010 |
| WO | WO 2010/138193 A2 | 12/2010 |
| WO | WO 2010/138194 | 12/2010 |
| WO | WO 2011/033090 A1 | 3/2011 |
| WO | WO 2011/109833 A2 | 9/2011 |
| WO | WO 2011/150240 A1 | 12/2011 |
| WO | WO 2011/156119 A1 | 12/2011 |
| WO | WO 2012/019041 A2 | 2/2012 |
| WO | WO 2012/021512 A2 | 2/2012 |
| WO | WO 2012/054920 A2 | 4/2012 |
| WO | WO 2012/149247 A2 | 11/2012 |
| WO | WO 2012/149252 A2 | 11/2012 |
| WO | WO 2012/149255 A2 | 11/2012 |
| WO | WO-2012/149259 A1 | 11/2012 |
| WO | WO 2012/149265 A2 | 11/2012 |
| WO | WO 2012/149268 A1 | 11/2012 |
| WO | WO 2012/149393 A2 | 11/2012 |
| WO | WO 2012/149405 A2 | 11/2012 |
| WO | WO 2012/149411 A1 | 11/2012 |
| WO | WO 2012/158362 A1 | 11/2012 |
| WO | WO 2013/058812 A1 | 4/2013 |
| WO | WO-2014/179771 A1 | 11/2014 |
| WO | WO 2015/162594 A2 | 10/2015 |

OTHER PUBLICATIONS

U.S. Appl. No. 14/717,451, filed May 20, 2015, Ilyinskii et al.
PCT/US2014/036687, Sep. 22, 2014, International Search Report and Written Opinion.
PCT/US2014/036687, Nov. 12, 2015, International Search Report and Written Opinion.
EP 14792080.5, Oct. 14, 2016, Extended European Search Report.
International Search Report and Written Opinion dated Sep. 22, 2014 in connection with PCT/US2014/036687.
International Preliminary Report on Patentability dated Nov. 12, 2015 in connection with PCT/US2014/036687.
Extended European Search Report dated Oct. 14, 2016 in connection with EP 14792080.5.
"Pluronic." Oxford Dictionary entry accessed via www.oxforddictionary.com on May 6, 2016. 8 pages.
Aalbers et al., Preclinical Potency and Biodistribution Studies of an AAV 5 Vector Expressing Human Interferon-β (ART-I02) for Local Treatment of Patients with Rheumatoid Arthritis. PLoS One. Jun. 24, 2015;10(6):e0130612. doi:10.1371/journal.pone.0130612. 17 pages.
Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.

(56) References Cited

OTHER PUBLICATIONS

Amu et al., Regulatory B cells prevent and reverse allergic airway inflammation via FoxP3-positive T regulatory cells in a murine model. J Allergy Clin Immunol. Mar. 22, 2010;125(5):1114-24.

Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

Arruda et al., Strategies to modulate immune responses: a new frontier for gene therapy. Mol Ther. Sep. 2009;17(9):1492-503. doi: 10.1038/mt.2009.150. Epub Jul. 7, 2009. Review.

Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05.001. Epub May 5, 2010.

Bae et al., Vinyl sulfone-terminated PEG-PLLA diblock copolymer for thiol-reactive polymeric micelle. Apr. 9, 2009;42(10):3437-42.

Barzel et al., Promoterless gene targeting without nucleases ameliorates haemophilia B in mice. Nature. Jan. 15, 2015;517(7534):360-4. doi: 10.1038/nature13864. Epub Jul. 15, 2015. 21 pages.

Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47.

Bawarski et al., Emerging nanopharmaceuticals. Nanomed: Nanotechnol Biol Med. 2008;4:273-82.

Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.

Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.

Bocian et al., Rapamycin, unlike cyclosporine A, enhances suppressive functions of in vitro-induced CD4+CD25+ Tregs. Nephrol Dial Transplant. Mar. 2010;25(3):710-7. doi: 10.1093/ndt/gfp586.

Boden et al., Regulatory T cells in inflammatory bowel disease. Curr Opin Gastroenterol. Nov. 2008;24(6):733-41.

Bouaziz et al., Regulatory B cells as inhibitors of immune responses and inflammation. Immunol Rev. Aug. 2008;224:201-14. doi: 10.1111/j.1600-065X.2008.00661.x. Review.

Brown et al., Endogenous microRNA regulation suppresses transgene expression in hematopoietic lineages and enables stable gene transfer. Nat Med. May 2006;12(5):585-91. Epub Apr. 23, 2006.

Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.

Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3, 2009.

Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: 50264-410X(14)01129-3. doi: 10.1016/j.vaccine.2014.08.016. 9 pages.

Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.

Chen et al., Targeting transgene to the heart and liver with AAV9 by different promoters. Clin Exp Pharmacol Physiol. Oct. 2014;42(10):1108-17. doi: 10.1111/1440-1681.12453. Original Article. 24 pages.

Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.

Colman et al., Effects of amino acid sequence changes on antibody-antigen interactions. Res Immunol. Jan. 1994;145(1):33-6.

Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.

Corti et al., B-Cell Depletion is Protective Against Anti-AAV Capsid Immune Response: A Human Subject Case Study. Mol Ther Methods Clin Dev. 2014;1. pii: 14033. 7 pages.

Cvetanovich et al., Human regulatory T cells in autoimmune diseases. Curr Opin Immunol. Dec. 2010;22(6):753-60. Epub Sep. 24, 2010.

Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008;85(4):983-92.

Davila et al., Cell-based immunotherapy with suppressor CD8+ T cells in rheumatoid arthritis. J Immunol. Jun. 1, 2005;174(11):7292-301.

Denti et al., Body-wide gene therapy of Duchenne muscular dystrophy in the mdx mouse model. Proc Natl Acad Sci U S A. Mar. 7, 2006;103(10):3758-63. Epub Feb. 24, 2006.

Dilillo et al., B10 cells and regulatory B cells balance immune responses during inflammation, autoimmunity, and cancer. Ann N Y Acad Sci. Jan. 2010;1183:38-57. doi: 10.1111/j.1749-6632.2009.05137.x. Review.

Dinarvand et al., Polylactide-co-glycolide nanoparticles for controlled delivery of anticancer agents. Int J Nanomedicine. 2011;6:877-95. doi: 10.2147/IJN.S18905. Epub May 27, 2011.

Dinesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.

Dobrolovskaja et al., Immunological properties of engineered nonomaterials. Nat Nanotechnol. Aug. 2007;2(8):469-78. Review.

Düchs, Dissertation entitled: Effects of Toll-like receptor agonists on the pathogenesis of atopic asthma in mice, University of Würzburg, Sep. 2011. 147 pages.

Eghtesad et al., Effect of rapamycin on immunity induced by vector-mediated dystrophin expression in mdx skeletal muscle. Sci Rep. 2012;2:399. doi: 10.1038/srep00399. Epub May 8, 2012. 6 pages.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.

Falk et al., Induction and suppression of an autoimmune disease by oligomerized T cell epitopes: enhanced in vivo potency of encephalitogenic peptides. J Exp Med. Feb. 21, 2000;191(4):717-30.

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Faunce et al., Cutting edge: in vitro-generated tolerogenic APC induce CD8+ regulatory cells that can suppress ongoing experimental autoimmune encephalomyelitis. J Immunol. Feb. 15, 2004;172(4):1991-5.

Fifis et al., Size-dependent immunogenicity: therapeutic and protective properties of nano-vaccines against tumors. J Immunol. Sep. 1, 2004;173(5):3148-54.

Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. DOI: 10.1002/art.27913. 2 pages.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Fraser et al., Nanoparticle therapy for allergic and inflammatory disease. Anti-Inflammatory & Anti-Allergy Agents Med Chem. Mar. 2010;9(1):54-70.

(56) References Cited

OTHER PUBLICATIONS

Gajofatto et al., Treatment strategies for multiple sclerosis: When to start, when to change, when to stop? World J Clin Cases. Jul. 16, 2015;3(7):545-55. doi: 10.12998/wjcc.v3.i7.545.

Gao et al., Contrasting effects of cyclosporine and rapamycin in de novo generation of alloantigen-specific regulatory T cells. Am J Transplant. Jul. 2007;7(7):1722-32. Epub May 19, 2007.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Harnessing nanoparticles for immune modulation. Trends Immunol. Jul. 2015;36(7):419-27.

Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Haddadi et al., Delivery of rapamycin by PLGA nanoparticles enhances its suppressive activity on dendritic cells. J Biomed Mater Res A. Mar. 15, 2008;84(4):885-98.

Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. doi: 10.1016/j.vaccine.2008.07.035. Epub Aug. 3, 2008.

Hamdy et al., Part I: targeted particles for cancer immunotherapy. Curr Drug Deliv. May 2011;8(3):261-73.

Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.

Hamdy et al., The immunosuppressive activity of polymeric micellar formulation of cyclosporine A: in vitro and in vivo studies. AAPS J. Jun. 2011;13(2):159-68. doi: 10.1208/s12248-011-9259-8. Epub Feb. 19, 2011.

Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.

Hashimoto et al., Stimulation of host NKT cells by synthetic glycolipid regulates acute graft-versus-host disease by inducing Th2 polarization of donor T cells. J Immunol. Jan. 1, 2005;174(1):551-6.

Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.

Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.

Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.

Jiang et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.

Jones, Critically assessing the state-of-the-art in protein structure prediction. Pharmacogenomics J. 2001;1(2):126-34. Review.

Kang et al., Very low-dose tolerance with nucleosomal peptides controls lupus and induces potent regulatory T cell subsets. J Immunol. Mar. 15, 2005;174(6):3247-55.

Karamloo et al., Prevention of allergy by a recombinant multi-allergen vaccine with reduced IgE binding and preserved T cell epitopes. Eur J Immunol. Nov. 2005;35(11):3268-76.

Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.

Kim et al., Effects of cyclosporine and rapamycin on immunoglobulin production by preactivated human B cells. Clin Exp Immunol. Jun. 1994;96(3):508-12.

Kim et al., Inhibition of follicular T-helper cells by CD8(+) regulatory T cells is essential for self. Nature. Sep. 16, 2010;467(7313):328-32.

Kim et al., Simvastatin induces Foxp3+ T regulatory cells by modulation of transforming growth factor-beta signal transduction. Immunology. Aug. 2010;130(4):484-93. doi: 10.1111/j.1365-2567-2010-03269.x. Epub Apr. 12, 2010.

Kingsley et al., Transplantation tolerance: lessons from experimental rodent models. Transpl Int. Oct. 2007;20(10):828-41. Epub Aug. 17, 2007.

Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.

Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.

Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013.

Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.

Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.

Lutsiak et al., Analysis of poly(D,L-lactic-co-glycolic acid) nanosphere uptake by human dendritic cells and macrophages in vitro. Pharm Res. Oct. 2002;19(10):1480-7.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

Mason, Functional Analysis of the Cysteine Residues of Activin A. Mol Endocrinol. 1994;8(3):325-32.

McMahon et al., Epitope spreading initiates in the CNS in two mouse models of multiple sclerosis. Nat Med. Mar. 2005;11(3):335-9. Epub Feb. 27, 2005.

Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015.037.

Menzies et al., Simvastatin does not exhibit therapeutic anti-inflammatory effects in asthma. J Allergy Clin Immunol. Feb. 2007;119(2):328-35. Epub Dec. 4, 2006.

Mingozzi et al., Modulation of tolerance to the transgene product in a nonhuman primate model of AAV-mediated gene transfer to liver. Blood. Oct. 1, 2007;110(7):2334-41. Epub Jul. 3, 2007.

Miyara et al., Therapeutic approaches to allergy and autoimmunity based on FoxP3+ regulatory T-cell activation and expansion. J Allergy Clin Immunol. Apr. 2009;123(4):749-55.

(56) References Cited

OTHER PUBLICATIONS

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages.

Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.

Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.

Neuhaus et al., mTOR inhibitors: an overview. Liver Transpl. Jun. 2001;7(6):473-84.

Ngo et al., In The Protein Folding Problem and Tertiary Structure Prediction, 1994. Eds Mertz et al. Birkhauser. Boston, MA. 1994:433,491-5.

Nixon et al., Synthetic peptides entrapped in microparticles can elicit cytotoxic T cell activity. Vaccine. Nov. 1996;14(16):1523-30.

Oh et al., CD4+CD25+ regulatory T cells in autoimmune arthritis. Immunol Rev. Jan. 2010;233(1):97-111.

Omata et al., Ovalbumin-specific IgE modulates ovalbumin-specific T-cell response after repetitive oral antigen administration. J Allergy Clin Immunol. Apr. 2005;115(4):822-7.

Paolicelli et al., Surface-modified PLGA-based nanoparticles that can efficiently associate and deliver virus-like particles. Nanomedicine (Lond). Aug. 2010;5(6):843-53.

Papisov, Acyclic polyacetals from polysaccharides: biomimetic biomedical "stealth" polymers. ACS Symposium Series. Feb. 15, 2001;786:301-14. Chapter 19 from Biopolymers and Polysaccharides and Agroproteins. DOI: 10.1021/bk-2001-0786.ch019.

Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.

Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.

Ran et al., In vivo genome editing using *Staphylococcus aureus* Cas9. Nature. Apr. 9, 2015;520(7546):186-91. doi: 10.1038/nature14299. Epub Apr. 1, 2015.

Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.

Samuel et al., Nanoparticle delivery systems for control of immunity. Proceedings of the 2004 Intl. Conference on MEMS, NANO and Smart Systems (ICMENS '04). IEEE 2004. 3 pages.

Samuel et al., Polymeric nanoparticles for targeted delivery of Therapeutic Vaccines to dendritic cells. Proceedings of the International Conference on MEMS, NANO and Smart Systems. (ICMENS '03). IEEE 2003. 5 pages.

Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.

Seffernick et al., Melamine deaminase and atrazine chlorohydrolase: 98 percent identical but functionally different. J Bacteriol. Apr. 2001;183(8):2405-10.

Senís et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014. Supporting Information. 26 pages.

Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.

Shen et al., Combined effect of cyclosporine and sirolimus on improving the longevity of recombinant adenovirus-mediated transgene expression in the retina. Arch Ophthalmol. Jul. 2001;119(7):1033-43.

Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.

Skolnick et al., From genes to protein structure and function: novel applications of computational approaches in the genomic era. Trends Biotechnol. Jan. 2008;18(1):34-9. Review.

Soroosh et al., Th9 and allergic disease. Immunology. Aug. 2009;127(4):450-8. doi: 10.1111/j.1365-2567.2009.03114.x.

Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.

Stepkowski et al., Inhibition of host-versus-graft and graft-versus-host responses after small bowel transplantation in rats by rapamycin. Transplantation. Feb. 1992;53(2):258-64.

Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.

Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.

Tarzi et al., Peptide immunotherapy for allergic disease. Expert Opin Biol Ther. Jul. 2003;3(4):617-26. Review.

Thomson et al., Immunoregulatory functions of mTOR inhibition. Nat Rev Immunol. May 2009;9(5):324-37. doi: 10.1038/nri2546.

Tosatto et al., Large-scale prediction of protein structure and function from sequence. Curr Pharm Des. 2006;12(17):2067-86. Review.

Tuohy, Peptide determinants of myelin proteolipid protein (PLP) in autoimmune demyelinating disease: a review. Neurochem Res. Aug. 1994;19(8):935-44.

Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.

Vila et al., Regulatory T cells and autoimmunity. Curr Opin Hematol. Jul. 2009;16(4):274-9.

Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.

Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.

Witkowski et al., Conversion of a beta-ketoacyl synthase to a malonyl decarboxylase by replacement of the active-site cysteine with glutamine. Biochemistry. Sep. 7, 1999;38(36):11643-50.

Wu et al., Humanization of a murine monoclonal antibody by simultaneous optimization of framework and CDR residues. J Mol Biol. Nov. 19, 1999;294(1):151-62.

Yamaguchi et al., Around hematological malignancies. Trends in Hematological Malignancies. 2010;2(2):96-98.

Yamaki et al., Preventive and therapeutic effects of rapamycin, a mammalian target of rapamycin inhibitor, on food allergy in mice. Allergy. Oct. 2012;67(10):1259-70. doi: 10.1111/all.12000. Epub Aug. 23, 2012.

Yeste et al., Nanoparticle-mediated codelivery of myelin antigen and a tolerogenic small molecule suppresses experimental autoim-

(56) References Cited

OTHER PUBLICATIONS mune encephalomyelitis. Proc Natl Acad Sci U S A. Jul. 10, 2012;109(28):11270-5. doi: 10.1073/pnas.1120611109. Epub Jun. 27, 2012.
Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.
Zhang et al., The mechanism of B lymphocytes in inducing immune tolerance. Immunol J. Jul. 2010;26(7):643-6.
Zhang-Hoover et al., Tolerogenic APC generate CD8+ T regulatory cells that modulate pulmonary interstitial fibrosis. J Immunol. Jan. 1, 2004;172(1):178-85.
Zhou et al., Updates of mTOR inhibitors. Anticancer Agents Med Chem. Sep. 2010;10(7):571-81.
Zweers, Biodegradable nanoparticles of intravascular drug delivery. Unversiteit Twente, 2003.
Beevers et al., Curcumin inhibits the mammalian target of rapamycin-mediated signaling pathways in cancer cells. Int J Cancer. Aug. 15, 2006;119(4):757-64.
Dao et al., Pharmacokinetics and pharmacodynamics evaluation of therapeutic protein drugs. China Pharm. Dec. 31, 2007;18(32):2546-7.
Delgoffe et al., The mTOR kinase differentially regulates effector and regulatory T cell lineage commitment. Immunity. Jun. 19, 2009;30(6):832-44. doi:10.1016/j.immuni.2009.04.014.
Fourtounas et al., Different immunosuppressive combinations on T-cell regulation in renal transplant recipients. Am J Nephrol. 2010;32(1):1-9. doi:10.1159/000313940. Epub May 20, 2010.
Maldonado et al., Polymeric synthetic nanoparticles for the induction of antigen-specific immunological tolerance. Proc Natl Acad Sci U S A. Jan. 13, 2015;112(2):E156-65. doi: 10.1073/pnas.1408686111. Epub Dec. 29, 2014.
Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.
Sbiera et al., Influence of short-term glucocorticoid therapy on regulatory T cells in vivo. PLoS One. 2011;6(9):e24345. doi: 10.1371/journal.pone.0024345. Epub Sep. 2, 2011.
U.S. Appl. No. 14/273,099, filed May 8, 2014, Zepp et al.
U.S. Appl. No. 14/658,040, filed Mar. 13, 2015, Zepp et al.
U.S. Appl. No. 13/289,211, filed Nov. 4, 2011, Zepp et al.
U.S. Appl. No. 14/802,260, filed Jul. 17, 2015, Altreuter et al.
U.S. Appl. No. 13/457,936, filed Apr. 27, 2012, Kishimoto et al.
U.S. Appl. No. 13/458,220, filed Apr. 27, 2012, Fraser et al.
U.S. Appl. No. 14/161,660, filed Jan. 22, 2014, Maldonado.
U.S. Appl. No. 14/846,964, filed Sep. 7, 2015, Kishimoto.
U.S. Appl. No. 14/846,967, filed Sep. 7, 2015, Kishimoto.
[No Author Listed] Selecta Biosciences Announces Dosing of First Patent in Phase 1 b Clinical Trial of SEL-212, Designed to be The First Non-Immunogenic Biologic Treatment for Gout. Press Release. Dec. 23, 2015. Retrieved from the Internet via http://selectabio.com/2015/12/23/selecta-biosciences-announces-dosing-of-first-patient-in-phase-1b-clinical-trial-of-sel-212-designed-to-be-the-first-non-immunogenic-biologic-treatment-for-gout. Last access on May 10, 2017.
Bayle et al., Rapamycin analogs with differential binding specificity permit orthogonal control of protein activity. Chem Biol. Jan. 2006;13(1):99-107.
Berhanu et al., Pegloticase failure and a possible solution: Immunosuppression to prevent intolerance and inefficacy in patients with gout. Semin Arthritis Rheum. Jun. 2017;46(6):754-758. doi: 10.1016/j.semarthrit.2016.09.007. Epub Sep. 20, 2016.
Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.
Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. doi: 10.1186/ar4500.
Ishii, [Allergen-specific immunotherapy utilizing mechanisms for immune; regulation]. Nihon . Rinsho Meneki Gakkai Kaishi. Oct. 2008;31(5):392-8. Review.
Kishimoto et al., Improving the efficacy and safety of biologic drugs with; tolerogenic nanoparticles. Nat Nanotechnol. Oct. 2006;11(10):890-899. doi:; 10.1038/nnano.2016.135. Epub Aug. 1, 2016.
Kunisawa et al., Fusogenic liposome functions as an efficient immunoadjuvant in inducing humoral immune-responses to soluble antigen. Drug Delivery System. Jan. 1998;13(1):21-26.
Lipsky et al., Pegloticase immunogenicity: the relationship between efficacy and antibody development in patients treated for refractory chronic gout. Arthritis Res Ther. Mar. 4, 2014;16(2):R60. doi: 10.1186/ar4497.
Macary et al., Ovalbumin-specific, MHC class I-restricted, alpha beta-positive, Tc1 and Tc0 CD8+ T cell clones mediate the in vivo inhibition of rat IgE. J Immunol. Jan. 15, 1998;160(2):580-7.
Maher et al., Targeting cytotoxic T lymphocytes for cancer immunotherapy. Br J Cancer. Aug. 31, 2004;91(5)1317-21. Review.
McKay et al., A novel anti-inflammatory role of simvastatin in a murine model of allergic asthma. J Immunol. Mar. 1, 2004;172(5):2903-8.
Mine et al., Epitope characterization of ovalbumin in BALB/c mice using different entry routes. Biochim Biophys Acta. Feb. 2007;1774(2):200-12. Epub Dec. 19, 2006.
Quarcoo et al., Resiquimod, a new immune response modifier from the family of imidazoquinolinamines, inhibits allergen-induced Th2 responses, airway inflammation and airway hyper-reactivity in mice. Clin Exp Allergy. Aug. 2004;34(8):1314-20.
Reddy et al., Detection of autoreactive myelin proteolipid protein 139-151-specific T cells by using MHC II (lAs) tetramers. J Immunol. Jan. 15, 2003;170(2):870-7.
Renz et al., Comparison of the allergenicity of ovalbumin and ovalbumin peptide 323-339. Differential expansion of V beta-expressing T cell populations. J Immunol. Dec. 15, 1993;151(12):7206-13.
Rice-Ficht et al., Polymeric particles in vaccine delivery. Curr Opin Microbiol. Feb. 2010;13(1):106-12. doi: 10.1016/j.mib.2009.12.001. Epub Jan. 14, 2010. Review.
Alewine et al., Efficacy of RG7787, a next-generation mesothelin-targeted immunotoxin, against triple-negative breast and gastric cancers. Mol Cancer Ther. Nov. 2014;13(11):2653-61. doi: 10.1158/1535-7163.MCT-14/0132. Epub Sep. 19, 2014.
Azzi et al., Polylactide-cyclosporin a nanoparticles for targeted immunosuppression. FASEB J. Oct. 2010;24(10):3927-38. doi: 10.1096/fj.10-154690. Epub Jun. 14, 2010.
Baker et al., Immunogenicity of protein therapeutics: The key causes, consequences and challenges. Self Nonself-Immune Recognition and Signaling. Dec. 1, 2010;1(4):314-22.
Bi et al., High-efficiency targeted editing of large viral genomes by RNA-guided nucleases. PLoS Pathog. May 1, 2014;10(5):e1004090. doi: 10.1371/journal.ppat.1004090. eCollection May 2014.
Goyenvalle et al., Rescue of dystrophic muscle through U7 snRNA-mediated exon skipping. Science. Dec. 3, 2004;306(5702):1796-9. Epub Nov. 4, 2004.
Hassan et al., Major cancer regressions in mesothelioma after treatment with an anti-mesothelin immunotoxin and immune suppression. Sci Transl Med. Oct. 23, 2013;5(208):208ra147. doi: 10.1126/scitranslmed.3006941.
Maldonado et al., How tolerogenic dendritic cells induce regulatory T cells. Adv Immunol. 2010;108:111-65. doi: 10.1016/B978-0-12-380995-7.00004-5. Review.
Mazor et al., Immunogenicity of therapeutic recombinant immunotoxins. Immunol Rev. Mar. 2016;270(1):152-64. doi: 10.1111/imr.12390. Review.
McFarland et al., Ovalbumin(323-339) peptide binds to the major histocompatibility complex class II I-A(d) protein using two functionally distinct registers. Biochemistry. Dec. 14, 1999;38(50):16663-70.
Mori et al., Biological drug for refractory juvenile idiopathic arthritis. Clin Rheum. 2006;18(2):191-6.

(56) References Cited

OTHER PUBLICATIONS

Nayak et al., Prophylactic immune tolerance induced by changing the ratio of antigen-specific effector to regulatory T cells. J Thromb Haemost. Sep. 2009;7(9):1523-32. doi: 10.1111/j.1538-7836.2009.03548.x. Epub Jul. 6, 2009.
Onda et al., Tofacitinib suppresses antibody responses to protein therapeutics in murine hosts. J. Immunol. Jul. 1, 2014;193(1):48-55. doi: 10.4049/jimmunol.140006. Epub Jun. 2, 2014.
Pastan et al., Immunotoxin therapy of cancer. Nat Rev Cancer. Jul. 2006;6(7):559-65. Review.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2016;16(3):257-65. doi: 10.1016/S1470-2045(15)70054-9. Epub Feb. 20, 2015.
Rybak-Smith et al., Complement activation by carbon nanotubes. Adv Drug Deliv Rev. Sep. 16, 2011 16;63(12):1031-41. doi: 10.1016/j.addr.2011.05.012. Epub Jun. 12, 2011. Review.
Sato et al., Induction of immunotolerance by the application of chase-sulzberger effect. JP J Translpant. 1995;30(3):231-9.
Sato et al., Prolongation of the immunosuppression by repeated injections of donor antigen via the portal vein. JP J Transplant. 1995;30(2):149-54.
Zhang , Introduction to basic medicine. China University of Science and Technology Press. Aug. 31, 2012:423.
Zhang et al., Induction of tolerance to FVIII using nanoparticles in a murine model of hemophilia A. Blood. Nov. 15, 2013;122:2337.
U.S. Appl. No. 13/948,129, filed Jul. 22, 2013, Zepp et al.
U.S. Appl. No. 12/788,261, filed May 26, 2010, Lipford et al.
U.S. Appl. No. 15/889,014, filed Feb. 5, 2018, Zepp et al.
U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 15/629,973, filed Jun. 22, 2017, Lipford et al.
U.S. Appl. No. 13/116,488, filed May 26, 2011, Bratzler et al.
U.S. Appl. No. 15/684,896, filed Aug. 23, 2017, Ilyinskii et al.
U.S. Appl. No. 13/116,556, filed May 26, 2011, Bratzler et al.
U.S. Appl. No. 13/428,340, filed Mar. 23, 2012, Altreuter et al.
U.S. Appl. No. 14/810,418, filed Jul. 27, 2015, Fraser et al.
U.S. Appl. No. 15/050,397, filed Feb. 22, 2016, Fraser et al.
U.S. Appl. No. 16/056,204, filed Aug. 6, 2018, Altreuter et al.
U.S. Appl. No. 13/560,955, filed Jul. 27, 2012, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 13/457,994, filed Apr. 27, 2012, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 14/810,466, filed Jul. 27, 2015, Kishimoto et al.
U.S. Appl. No. 14/810,472, filed Jul. 27, 2015, Fraser et al.
U.S. Appl. No. 14/810,476, filed Jul. 27, 2015, Maldonado.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,058, filed May 2, 2014, Kishimoto.
U.S. Appl. No. 14/269,056, filed May 2, 2014, Maldonado et al.
U.S. Appl. No. 14/269,042, filed May 2, 2014, Kishimoto et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 16/100,040, filed Aug. 9, 2018, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 15/456,520, filed Mar. 11, 2017, Johnston.
U.S. Appl. No. 15/685,648, filed Aug. 24, 2017, O'Neil.
U.S. Appl. No. 15/717,710, filed Sep. 27, 2017, Kishimoto.
U.S. Appl. No. 15/863,076, filed Jan. 5, 2018, Ilyinskii et al.
U.S. Appl. No. 15/917,742, filed Mar. 11, 2018, Johnston.
U.S. Appl. No. 16/159,166, filed Oct. 12, 2018, Ilyinskii et al.
Abeles, PEG-ing down (and preventing?) the cause of pegloticase failure. Arthritis Res Ther. May 30, 2014;16(3):112. doi: 10.1186/ar4572.
Aronovich et al., Quantitative analysis of α-L-iduronidase expression in immunocompetent mice treated with the Sleeping Beauty transposon system. PLoS One. Oct. 21, 2013;8(10):e78161. doi: 10.1371/journal.pone.0078161. eCollection 2013.
Comas et al., New nanoformulation of rapamycin Rapatar extends lifespan in homozygous p53-/- mice by delaying carcinogenesis. Aging (Albany NY). Oct. 2012;4(10):715-22.
Crittenden et al., New therapies for gout. Annu Rev Med. 2013;64:325-37. doi: 10.1146/annurev-med-080911-105830.
Dai et al., Cellular and humoral immune responses to adenoviral vectors containing factor IX gene: tolerization of factor IX and vector antigens allows for long-term expression. Proc Natl Acad Sci U S A. Feb. 28, 1995;92(5):1401-5.
Dupont et al., The evolving role of sirolimus in renal transplantation. QJM. Jun. 2003;96(6):401-9. Review.
Garay et al., Therapeutic perspectives on uricases for gout. Joint Bone Spine. May 2012;79(3):237-42. doi: 10.1016/j .jbspin.2012.01.004. Epub Feb. 25, 2012. Review.
Heidt et al., Effects of immunosuppressive drugs on purified human B cells: evidence supporting the use of MMF and rapamycin. Transplantation. Nov. 2008;86(9):1292-1300. doi: 10.1097/TP.0b013e3181874a36.
Horibe et al., Rapamycin-conditioned, alloantigen-pulsed dendritic cells promote indefinite survival of vascularized skin allografts in association with T regulatory cell expansion. Transplant Immunol. Feb. 2008;18(4):307-318. doi: 10.1016/j.trim.2007.10.007.
Hushmendy et al., Select phytochemicals suppress human T-lymphocytes and mouse splenocytes suggesting their use in autoimmunity and transplantation. Nutr Res. Aug. 2009;29(8):568-78. doi: 10.1016/j.nutres.2009.08.003. PubMed PMID: 19761891.
Kaplan et al., Transient immunosuppression with deoxyspergualin improves longevity of transgene expression and ability to readminister adenoviral vector to the mouse lung. Hum Gene Ther. Jun. 10, 1997;8(9):1095-104.
Lowenstein, The case for immunosuppression in clinical gene transfer. Mol Ther. Aug. 2005;12(2):185-6.
Matsui et al., Delivery of full-length factor VIII using a piggyBac transposon vector to correct a mouse model of hemophilia A. PLoS One. Aug. 15, 2014;9(8):e104957. doi: 10.1371/journal.pone.0104957. eCollection 2014.
Ming et al. Medical Immunology. Yunnan University Press. Feb. 28, 2009. p. 40-41.
Perez-Ruiz et al., Lesinurad in combination with allopurinol: results of a phase 2, randomised, double-blind study in patients with gout with an inadequate response to allopurinol. Ann Rheum Dis. Jun. 2016;75(6):1074-80. doi: 10.1136/annrheumdis-2015-207919. Epub Jan. 7, 2016. PubMed PMID: 26742777; PubMed Central PMCID: PMC4893096.
Reinders et al., New advances in the treatment of gout: review of pegloticase. Ther Clin Risk Manag. Oct. 27, 2010;6:543-50. doi: 10.2147/TCRM.S6043.
Sundy et al., Reduction of plasma urate levels following treatment with multiple doses of pegloticase (polyethylene glycol-conjugated uricase) in patients with treatment-failure gout: results of a phase II randomized study. Arthritis Rheum. Sep. 2008;58(9):2882-91. doi: 10.1002/art.23810.
Tardieu et al., Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. Jun. 2014;25(6):506-16. doi: 10.1089/hum.2013.238. Epub May 5, 2014.
Ulivieri et al., Simvastatin impairs humoral and cell-mediated immunity in mice by inhibiting lymphocyte homing, T-cell activation and antigen cross-presentation. Eur J Immunol. Oct. 2008;38(10):2832-44. doi: 10.1002/eji.200838278. PubMed PMID: 18958884.
Vogt et al., Urate oxidase (rasburicase) for treatment of severe tophaceous gout. Nephrol Dial Transplant. Feb. 2005;20(2):431-3.

(56) References Cited

OTHER PUBLICATIONS

Wang et al., Sustained AAV-mediated dystrophin expression in a canine model of Duchenne muscular dystrophy with a brief course of immunosuppression. Mol Ther. Jun. 2007;15(6):1160-6. Epub Apr. 10, 2007.

* cited by examiner

METHODS RELATED TO ADMINISTERING IMMUNOSUPPRESSANTS AND THERAPEUTIC MACROMOLECULES AT A REDUCED PHARMACODYNAMICALLY EFFECTIVE DOSE

RELATED APPLICATIONS

This application claims the benefit under 35 U.S.C. § 119 of U.S. provisional application 61/819,517, filed May 3, 2013; application 61/881,851, filed Sep. 24, 2013; application 61/881,913, filed Sep. 24, 2013; application 61/881,921, filed Sep. 24, 2013; application 61/907,177, filed Nov. 21, 2013; application 61/948,313, filed Mar. 5, 2014; and application 61/948,384, filed Mar. 5, 2014, the entire contents of each of which are incorporated herein by reference.

FIELD OF THE INVENTION

This invention relates to immunosuppressant doses, in some embodiments attached to synthetic nanocarriers that are administered concomitantly with a therapeutic macromolecule, and related methods. The compositions and methods allow for efficient pharmacodynamic effects specific to the therapeutic macromolecule. The compositions and methods provided can, therefore, be used to generate pharmacodynamic responses in a subject even at reduced doses of the therapeutic macromolecule. The compositions and methods provided herein can also be administered repeatedly concomitantly to generate desired pharmacodynamic and immunologic effects.

BACKGROUND OF THE INVENTION

Therapeutic treatments, such as protein or enzyme replacement therapies, often result in undesired immune responses to the particular therapeutic. In such cases, cells of the immune system recognize the therapeutic as foreign and attempt to neutralize or destroy it, just as they attempt to destroy infecting organisms such as bacteria and viruses. Such undesired immune responses can neutralize the efficacy of the therapeutic treatment or cause hypersensitive reactions to the therapeutic. These undesired responses may be reduced through the use of immunosuppressant drugs. Conventional immunosuppressant drugs, however, are broad-acting, and the use of broad-acting immunosuppressants are associated with a risk of severe side effects, such as tumors, infections, nephrotoxicity and metabolic disorders. Accordingly, new therapies would be beneficial.

SUMMARY OF THE INVENTION

In one aspect, a method comprising providing an immunosuppressant dose, wherein in some embodiments the immunosuppressant dose is attached to synthetic nanocarriers, and administering a reduced pharmacodynamically effective dose of a therapeutic macromolecule concomitantly with the immunosuppressant dose to a subject is provided. In one embodiment, the concomitant administration is according to a protocol that has been demonstrated to result in a pharmacodynamic effect with the reduced pharmacodynamically effective dose of the therapeutic macromolecule upon concomitant administration with the immunosuppressant dose, as compared to administration of the therapeutic macromolecule when not administered concomitantly with the immunosuppressant dose, and each in the presence of an anti-therapeutic macromolecule antibody response. In another embodiment of any one of the methods provided, the reduced pharmacodynamically effective dose of the therapeutic macromolecule is less than a pharmacodynamically effective dose of the therapeutic macromolecule that: (A) is administered in the presence of an anti-therapeutic macromolecule antibody response, and (B) is not administered concomitantly with the immunosuppressant dose.

In another aspect a method comprising providing an immunosuppressant dose, wherein in some embodiments the immunosuppressant dose is attached to synthetic nanocarriers, and administering a pharmacodynamically effective dose of a therapeutic macromolecule concomitantly with the immunosuppressant dose is provided. In one embodiment, the concomitant administration is according to a protocol that has been demonstrated to enhance a pharmacodynamic effect of the therapeutic macromolecule upon concomitant administration with the immunosuppressant dose, as compared to administration of the therapeutic macromolecule when not administered concomitantly with the immunosuppressant dose, and each in the presence of an anti-therapeutic macromolecule antibody response.

In another aspect, a method comprising providing an immunosuppressant dose, wherein in some embodiments the immunosuppressant dose is attached to synthetic nanocarriers, administering a pharmacodynamically effective dose of a therapeutic macromolecule concomitantly with the immunosuppressant dose, and recording an enhanced pharmacodynamic effect following the concomitant administration is provided.

In another aspect, a method comprising providing therapeutic macromolecules that cause or are expected to cause anti-therapeutic macromolecule antibodies upon repeated dosing in one or more subjects; and providing an immunosuppressant dose, wherein the immunosuppressant dose is attached to synthetic nanocarriers. In some embodiments, the method comprises repeatedly dosing at the same or a lower dose a subject with the therapeutic macromolecules concomitantly with the immunosuppressant dose. In some embodiments, the concomitant administration is according to a protocol that has been demonstrated to result in maintenance of a pharmacodynamic effect of the therapeutic macromolecule over two or more doses of the therapeutic macromolecule to a subject.

In one embodiment of any one of the methods provided, the method further comprises determining the protocol. In another embodiment of any one of the methods provided, the method further comprises determining the pharmacodynamically effective dose, such as the reduced or enhanced pharmacodynamically effective dose. In another embodiment of any one of the methods provided, the method further comprises assessing the pharmacodynamic effect in the subject prior to and/or after the administration. In another embodiment of any one of the methods provided, the concomitant administration is repeated one or more times. In another embodiment of any one of the methods provided, the administering is by intravenous, intraperitoneal or subcutaneous administration. In another embodiment of any one of the methods provided, the subject is at risk of an anti-therapeutic macromolecule antibody response. In another embodiment of any one of the methods provided, this subject is one in which the anti-therapeutic macromolecule response is expected to occur.

In another aspect, a composition or kit comprising an immunosuppressant dose wherein, in some embodiments, the immunosuppressant is attached to synthetic nanocarriers, and a reduced pharmacodynamically effective dose of a therapeutic macromolecule is provided.

In another aspect, a composition or kit comprising a reduced pharmacodynamically effective dose of a therapeutic macromolecule for use in any one of the methods provided herein is provided in combination with an immunosuppressant dose wherein in some embodiments the immunosuppressant is attached to synthetic nanocarriers.

In one embodiment of any one of the compositions or kits provided, the composition or kit is for use in any one of the methods provided herein. In one embodiment of any one of the compositions or kits provided, the composition or kit further comprises a pharmaceutically acceptable carrier.

In one embodiment of any one of the methods or compositions or kits provided, the therapeutic macromolecule is not attached to the synthetic nanocarriers. In another embodiment of any one of the methods or compositions or kits provided, the therapeutic macromolecule is attached to the synthetic nanocarriers. In another embodiment of any one of the methods or compositions or kits provided, the synthetic nanocarriers do not comprise therapeutic macromolecule APC presentable antigens.

In one embodiment of any one of the compositions or kits provided, the immunosuppressant dose and the therapeutic macromolecule are each contained in a container. In another embodiment of any one of the compositions or kits provided, the immunosuppressant dose and the therapeutic macromolecule are contained in separate containers. In another embodiment of any one of the compositions or kits provided, the immunosuppressant dose and the therapeutic macromolecule are contained in the same container.

In one embodiment of any one of the methods or compositions or kits provided, the reduced pharmacodynamically effective dose of the therapeutic macromolecule is at least 30% less than a pharmacodynamically effective dose of the therapeutic macromolecule that (A) is administered in the presence of an anti-therapeutic macromolecule antibody response, and (B) is not administered concomitantly with the immunosuppressant dose. In another embodiment of any one of the methods or compositions or kits provided, the reduced pharmacodynamically effective dose is at least 40% less. In another embodiment of any one of the methods or compositions or kits provided, the reduced pharmacodynamically effective dose is at least 50% less.

In one embodiment of any one of the methods or compositions or kits provided, the immunosuppressant dose comprises a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterase 4 inhibitor, an HDAC inhibitor or a proteasome inhibitor. In another embodiment of any one of the methods or compositions or kits provided, the mTOR inhibitor is rapamycin.

In one embodiment of any one of the methods or compositions or kits provided, the therapeutic macromolecule comprises a therapeutic protein. In another embodiment of any one of the methods or compositions or kits provided, the therapeutic macromolecule comprises a therapeutic polynucleotide. In another embodiment of any one of the methods or compositions or kits provided, the therapeutic protein is for protein replacement or protein supplementation therapy. In another embodiment of any one of the methods or compositions or kits provided, the therapeutic macromolecule comprises a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease. In another embodiment of any one of the methods or compositions or kits provided, the infusible or injectable therapeutic protein comprises Tocilizumab, alpha-1 antitrypsin, Hematide, albinterferon alfa-2b, Rhucin, tesamorelin, ocrelizumab, belimumab, pegloticase, pegsiticase, taliglucerase alfa, agalsidase alfa or velaglucerase alfa. In another embodiment of any one of the methods or compositions or kits provided, the enzyme comprises an oxidoreductase, transferase, hydrolase, lyase, isomerase or ligase. In another embodiment of any one of the methods or compositions or kits provided, the enzyme comprises an enzyme for enzyme replacement therapy for a lysosomal storage disorder. In another embodiment of any one of the methods or compositions or kits provided, the enzyme for enzyme replacement therapy for a lysosomal storage disorder comprises imiglucerase, a-galactosidase A (a-gal A), agalsidase beta, acid α-glucosidase (GAA), alglucosidase alfa, LUMIZYME, MYOZYME, arylsulfatase B, laronidase, ALDURAZYME, idursulfase, ELAPRASE, arylsulfatase B or NAGLAZYME. In another embodiment of any one of the methods or compositions or kits provided, the enzymes comprise KRYSTEXXA (pegloticase). In another embodiment of any one of the methods or compositions or kits provided, the monoclonal antibody comprises HUMIRA (adalimumab). In another embodiment of any one of the methods or compositions or kits provided, the cytokine comprises a lymphokine, interleukin, chemokine, type 1 cytokine or a type 2 cytokine. In another embodiment of any one of the methods or compositions or kits provided, the blood or blood coagulation factor comprises Factor I, Factor II, tissue factor, Factor V, Factor VII, Factor VIII, Factor IX, Factor X, Factor Xa, Factor XII, Factor XIII, von Willebrand factor, prekallikrein, high-molecular weight kininogen, fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant or epoetin alfa. In another embodiment of any one of the methods or compositions or kits provided, the blood or blood coagulation factor is Factor VIII.

In one embodiment of any one of the methods or compositions or kits provided, a load of immunosuppressant attached to the synthetic nanocarriers, on average across the synthetic nanocarriers, is between 0.1% and 50%. In another embodiment of any one of the methods or compositions or kits provided, the load is between 0.1% and 20%.

In one embodiment of any one of the methods or compositions or kits provided, the synthetic nanocarriers comprise lipid nanoparticles, polymeric nanoparticles, metallic nanoparticles, surfactant-based emulsions, dendrimers, buckyballs, nanowires, virus-like particles or peptide or protein particles. In another embodiment of any one of the methods or compositions or kits provided, the synthetic nanocarriers comprise lipid nanoparticles. In another embodiment of any one of the methods or compositions or kits provided, the synthetic nanocarriers comprise liposomes. In another embodiment of any one of the methods or compositions or kits provided, the synthetic nanocarriers comprise metallic nanoparticles. In another embodiment of any one of the methods or compositions or kits provided, the metallic nanoparticles comprise gold nanoparticles. In another embodiment of any one of the methods or compositions or kits provided, the synthetic nanocarriers comprise polymeric nanoparticles. In another embodiment of any one of the methods or compositions or kits provided, the polymeric nanoparticles comprise polymer that is a non-methoxy-terminated, pluronic polymer. In another embodiment of any one of the methods or compositions or kits provided, the polymeric nanoparticles comprise a polyester, polyester attached to a polyether, polyamino acid, polycarbonate, polyacetal, polyketal, polysaccharide, polyethyloxazoline or polyethyleneimine. In another embodiment of any one of the methods or compositions or kits provided, the polyester comprises a poly(lactic acid), poly(glycolic acid), poly(lactic-co-glycolic acid) or polycaprolactone. In another embodiment of any one of the methods or compositions or kits provided, the polymeric nanoparticles comprise a polyester and a polyester attached to a polyether. In another embodiment of any one of the methods or compositions or kits provided, the polyether comprises polyethylene glycol or polypropylene glycol.

In one embodiment of any one of the methods or compositions or kits provided, the mean of a particle size distribution obtained using dynamic light scattering of the synthetic nanocarriers is a diameter greater than 100 nm. In another embodiment of any one of the methods or compositions or kits provided, the diameter is greater than 150 nm. In another embodiment of any one of the methods or compositions or kits provided, the diameter is greater than 200 nm. In another embodiment of any one of the methods or compositions or kits provided, the diameter is greater than 250 nm. In another embodiment of any one of the methods or compositions or kits provided, the diameter is greater than 300 nm.

In one embodiment of any one of the methods or compositions or kits provided, an aspect ratio of the synthetic nanocarriers is greater than 1:1, 1:1.2, 1:1.5, 1:2, 1:3, 1:5, 1:7 or 1:10.

In another aspect, a method of manufacturing any one of the compositions or kits provided herein is provided. In one embodiment, the method of manufacturing comprises producing a dose or dosage form of a therapeutic macromolecule and producing a dose or dosage form of an immunosuppressant. In some embodiments, the dose or dosage form of a therapeutic macromolecule is a reduced pharmacodynamically effective dose of the therapeutic macromolecule. In another embodiment of any one of the methods of manufacturing provided, the step of producing a dose or dosage form of an immunosuppressant comprises attaching the immunosuppressant to synthetic nanocarriers. In another embodiment of any one of the methods of manufacturing provided, the method further comprises combining the dose or dosage form of the immunosuppressant and dose or dosage form of the therapeutic macromolecule in a kit.

In another aspect, a use of any of the compositions or kits provided herein for the manufacture of a medicament for reducing an anti-therapeutic macromolecule antibody response, in a subject is provided. In one embodiment, the composition or kit comprises an immunosuppressant and a therapeutic macromolecule, wherein the therapeutic macromolecule may be provided in a reduced pharmacodynamically effective dose of the therapeutic macromolecule. In another embodiment of any one of the uses provided herein, the immunosuppressant is attached to synthetic nanocarriers. In another embodiment of any one of the uses provided herein, the use if for achieving any one of the methods provided herein.

In another aspect, any one of the composition or kits provided herein may be for use in any one of the methods provided herein. In one embodiment, the composition or kit comprises a one or more doses or dosage forms of a therapeutic macromolecule and/or one or more doses or dosage forms of an immunosuppressant. In one embodiment, the doses of a therapeutic macromolecule are reduced pharmacodynamically effective dose. In another embodiment, the immunosuppressant is attached to synthetic nanocarriers.

In another aspect, a method of manufacturing a medicament intended for reducing an anti-therapeutic macromolecule antibody response, is provided. In one embodiment, the medicament comprises an immunosuppressant and/or a therapeutic macromolecule, wherein the therapeutic macromolecule may be at a reduced pharmacodynamically effective dose. In another embodiment of any one of the methods of manufacturing provided herein, the immunosuppressant is attached to synthetic nanocarriers.

DETAILED DESCRIPTION OF THE INVENTION

Figure 1:
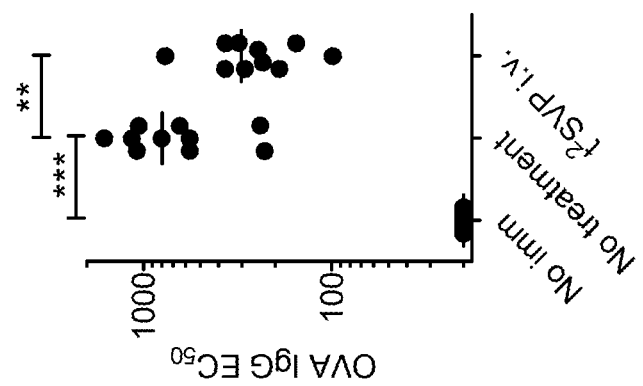
FIG. 1 shows the level of circulating antigen-specific antibody production with a concomitant administration as provided herein.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a RNA molecule" includes a mixture of two or more such RNA molecules or a plurality of such RNA molecules, reference to "an immunosuppressant" includes a mixture of two or more such materials or a plurality of such immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any one of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A. Introduction

The methods, composition or kits provided herein can be used to improve the pharmacodynamic effect(s) of a therapeutic macromolecule in a subject in which an antibody response against the therapeutic macromolecule has been mounted. Accordingly, the methods or compositions or kits provide herein can be used to improve the pharmacodynamics effect(s) of therapeutic macromolecules that are otherwise diminished because of an anti-therapeutic macromolecule antibody response. Without being bound by a particular theory, it is thought that undesirable humoral immune responses against therapeutic macromolecules can be reduced using the methods, compositions or kits provided. In some embodiments, the methods, compositions or kits can be used to tolerize a subject against a therapeutic macromolecule reducing undesirable immune responses that would otherwise result when the therapeutic macromolecule is administered without the concomitant administration of an immunosuppressant dose as provided, such dose may be repeatedly concomitantly administered. Such undesirable immune responses can result in the enhanced clearance of the therapeutic macromolecule, or other interference with the therapeutic activity of the therapeutic macromolecule. As a result of the reduced undesirable immune responses, therefore, the pharmacodynamic effect(s) of a therapeutic macromolecule can be enhanced and/or reduced dosage amounts of the therapeutic macromolecule can be used to achieve the same level of effect with the methods, compositions or kits provided. As another result of the reduced undesirable immune responses, therefore, repeated dosings of a therapeutic macromolecule can be administered to a subject.

It has been unexpectedly and surprisingly found that delivering immunosuppressants, preferably in some embodiments when attached to synthetic nanocarriers, concomitantly with therapeutic macromolecules, and in the presence of an anti-therapeutic macromolecule antibody response, can result in enhanced pharmacodynamic effects. For example, the aforementioned combinations can help neutralize anti-therapeutic macromolecule-specific antibodies that interfere with the desired treatment effects of a therapeutic macromolecule. The methods, compositions or kits provided herein, in some embodiments, not only reduce the undesired immune responses against the therapeutic macromolecule but also result in the enhancement of the desired therapeutic effect of the therapeutic macromolecule that would otherwise be diminished when the therapeutic macromolecule is administered alone (as a result of an undesirable immune response to that therapeutic macromolecule). Thus, methods, compositions or kits provided herein can allow for a subject to obtain the treatment benefit of a therapeutic macromolecule without needing to increase the dose of the therapeutic macromolecule, which generally would be increased in order to compensate for undesired immune responses against the therapeutic macromolecule when administered without the benefit of the invention provided herein. Surprisingly, the methods, compositions or kits provided herein even allow for a subject to be administered reduced doses of the therapeutic macromolecule to achieve the same therapeutic benefit.

As undesired immune responses that are generated during therapeutic treatment with therapeutic macromolecules can be counteracted with the methods, compositions or kits provided, the invention is useful for achieving enhanced pharmacodynamic effects, or for using a reduced pharmacodynamically effective doses, in subjects in which undesired immune responses against the therapeutic macromolecule are generated or are expected to be generated. In one embodiment of any one of the methods provided herein, the subject can be one at risk for such an undesired immune response.

The invention will now be described in more detail below.

B. Definitions

"Administering" or "administration" or "administer" means providing a material to a subject in a manner that is pharmacologically useful. The term is intended to include causing to be administered in some embodiments. "Causing to be administered" means causing, urging, encouraging, aiding, inducing or directing, directly or indirectly, another party to administer the material.

"Amount effective" in the context of a composition or dose for administration to a subject refers to an amount of the composition or dose that produces one or more desired responses in the subject, for example, the generation of a tolerogenic immune response (e.g., a reduction in the proliferation, activation, induction, survival, recruitment of therapeutic macromolecule-specific B cells or a reduction in the production of therapeutic macromolecule-specific antibodies). In some embodiments, the amount effective is a pharmacodynamically effective amount. Therefore, in some embodiments, an amount effective is any amount of a composition or dose provided herein (or multiple compositions or doses as provided herein) that produces one or more of the desired pharmacodynamic effects, therapeutic effects and/or immune responses as provided herein. This amount can be for in vitro or in vivo purposes. For in vivo purposes, the amount can be one that a clinician would believe may have a clinical benefit for a subject in need of therapeutic macromolecule administration and/or antigen-specific immune tolerance thereto.

Amounts effective can involve reducing the level of an undesired immune response, although in some embodiments, it involves preventing an undesired immune response altogether. Amounts effective can also involve delaying the occurrence of an undesired immune response. An amount that is effective can also be an amount that produces a desired therapeutic endpoint or a desired therapeutic result. In other embodiments, the amounts effective can involve enhancing the level of a desired response, such as a therapeutic endpoint or result. Amounts effective, preferably, result in a tolerogenic immune response in a subject to an antigen, such as a therapeutic macromolecule. The achievement of any of the foregoing can be monitored by routine methods.

In some embodiments of any one of the methods provided, the amount effective is one in which the desired response persists in the subject for at least 1 week, at least 2 weeks, at least 1 month, at least 2 months, at least 3 months, at least 4 months, at least 5 months, or longer. In other embodiments of any of the compositions and methods provided, the amount effective is one which produces a measurable desired response for at least 1 week, at least 2 weeks, at least 1 month, at least 2 months, at least 3 months, at least 4 months, at least 5 months, or longer.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the immunosuppressants and/or therapeutic macromolecules in the compositions of the invention refer to the amount of the immunosuppressants and/or therapeutic macromolecules. Alternatively, the dose can be administered based on the number of synthetic nanocarriers that provide the desired amount of immunosuppressants and/or therapeutic macromolecules.

"Anti-therapeutic macromolecule antibody response" or "anti-therapeutic macromolecule-specific antibody response" is the generation of anti-therapeutic macromolecule-specific antibodies, or induction of the process for producing such antibodies, as a result of administration of a therapeutic macromolecule. In embodiments, such a response counteracts the therapeutic effects of the therapeutic macromolecule.

"Antigen" means a B cell antigen or T cell antigen. "Type(s) of antigens" means molecules that share the same, or substantially the same, antigenic characteristics. In some embodiments, antigens may be proteins, polypeptides, peptides, lipoproteins, glycolipids, polynucleotides, polysaccharides or are contained or expressed in cells. In some embodiments, such as when the antigens are not well defined or characterized, the antigens may be contained within a cell or tissue preparation, cell debris, cell exosomes, conditioned media, etc.

"Antigen-specific" refers to any immune response that results from the presence of the antigen, or portion thereof, or that generates molecules that specifically recognize or bind the antigen. In some embodiments, when the antigen comprises the therapeutic macromolecule, antigen-specific may mean therapeutic macromolecule-specific. For example, where the immune response is antigen-specific antibody production, such as therapeutic macromolecule-specific antibody production, antibodies are produced that specifically bind the antigen (e.g., therapeutic macromolecule). As another example, where the immune response is antigen-specific B cell or CD4+ T cell proliferation and/or activity, the proliferation and/or activity results from recognition of the antigen, or portion thereof, alone or in complex with MHC molecules, B cells, etc.

"Assessing a pharmacodynamic effect" refers to any measurement or determination of the level, presence or absence, reduction, increase in, etc. of a pharmacodynamic effect in vitro or in vivo. Such measurements or determinations may be performed on one or more samples obtained from a subject. Such assessing can be performed in any one of the methods provided herein or otherwise known in the art.

An "at risk" subject is one in which a health practitioner believes has a chance of having a disease, disorder or condition or is one a health practitioner believes has a chance of experiencing an undesired anti-therapeutic macromolecule antibody response as provided herein and would benefit from the compositions and methods provided. In an embodiment of any one of the methods, compositions or kits provided herein the subject is one that is at risk of having an anti-therapeutic macromolecule antibody response to a therapeutic macromolecule. In another embodiment of any one of the methods, compositions or kits provided herein, the subject is one that is expected to have an anti-therapeutic macromolecule antibody response to a therapeutic macromolecule.

"Attach" or "Attached" or "Couple" or "Coupled" (and the like) means to chemically associate one entity (for example a moiety) with another. In some embodiments, the attaching is covalent, meaning that the attachment occurs in the context of the presence of a covalent bond between the two entities. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of attaching.

In embodiments, therapeutic macromolecules and immunosuppressants are not attached to one another, meaning that the therapeutic macromolecules and immunosuppressants are not subjected to a process specifically intended to chemically associate one with another. In embodiments, therapeutic macromolecules and/or immunosuppressants are not attached to synthetic nanocarriers, meaning that the therapeutic macromolecules (and/or immunosuppressants) and synthetic nanocarriers are not subjected to a process specifically intended to chemically associate one with another.

"Average", as used herein, refers to the arithmetic mean unless otherwise noted.

"Combination", as applied to two or more materials and/or agents (also referred to herein as the components), is intended to define material in which the two or more materials/agents are associated. Components may be separately identified, e.g., first component, second component, third component, etc. The terms "combined" and "combining" in this context are to be interpreted accordingly.

The association of the two or more materials/agents in a combination may be physical or non-physical. Examples of physically associated combined materials/agents include:
  compositions (e.g., unitary formulations) comprising the two or more materials/agents in admixture (for example within the same unit dose);
  compositions comprising material in which the two or more materials/agents are chemically/physicochemically linked (for example by crosslinking, molecular agglomeration or binding to a common vehicle moiety);
  compositions comprising material in which the two or more materials/agents are chemically/physicochemically co-packaged (for example, disposed on or within lipid vesicles, particles (e.g., micro- or nanoparticles) or emulsion droplets);
  pharmaceutical kits, pharmaceutical packs or patient packs in which the two or more materials/agents are co-packaged or co-presented (e.g., as part of an array of unit doses);
Examples of non-physically associated combined materials/agents include:
  material (e.g., a non-unitary formulation) comprising at least one of the two or more materials/agents together with instructions for the extemporaneous association of the at least one compound/agent to form a physical association of the two or more materials/agents;
  material (e.g., a non-unitary formulation) comprising at least one of the two or more materials/agents together with instructions for combination therapy with the two or more materials/agents;
  material comprising at least one of the two or more materials/agents together with instructions for administration to a patient population in which the other(s) of the two or more materials/agents have been (or are being) administered;
  material comprising at least one of the two or more materials/agents in an amount or in a form which is specifically adapted for use in combination with the other(s) of the two or more materials/agents.

As used herein, the term "combination therapy" is intended to define therapies which comprise the use of a combination of two or more materials/agents (as defined above). Thus, references to "combination therapy", "combinations" and the use of materials/agents "in combination" in this application may refer to materials/agents that are administered as part of the same overall treatment regimen. As such, the posology of each of the two or more materials/agents may differ: each may be administered at the same time or at different times. It will, therefore, be appreciated that the materials/agents of the combination may be administered sequentially (e.g., before or after) or simultaneously, either in the same pharmaceutical formulation (i.e., together), or in different pharmaceutical formulations (i.e., separately). Simultaneously in the same formulation is as a unitary formulation whereas simultaneously in different pharmaceutical formulations is non-unitary. The posologies of each of the two or more materials/agents in a combination therapy may also differ with respect to the route of administration.

"Concomitantly" means administering two or more materials/agents to a subject in a manner that is correlated in time, preferably sufficiently correlated in time so as to provide a modulation in a physiologic or immunologic response, and even more preferably the two or more materials/agents are administered in combination. In embodiments, concomitant administration may encompass administration of two or more materials/agents within a specified period of time, preferably within 1 month, more preferably within 1 week, still more preferably within 1 day, and even more preferably within 1 hour. In embodiments, the materials/agents may be repeatedly administered concomitantly, that is concomitant administration on more than one occasion, such as may be provided in the Examples.

"Determining" or "determine" means to ascertain a factual relationship. Determining may be accomplished in a number of ways, including but not limited to performing experiments, or making projections. For instance, a dose of an immunosuppressant or therapeutic macromolecule may be determined by starting with a test dose and using known scaling techniques (such as allometric or isometric scaling) to determine the dose for administration. Such may also be used to determine a protocol as provided herein. In another embodiment, the dose may be determined by testing various doses in a subject, i.e. through direct experimentation based on experience and guiding data. In embodiments, "determining" or "determine" comprises "causing to be determined." "Causing to be determined" means causing, urging, encouraging, aiding, inducing or directing or acting in coordination with an entity for the entity to ascertain a factual relationship; including directly or indirectly, or expressly or impliedly.

"Dosage form" means a pharmacologically and/or immunologically active material in a medium, carrier, vehicle, or device suitable for administration to a subject. Any one of the compositions or doses provided herein may be in a dosage form.

"Dose" refers to a specific quantity of a pharmacologically and/or immunologically active material for administration to a subject for a given time.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Generating" means causing an action, such as a physiologic or immunologic response (e.g., tolerogenic immune response) to occur, either directly oneself or indirectly.

"Identifying a subject" is any action or set of actions that allows a clinician to recognize a subject as one who may benefit from the methods, compositions or kits provided herein. Preferably, the identified subject is one who is in need of a therapeutic benefit from a therapeutic macromolecule as provided herein and in which an anti-therapeutic macromolecule-specific antibody response has occurred or is suspected to occur. The action or set of actions may be either directly oneself or indirectly. In one embodiment of any one of the methods provided herein, the method further comprises identifying a subject in need of a method, composition or kit as provided herein.

"Immunosuppressant" means a compound that causes an APC to have an immunosuppressive effect or a T cell or B cell to be suppressed (e.g., tolerogenic effect). An immunosuppressive effect generally refers to the production or expression of cytokines or other factors by the APC that reduces, inhibits or prevents an undesired immune response or that promotes a desired immune response, such as a regulatory immune response. When the APC acquires an immunosuppressive function (under the immunosuppressive effect) on immune cells that recognize an antigen presented by this APC, the immunosuppressive effect is said to be specific to the presented antigen. Without being bound by any particular theory, it is thought that the immunosuppressive effect is a result of the immunosuppressant being delivered to the APC, preferably in the presence of an antigen. In one embodiment, the immunosuppressant is one that causes an APC to promote a regulatory phenotype in one or more immune effector cells. For example, the regulatory phenotype may be characterized by the inhibition of the production, induction, stimulation or recruitment of antigen-specific CD4+ T cells or B cells, the inhibition of the production of antigen-specific antibodies, the production, induction, stimulation or recruitment of Treg cells (e.g., CD4+CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol, methotrexate and triptolide. In embodiments, the immunosuppressant may comprise any of the agents provided herein.

The immunosuppressant can be a compound that directly provides the immunosuppressive effect on APCs or it can be a compound that provides the immunosuppressive effect indirectly (i.e., after being processed in some way after administration). Immunosuppressants, therefore, include prodrug forms of any of the compounds provided herein.

In embodiments of any one of the methods, compositions or kits provided herein, the immunosuppressants provided herein are attached to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and attached to the one or more polymers. As another example, in one embodiment, where the synthetic nanocarrier is made up of one or more lipids, the immunosuppressant is again in addition and attached to the one or more lipids. In embodiments, such as where the material of the synthetic nanocarrier also results in an immunosuppressive effect, the immunosuppressant is an element present in addition to the material of the synthetic nanocarrier that results in an immunosuppressive effect.

Other exemplary immunosuppressants include, but are not limited, small molecule drugs, natural products, antibodies (e.g., antibodies against CD20, CD3, CD4), biologics-based drugs, carbohydrate-based drugs, nanoparticles, liposomes, RNAi, antisense nucleic acids, aptamers, methotrexate, NSAIDs; fingolimod; natalizumab; alemtuzumab; anti-CD3; tacrolimus (FK506); cytokines and growth factors, such as TGF-β and IL-10; etc. Further immunosuppressants, are known to those of skill in the art, and the invention is not limited in this respect.

In embodiments of any one of the methods, compositions or kits provided herein, the immunosuppressant is in a form, such as a nanocrystalline form, whereby the form of the immunosuppressant itself is a particle or particle-like. In embodiments, such forms mimic a virus or other foreign pathogen. Many drugs have been nanonized and appropriate methods for producing such drug forms would be known to one of ordinary skill in the art. Drug nanocrystals, such as nanocrystalline rapamycin are known to those of ordinary skill in the art (Katteboinaa, et al. 2009, International Journal of PharmTech Research; Vol. 1, No. 3; pp 682-694. As used herein a "drug nanocrystal" refers to a form of a drug (e.g., an immunosuppressant) that does not include a carrier or matrix material. In some embodiments, drug nanocrystals comprise 90%, 95%, 98%, or 99% or more drug. Methods for producing drug nanocrystals include, without limitation, milling, high pressure homogenization, precipitation, spray drying, rapid expansion of supercritical solution (RESS), Nanoedge® technology (Baxter Healthcare), and Nanocrystal Technology™ (Elan Corporation). In some embodiments, a surfactant or a stabilizer may be used for steric or electrostatic stability of the drug nanocrystal. In some embodiments the nanocrystal or nanocrystalline form of an immunosuppressant may be used to increase the solubility, stability, and/or bioavailability of the immunosuppressant, particularly immunosuppressants that are insoluble or labile. In some embodiments, concomitant administration of a reduced pharmacodynamically effective dose of a therapeutic macromolecule with an immunosuppressant in nanocrystalline form results in a reduced anti-therapeutic macromolecule antibody response.

"Load", when attached to a synthetic nanocarrier, is the amount of the immunosuppressant and/or therapeutic macromolecule attached to a synthetic nanocarrier based on the total dry recipe weight of materials in an entire synthetic nanocarrier (weight/weight). Generally, the load is calculated as an average across a population of synthetic nanocarriers. In one embodiment, the load on average across the synthetic nanocarriers is between 0.1% and 99%. In another embodiment, the load is between 0.1% and 50%. In another embodiment, the load of the immunosuppressant and/or therapeutic macromolecule is between 0.1% and 20%. In a further embodiment, the load of the immunosuppressant and/or therapeutic macromolecule is between 0.1% and 10%. In still a further embodiment, the load of the immunosuppressant and/or therapeutic macromolecule is between 1% and 10%. In still a further embodiment, the load of the immunosuppressant is between 7% and 20%. In yet another embodiment, the load of the immunosuppressant and/or the therapeutic macromolecule is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least at least 7%, at least 8%, at least 9%, at least 10%, at least 11%, at least 12%, at least 13%, at least 14%, at least 15%, at least 16%, at least 17%, at least 18%, at least 19% at least 20%, at least 25%, at least 30%, at least 40%, at least 50%, at least 60%, at least 70%, at least 80%, at least 90%, at least 95%, at least 96%, at least 97%, at least 98% or at least 99% on average across the population of synthetic nanocarriers. In yet a further embodiment, the load of the immunosuppressant and/or the therapeutic macromolecule is 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% on average across the population of synthetic nanocarriers. In some embodiments of the above embodiments, the load of the immunosuppressant and/or the therapeutic macromolecule is no more than 25% on average across a population of synthetic nanocarriers. In embodiments, the load is calculated as may be described in the Examples or as otherwise known in the art.

In some embodiments, when the form of the immunosuppressant is itself a particle or particle-like, such as a nanocrystalline immunosuppressant, the load of immunosuppressant is the amount of the immunosuppressant in the particles or the like (weight/weight). In such embodiments, the load can approach 97%, 98%, 99% or more.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 μm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., effective diameter) may be obtained, in some embodiments, by suspending the synthetic nanocarriers in a liquid (usually aqueous) media and using dynamic light scattering (DLS) (e.g., using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indices of the sample. The effective diameter, or mean of the distribution, is then reported. Determining the effective sizes of high aspect ratio, or non-spheroidal, synthetic nanocarriers may require augmentative techniques, such as electron microscopy, to obtain more accurate measurements. "Dimension" or "size" or "diameter" of synthetic nanocarriers means the mean of a particle size distribution, for example, obtained using dynamic light scattering.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Pharmaceutically acceptable excipient" or "pharmaceutically acceptable carrier" means a pharmacologically inactive material used together with a pharmacologically active material to formulate the compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Pharmacodynamic effect" of "pharmacodynamic response" means any physiologic or immunologic response as a result of the administration of a therapeutic macromolecule. Such a response can be a desired response such as one that is associated with a therapeutic effect. The methods, compositions or kits provided herein, in some embodiments, have been found to result in enhanced pharmacodynamic effects such as enhanced therapeutic effects, when administered in the presence of an anti-therapeutic macromolecule antibody response. In some instances, the enhanced pharmacodynamics effects can be obtained with a dose of the therapeutic macromolecule that is the same as or less than a dose of the therapeutic macromolecule when administered without the concomitant administration of an immunosuppressant dose as provided herein in the presence of an anti-therapeutic macromolecule antibody response. Whether a material/agent is pharmacodynamically effective can be evaluated by standard methods. In some embodiments, a pharmacodynamic effect using a method, composition or kit provided, in the presence of an anti-therapeutic macromolecule antibody response, is compared to the pharmacodynamic effect when a therapeutic macromolecule is not so administered but also in the presence of an anti-therapeutic macromolecule antibody response. In embodiments, the comparison is to the pharmacodynamic effect when the therapeutic macromolecule is administered alone in the presence of an anti-therapeutic macromolecule antibody response. Generally, a pharmacodynamic effect is assessed with administration in the presence of an anti-therapeutic macromolecule antibody response, as it is desired that a method, composition or kit is effective to overcome such a response. Accordingly, pharmacodynamic effects are determined when such a response is occurring.

"Protocol" means a pattern of administering to a subject and includes any dosing regimen of one or more substances to a subject. Protocols are made up of elements (or variables); thus a protocol comprises one or more elements. Such elements of the protocol can comprise dosing amounts, dosing frequency, routes of administration, dosing duration, dosing rates, interval between dosing, combinations of any of the foregoing, and the like. In some embodiments, such a protocol may be used to administer one or more compositions of the invention to one or more test subjects. Immune responses in these test subjects can then be assessed to determine whether or not the protocol was effective in generating a desired or desired level of a pharmacodynamic effect. Any other therapeutic and/or immunologic effect may also be assessed instead of or in addition to the aforementioned immune responses. One or more of the elements of a protocol may have been previously demonstrated in test subjects, such as non-human subjects, and then translated into human protocols. For example, dosing amounts demonstrated in non-human subjects can be scaled as an element of a human protocol using established techniques such as alimetric scaling or other scaling methods. Whether or not a protocol had a desired effect can be determined using any of the methods provided herein or otherwise known in the art. For example, a sample may be obtained from a subject to which a composition provided herein has been administered according to a specific protocol in order to determine whether or not specific immune cells, cytokines, antibodies, etc. were reduced, generated, activated, etc. Useful methods for detecting the presence and/or number of immune cells include, but are not limited to, flow cytometric methods (e.g., FACS), ELISpot, proliferation responses, cytokine production, and immunohistochemistry methods. Antibodies and other binding agents for specific staining of immune cell markers, are commercially available. Such kits typically include staining reagents for antigens that allow for FACS-based detection, separation and/or quantitation of a desired cell population from a heterogeneous population of cells. In embodiments, a number of compositions as provided herein are administered to another subject using one or more or all or substantially all of the elements of which the protocol is comprised. In some embodiments, the protocol has been demonstrated to result in a reduction of an antibody response against a therapeutic macromolecule and/or improved pharmacodynamic effect.

"Providing" means an action or set of actions that an individual performs that supply a needed item or set of items or methods for practicing of the present invention. The action or set of actions may be taken either directly oneself or indirectly.

"Providing a subject" is any action or set of actions that causes a clinician to come in contact with a subject and administer a composition provided herein thereto or to perform a method provided herein thereupon. Preferably, the subject is one who is in need of therapeutic macromolecule administration and antigen-specific immune tolerance thereto. The action or set of actions may be taken either directly oneself or indirectly. In one embodiment of any one of the methods provided herein, the method further comprises providing a subject.

"Recording an enhanced pharmacodynamic effect" means noting, or causing directly or indirectly activities in the expectation that such noting would take place, in any written or electronic form, that a therapeutic macromolecule dose achieved an enhanced pharmacodynamic effect in the presence of a real, expected or suspected anti-therapeutic macromolecule antibody response. Generally, in such circumstances the therapeutic macromolecule dose would not have been expected to achieve the enhanced pharmacodynamic effect in the presence of an anti-therapeutic macromolecule antibody response if administered without an immunosuppressant dose as provided herein (e.g., administered alone) based on information available at the time of concomitant administration as provided herein. For example, in such circumstances, it would be expected that the effectiveness of the therapeutic macromolecule would be diminished if administered without an immunosuppressant dose, but an enhanced pharmacodynamic effect is instead observed with a concomitant administration as provided herein. In some embodiments, the recording occurs when an immunosuppressant dose in combination with a therapeutic macromolecule dose are administered to a subject or at some point thereafter. In some of these embodiments, the dose of the therapeutic macromolecule is reduced as compared to (or no greater than) a dose of therapeutic macromolecule that is administered without the immunosuppressant dose in the presence of an anti-therapeutic macromolecule antibody response. "Written form", as used herein, refers to any recordation on a medium such as paper. "Electronic form", as used herein, refers to any recordation on electronic media. Any one of the methods provided herein can further comprise a step of recording a therapeutic and/or immune response in a subject receiving a treatment according to a method provided herein.

"Reduced pharmacodynamically effective dose" refers to a reduced amount of a therapeutic macromolecule that can achieve a similar pharmacodynamic effect when administered concomitantly with an immunosuppressant dose as provided herein as compared to the amount of the therapeutic macromolecule when not administered with the immunosuppressant dose (e.g., when the therapeutic macromolecule is administered alone). As used herein, a similar pharmacodynamic effect is a level of effect that is within one log of another level measured in the same way. Preferably, a similar pharmacodynamic effect is no more than 5-fold different. Still more preferably, a similar pharmacodynamic effect is no more than 2-fold different.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, synthetic nanocarriers do not comprise chitosan. In other embodiments, synthetic nanocarriers are not lipid-based nanoparticles. In further embodiments, synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid attached virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), (11) apoptotic cells, apoptotic bodies or the synthetic or semisynthetic mimics disclosed in U.S. Publication 2002/0086049, or (12) those of Look et al., Nanogel-based delivery of mycophenolic acid ameliorates systemic lupus erythematosus in mice" J. Clinical Investigation 123(4):1741-1749 (2013). In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

A "therapeutic macromolecule" refers to any protein, carbohydrate, lipid or nucleic acid that may be administered to a subject and have a therapeutic effect. In some embodiments, administration of the therapeutic macromolecule to a subject may result in an undesired immune response, including production of anti-therapeutic macromolecule-specific antibodies. As described herein, administration of a therapeutic macromolecule concomitantly with an immunosuppressant dose can enhance the therapeutic effectiveness of the therapeutic macromolecule, such as by reducing undesired immune responses thereto. In some embodiments, the therapeutic macromolecule may be a therapeutic polynucleotide or therapeutic protein.

"Therapeutic polynucleotide" means any polynucleotide or polynucleotide-based therapy that may be administered to a subject and have a therapeutic effect. Such therapies include gene silencing. Examples of such therapy are known in the art, and include, but are not limited to, naked RNA (including messenger RNA, modified messenger RNA, and forms of RNAi). Examples of other therapeutic polynucleotides are provided elsewhere herein. Therapeutic polynucleotides may be produced in, on or by cells and also may be obtained using cell free or from fully synthetic in vitro methods. Subjects, therefore, include any subject that is in need of treatment with any of the foregoing. Such subject include those that will receive any of the foregoing.

"Therapeutic protein" means any protein or protein-based therapy that may be administered to a subject and have a therapeutic effect. Such therapies include protein replacement and protein supplementation therapies. Such therapies also include the administration of exogenous or foreign proteins, antibody therapies, and cell or cell-based therapies. Therapeutic proteins comprise, but are not limited to, enzymes, enzyme cofactors, hormones, blood clotting factors, cytokines, growth factors, monoclonal antibodies, antibody-drug conjugates, and polyclonal antibodies. Examples of other therapeutic proteins are provided elsewhere herein. Therapeutic proteins may be produced in, on or by cells and may be obtained from such cells or administered in the form of such cells. In embodiments, the therapeutic protein is produced in, on or by mammalian cells, insect cells, yeast cells, bacteria cells, plant cells, transgenic animal cells, transgenic plant cells, etc. The therapeutic protein may be recombinantly produced in such cells. The therapeutic protein may be produced in, on or by a virally transformed cell. Subjects, therefore, include any subject that is in need of treatment with any of the foregoing. Such subject include those that will receive any of the foregoing.

"Therapeutic macromolecule APC presentable antigen" means an antigen that is associated with a therapeutic macromolecule (i.e., the therapeutic macromolecule or a fragment thereof that can generate an immune response against the therapeutic macromolecule (e.g., the production of anti-therapeutic macromolecule-specific antibodies)). Generally, therapeutic macromolecule antigen-presenting cell (APC) presentable antigens can be presented for recognition by the immune system (e.g., cells of the immune system, such as presented by antigen presenting cells, including but not limited to dendritic cells, B cells or macrophages). The therapeutic macromolecule APC presentable antigen can be presented for recognition by, for example, T cells. Such antigens may be recognized by and trigger an immune response in a T cell via presentation of an epitope of the antigen bound to Class I or Class II major histocompatibility complex molecule (MHC). Therapeutic macromolecule APC presentable antigens generally include proteins, polypeptides, peptides, polynucleotides, lipoproteins, or are contained or expressed in, on or by cells. The therapeutic macromolecule antigens, in some embodiments, are attached to synthetic nanocarriers and comprise MHC Class I-restricted epitopes and/or MHC Class II-restricted epitopes and/or B cell epitopes. Preferably, one or more tolerogenic immune responses specific to the therapeutic macromolecule result with the methods, compositions or kits provided herein. In embodiments, populations of the synthetic nanocarriers comprise no added therapeutic macromolecule APC presentable antigens, meaning that no substantial amounts of therapeutic macromolecule APC presentable antigens are intentionally added to the synthetic nanocarriers during the manufacturing thereof.

"Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include antigen-specific antibody production, antigen-specific B cell proliferation and/or activity or antigen-specific CD4+ T cell proliferation and/or activity. Generally, these undesired immune responses can be specific to a therapeutic macromolecule and counteract the beneficial effects desired of administration with the therapeutic macromolecule. Thus, in some embodiments, the undesired immune response is an anti-therapeutic macromolecule antibody response.

C. Compositions and Related Methods

Provided herein are compositions comprising immunosuppressants and therapeutic macromolecules and related methods or kits. Such methods, compositions or kits are useful to enhance the pharmacodynamics effect of a therapeutic macromolecule in the presence of an anti-therapeutic macromolecule antibody response, such as through the reduction or inhibition of undesired immune responses specific to the therapeutic macromolecule that diminish the therapeutic benefit of the therapeutic macromolecule. Such methods, compositions or kits are also useful to allow for the repeated dosing of a therapeutic macromolecule. Thus, the methods, compositions or kits provided herein are useful for achieving or enhancing desired therapeutic effects of the therapeutic macromolecules. In some embodiments, such therapeutic effects can be achieved or enhanced at reduced pharmacodynamically effective doses. The methods, compositions or kits provided can be used for any subject in need of the therapeutic benefit of a therapeutic macromolecule.

As mentioned above, it was found that delivering immunosuppressants, preferably in some embodiments when attached to synthetic nanocarriers, concomitantly with therapeutic macromolecules in the presence of an anti-therapeutic macromolecule antibody response can result in enhanced pharmacodynamic effects, including an enhancement of such effects even at reduced doses of the therapeutic macromolecules. For example, the methods, compositions or kits can help neutralize anti-therapeutic macromolecule-specific antibodies that interfere with the desired treatment effects of a therapeutic macromolecule. The methods, compositions or kits provided herein can, therefore, result in an enhancement of a desired therapeutic effect of a therapeutic macromolecule that would otherwise be diminished when the therapeutic macromolecule is administered without the immunosuppressant dose (e.g., when the therapeutic macromolecule is administered alone). Thus, in some embodiments, the methods, compositions or kit provided herein allow for a subject to obtain the treatment benefit of a therapeutic macromolecule without needing to increase the dose of the therapeutic macromolecule, which generally would be increased in order to compensate for undesired immune responses against the therapeutic macromolecule when administered without the benefit of the invention provided herein. Surprisingly, the methods, compositions or kits provided herein even allow for a subject to be administered reduced doses of the therapeutic macromolecule to achieve the same or better therapeutic benefit in the presence of an anti-therapeutic macromolecule antibody response.

A variety of immunosuppressants may be used in the practice of the present invention, which preferably, are attached to synthetic nanocarriers. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size or shape so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g., a polymeric core) and the shell is a second layer (e.g., a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, gluconic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, various elements of the synthetic nanocarriers can be attached to the polymer.

The immunosuppressants and/or therapeutic macromolecules can be attached to the synthetic nanocarriers by any of a number of methods. Generally, the attaching can be a result of bonding between the immunosuppressants and/or therapeutic macromolecules and the synthetic nanocarriers. This bonding can result in the immunosuppressants and/or therapeutic macromolecules being attached to the surface of the synthetic nanocarriers and/or contained (encapsulated) within the synthetic nanocarriers. In some embodiments, however, the immunosuppressants and/or therapeutic macromolecules are encapsulated by the synthetic nanocarriers as a result of the structure of the synthetic nanocarriers rather than bonding to the synthetic nanocarriers. In preferable embodiments, the synthetic nanocarrier comprises a polymer as provided herein, and the immunosuppressants and/or therapeutic macromolecules are attached to the polymer.

When attaching occurs as a result of bonding between the immunosuppressants and/or therapeutic macromolecules and synthetic nanocarriers, the attaching may occur via a coupling moiety. A coupling moiety can be any moiety through which an immunosuppressant and/or therapeutic macromolecule is bonded to a synthetic nanocarrier. Such moieties include covalent bonds, such as an amide bond or ester bond, as well as separate molecules that bond (covalently or non-covalently) the immunosuppressant and/or therapeutic macromolecule to the synthetic nanocarrier. Such molecules include linkers or polymers or a unit thereof. For example, the coupling moiety can comprise a charged polymer to which an immunosuppressant and/or therapeutic macromolecule electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant or therapeutic macromolecule, can be covalently associated with one or more polymers of the polymeric matrix. In some embodiments, covalent association is mediated by a linker. In some embodiments, a component can be noncovalently associated with one or more polymers of the polymeric matrix. For example, in some embodiments, a component can be encapsulated within, surrounded by, and/or dispersed throughout a polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly(glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-co-polymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g., attached) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids. Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids. In embodiments, the synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that the synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers do not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

Compositions according to the invention can comprise elements in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, compositions, such as those comprising the synthetic nanocarriers are suspended in sterile saline solution for injection together with a preservative.

In embodiments, when preparing synthetic nanocarriers as carriers, methods for attaching components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to attach the component to the synthetic nanocarrier through the use of these surface groups rather than attaching the component to a polymer and then using this polymer conjugate in the construction of synthetic nanocarriers.

In certain embodiments, the attaching can be with a covalent linker. In embodiments, components according to the invention can be covalently attached to the external surface via a 1,2,3-triazole linker formed by the 1,3-dipolar cycloaddition reaction of azido groups on the surface of the nanocarrier with a component containing an alkyne group or by the 1,3-dipolar cycloaddition reaction of alkynes on the surface of the nanocarrier with a component containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent attaching may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component with the carboxylic acid group of a second component, such as the nanocarrier. The amide bond in the linker can be made using any of the conventional amide bond forming reactions with suitably protected amino acids and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group on a polymer or nanocarrier or a nanocarrier containing thiol/mercaptan groups with a component containing activated thiol group.

A triazole linker, specifically a 1,2,3-triazole of the form

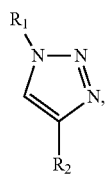

wherein R1 and R2 may be any chemical entities, is made by the 1,3-dipolar cycloaddition reaction of an azide attached to a first component, such as the nanocarrier, with a terminal alkyne attached to a second component, such as the immunosuppressant or therapeutic macromolecule. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently attaches the component to the particle through the 1,4-disubstituted 1,2,3-triazole linker.

A thioether linker is made by the formation of a sulfur-carbon (thioether) bond in the form, for instance, of R1-S—R2. Thioether can be made by either alkylation of a thiol/mercaptan (—SH) group on one component with an alkylating group such as halide or epoxide on a second component. Thioether linkers can also be formed by Michael addition of a thiol/mercaptan group on one component to an electron-deficient alkene group on a second component containing a maleimide group or vinyl sulfone group as the Michael acceptor. In another way, thioether linkers can be prepared by the radical thiol-ene reaction of a thiol/mercaptan group on one component with an alkene group on a second component.

A hydrazone linker is made by the reaction of a hydrazide group on one component with an aldehyde/ketone group on the second component.

A hydrazide linker is formed by the reaction of a hydrazine group on one component with a carboxylic acid group on the second component. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component.

An urea or thiourea linker is prepared by the reaction of an amine group on one component with an isocyanate or thioisocyanate group on the second component.

An amidine linker is prepared by the reaction of an amine group on one component with an imidoester group on the second component.

An amine linker is made by the alkylation reaction of an amine group on one component with an alkylating group such as halide, epoxide, or sulfonate ester group on the second component. Alternatively, an amine linker can also be made by reductive amination of an amine group on one component with an aldehyde or ketone group on the second component with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For example, a negative charged therapeutic macromolecule or immunosuppressant can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatable groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that is capable of attaching two molecules together. In an embodiment, the linker can be a homobifunctional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on nanocarrier to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be attached by adsorption to a pre-formed synthetic nanocarrier or it can be attached by encapsulation during the formation of the synthetic nanocarrier.

Any immunosuppressant as provided herein can be used in the methods or compositions provided and can be, in some embodiments, attached to synthetic nanocarriers. Immunosuppressants include, but are not limited to, statins; mTOR inhibitors, such as rapamycin or a rapamycin analog; TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, tripolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g., follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl) 1H-imidazole), SB-239063 (trans-1-(4hydroxycyclohexyl)-4-(fluorophenyl)-5-(2-methoxy-pyrimidin-4-yl) imidazole), SB-220025 (5-(2-amino-4-pyrimidinyl)-4-(4-fluorophenyl)-1-(4-piperidinyl)imidazole)), and ARRY-797.

Examples of NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), and wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfuram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, and mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, and T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, and sodium orthovanadate.

In some embodiments of any one of the methods, compositions or kits provided, the therapeutic macromolecules as described herein are also attached to synthetic nanocarriers. In other embodiments, the therapeutic macromolecules are not attached to any synthetic nanocarriers. In some embodiments of either of these situations, the therapeutic macromolecules may be delivered in the form of the therapeutic macromolecule itself, or fragments or derivatives thereof.

Therapeutic macromolecules can include therapeutic proteins or therapeutic polynucleotides. Therapeutic proteins include, but are not limited to, infusible therapeutic proteins, enzymes, enzyme cofactors, hormones, blood clotting factors, cytokines and interferons, growth factors, monoclonal antibodies, and polyclonal antibodies (e.g., that are administered to a subject as a replacement therapy), and proteins associated with Pompe's disease (e.g., acid glucosidase alfa, rhGAA (e.g., Myozyme and Lumizyme (Genzyme)). Therapeutic proteins also include proteins involved in the blood coagulation cascade. Therapeutic proteins include, but are not limited to, Factor VIII, Factor VII, Factor IX, Factor V, von Willebrand Factor, von Heldebrant Factor, tissue plasminogen activator, insulin, growth hormone, erythropoietin alfa, VEGF, thrombopoietin, lysozyme, antithrombin and the like. Therapeutic proteins also include adipokines, such as leptin and adiponectin. Other examples of therapeutic proteins are as described below and elsewhere herein.

Examples of therapeutic proteins used in enzyme replacement therapy of subjects having a lysosomal storage disorder include, but are not limited to, imiglucerase for the treatment of Gaucher's disease (e.g., CEREZYME™), a-galactosidase A (a-gal A) for the treatment of Fabry disease (e.g., agalsidase beta, FABRYZYME™), acid α-glucosidase (GAA) for the treatment of Pompe disease (e.g., acid glucosidase alfa, LUMIZYME™, MYOZYME™), arylsulfatase B for the treatment of Mucopolysaccharidoses (e.g., laronidase, ALDURAZYME™, idursulfase, ELAPRASE™, arylsulfatase B, NAGLAZYME™), pegloticase (KRYSTEXXA) and pegsiticase.

Examples of enzymes include oxidoreductases, transferases, hydrolases, lyases, isomerases, asparaginases, uricases, glycosidases, asparaginases, uricases, proteases, nucleases, collagenases, hyaluronidases, heparinases, heparanases, lysins, and ligases.

Therapeutic proteins may also include any enzyme, toxin, or other protein or peptide isolated or derived from a bacterial, fungal, or viral source.

Examples of hormones include Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood or blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, prekallikrein (Fletcher factor), high-molecular weight kininogen (HMWK) (Fitzgerald factor), fibronectin, fibrin, thrombin, antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumour_necrosis_factor-alpha (TNF-α), Vascular endothelial growth factor (VEGF), Wnt Signaling Pathway, placental growth factor (PlGF), (Foetal Bovine Somatotrophin) (FBS), IL-1, IL-2, IL-3, IL-4, IL-5, IL-6, and IL-7.

Examples of monoclonal antibodies include Abagovomab, Abciximab, Adalimumab, Adecatumumab, Afelimomab, Afutuzumab, Alacizumab pegol, ALD, Alemtuzumab, Altumomab pentetate, Anatumomab mafenatox, Anrukinzumab, Anti-thymocyte globin, Apolizumab, Arcitumomab, Aselizumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, Conatumumab, Dacetuzumab, Daclizumab, Daratumumab, Denosumab, Detumomab, Dorlimomab aritox, Dorlixizumab, Ecromeximab, Eculizumab, Edobacomab, Edrecolomab, Efalizumab, Efungumab, Elotuzumab, Elsilimomab, Enlimomab pegol, Epitumomab cituxetan, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab ozogamicin, GC1008, Girentuximab, Glembatumumab vedotin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Olaratumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, Rafivirumab, Ramucirumab, Ranibizumab, Raxibacumab, Regavirumab Reslizumab, Rilotumumab, Rituximab, Robatumumab, Rontalizumab, Rovelizumab, Ruplizumab, Satumomab pendetide, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, Ticilimumab (tremelimumab), Tigatuzumab, Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab aritox. Monoclonal antibodies further include anti-TNF-α antibodies.

Examples of infusion therapy or injectable therapeutic proteins include, for example, Tocilizumab (Roche/Actemra®), alpha-1 antitrypsin (Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), pegsiticase, taliglucerase alfa (Protalix/Uplyso), agalsidase alfa (Shire/Replagal®), velaglucerase alfa (Shire), and Keyhole Limpet Hemocyanin (KLH).

Additional therapeutic proteins include, for example, engineered proteins, such as Fc fusion proteins, bispecific antibodies, multi-specific antibodies, nanobodies, antigen-binding proteins, antibody fragments, and protein conjugates, such as antibody drug conjugates.

Therapeutic polynucleotides include, but are not limited to nucleic acid aptamers such as Pegaptanib (Macugen, a pegylated anti-VEGF aptamer), antisense therapeutics such as antisense poly- or oligonucleotides (e.g., antiviral drug Fomivirsen, or Mipomersen, an antisense therapeutic that targets the messenger RNA for apolipoprotein B for reduction of cholesterol level); small interfering RNAs (siRNAs) (e.g., dicer substrate siRNA molecules (DsiRNAs) which are 25-30 base pair asymmetric double-stranded RNAs that mediate RNAi with extremely high potency); or modified messenger RNAs (mmRNAs) such as those disclosed in US Patent application 2013/0115272 to de Fougerolles et al. and in Published US Patent application 2012/0251618 to Schrum et al.

Additional therapeutic macromolecules useful in accordance with aspects of this invention will be apparent to those of skill in the art, and the invention is not limited in this respect.

In some embodiments, a component, such as a therapeutic macromolecule or immunosuppressant may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein may be isolated and included in the compositions or used in the methods in isolated form.

D. Methods of Making and Using the Compositions and Related Methods

Aspects of the invention relate to determining a protocol for the methods of concomitant administration as provided herein. A protocol can be determined by varying the frequency, dosage amount and other aspects of administration of the therapeutic macromolecule and the immunosuppressant and subsequently assessing the pharmacodynamic effect based on such variation. The varied administration occurs in the presence of an anti-therapeutic macromolecule antibody response. A preferred protocol for practice of the invention induces a desired pharmacodynamic effect but induces little to no anti-therapeutic macromolecule antibody response.

In some aspects of the invention, a desired pharmacodynamic effect of a therapeutic macromolecule includes stimulating or inhibiting a specific response. In some embodiments, the pharmacodynamic effect involves, without limitation, production or degradation of a cytokine, chemokine, signaling molecule or other molecule; inducing proliferation or death of a particular cell type; maturation or localization of a particular cell type; interaction with an enzyme, structural protein, carrier protein, or receptor protein; modulation of activity of an enzyme, structural protein or receptor protein, etc. In some embodiments, the pharmacodynamic effect is reducing production of a cytokine, for example an inflammation-associated cytokine such as TNF, IL-1. In some embodiments, the pharmacodynamic effect is reducing the activity of a cytokine. In some embodiments, the pharmacodynamic effect is reducing the production of an undesired molecule. In some embodiments, the pharmacodynamic effect is increasing degradation of an undesired molecule, for example uric acid crystals. In some embodiments, the pharmacodynamic effect is an activity of an enzyme.

A pharmacodynamic effect of a therapeutic macromolecule can be evaluated by standard methods. In some aspects of the invention, the pharmacodynamic effect is a reduction of inflammation. The level of inflammation can be assessed by any of the following exemplary methods without limitation, scoring of inflammatory symptoms such as redness or swelling; scoring of arthritic symptoms such as mobility, pain, or joint destruction; scoring of anaphylaxis symptoms such as swelling, blood pressure, shortness of breath; detecting and/or quantifying cell infiltration by histology, immunohistochemistry, flow cytometry; measuring the concentration of a protein or inflammation-associated cytokines such as TNF, IL-1 by ELISA, assessing the expression of gene or inflammation-associated genes by transcriptional analysis; measuring activity of an inflammation-associated cytokine, etc.

In some aspects of the invention, the pharmacodynamic effect is reduction or degradation of an undesired molecule. In some embodiments, the pharmacodynamic effect can be assessed, without limitation, by quantifying the undesired molecule in a tissue or blood sample by methods such as an ELISA. In some embodiments, the pharmacodynamic effect can be assessed by quantifying a molecule that is produced by the degradation of an undesired molecule such as by an ELISA. In some aspects of the invention, the pharmacodynamic effect is the activity of an enzyme that was not previously present or not adequately present. In such embodiments, the activity of an enzyme can be assessed by detecting the presence or the concentration of a product of the enzyme activity.

In some aspects of the invention, a reduced dose of the therapeutic macromolecule is administered to produce a pharmacodynamic effect. A reduced dose of a therapeutic macromolecule for such a purpose comprises any dose of the therapeutic macromolecule that achieves a pharmacodynamic effect in the presence of an anti-therapeutic macromolecule antibody response, with the concomitant administration of an immunosuppressant dose, that is less than the dose needed to achieve a similar pharmacodynamic effect with the therapeutic macromolecule when not administered concomitantly with the immunosuppressant dose in the presence of an anti-therapeutic macromolecule antibody response. A reduced dose can be determined by administering a therapeutic macromolecule, with the concomitant administration of an immunosuppressant dose, at a certain dose in the presence of an anti-therapeutic macromolecule antibody response and assessing the pharmacodynamic effect. The pharmacodynamic effect can then be compared with the pharmacodynamic effect that results through administration of the therapeutic macromolecule without the concomitant administration of an immunosuppressant dose in the presence of an anti-therapeutic macromolecule antibody response. A lower dose that achieves a similar pharmacodynamic effect as determined by such a comparison is a reduced dose.

As mentioned previously, immunosuppressants may be attached to synthetic nanocarriers. Synthetic nanocarriers may be prepared using a wide variety of methods known in the art. For example, synthetic nanocarriers can be formed by methods such as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger issued Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be attached to the synthetic nanocarriers and/or the composition of the polymer matrix.

If synthetic nanocarriers prepared by any of the above methods have a size range outside of the desired range, such synthetic nanocarriers can be sized, for example, using a sieve.

Elements (i.e., components) of the synthetic nanocarriers (such as antigens, immunosuppressants, and the like) may be attached to the overall synthetic nanocarrier, e.g., by one or more covalent bonds, or may be attached by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be attached to components directly or indirectly via non-covalent interactions. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of a synthetic nanocarrier. In embodiments, encapsulation and/or absorption is a form of attaching. In embodiments, the synthetic nanocarriers can be combined with a therapeutic macromolecule or other composition by admixing in the same vehicle or delivery system.

Compositions provided herein may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention may comprise pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, compositions are suspended in a sterile saline solution for injection together with a preservative.

It is to be understood that the compositions of the invention can be made in any suitable manner, and the invention is in no way limited to compositions that can be produced using the methods described herein. Selection of an appropriate method of manufacture may require attention to the properties of the particular moieties being associated.

In some embodiments, compositions are manufactured under sterile conditions or are terminally sterilized. This can ensure that resulting compositions are sterile and non-infectious, thus improving safety when compared to non-sterile compositions. This provides a valuable safety measure, especially when subjects receiving the compositions have immune defects, are suffering from infection, and/or are susceptible to infection. In some embodiments, the compositions may be lyophilized and stored in suspension or as lyophilized powder depending on the formulation strategy for extended periods without losing activity.

Administration according to the present invention may be by a variety of routes, including but not limited to subcutaneous, intravenous, intraperitoneal, intramuscular, transmucosal, transdermal, transcutaneous or intradermal routes. In a preferred embodiment, administration is via a subcutaneous route of administration. The compositions referred to herein may be manufactured and prepared for administration, preferably concomitant administration, using conventional methods.

The compositions of the invention can be administered in effective amounts, such as the effective amounts described elsewhere herein. Doses of dosage forms may contain varying amounts of immunosuppressants and/or therapeutic macromolecules, according to the invention. The amount of immunosuppressants and/or therapeutic macromolecules present in the inventive dosage forms can be varied according to the nature of the therapeutic macromolecules, and/or immunosuppressant, the therapeutic benefit to be accomplished, and other such parameters. In embodiments, dose ranging studies can be conducted to establish optimal therapeutic amounts of immunosuppressant and/or therapeutic macromolecules to be present in the dosage form. In embodiments, the immunosuppressants and/or therapeutic macromolecules are present in the dosage form in an amount effective to generate a desired pharmacodynamic effect and/or a reduced immune response to the therapeutic macromolecules upon administration to a subject. It may be possible to determine amounts of the immunosuppressants and/or therapeutic macromolecules effective to achieve a desired result using conventional dose ranging studies and techniques in subjects. Inventive dosage forms may be administered at a variety of frequencies. In a preferred embodiment, at least one administration of the compositions provided herein is sufficient to generate a pharmacologically relevant response. In more preferred embodiments, at least two administrations or at least three administrations are utilized to ensure a pharmacologically relevant response. In some embodiments, repeated administrations are utilized to ensure a pharmacologically relevant response.

Another aspect of the disclosure relates to kits. In some embodiments, the kit comprises a pharmacodynamically effective dose or more than one dose of a therapeutic macromolecule, such as a reduced pharmacodynamically effective dose. In such embodiments, the kit may also comprise an immunosuppressant dose or more than one dose of immunosuppressant. The immunosuppressant dose and the pharmacodynamically effective dose can be contained within separate containers or within the same container in the kit. In some embodiments, the container is a vial or an ampoule. In some embodiments, the pharmacodynamically effective dose of a therapeutic macromolecule and/or immunosuppressant dose are contained within a solution separate from the container, such that the pharmacodynamically effective dose of a therapeutic macromolecule and/or immunosuppressant dose may be added to the container at a subsequent time. In some embodiments, the pharmacodynamically effective dose of a therapeutic macromolecule and/or immunosuppressant dose are in lyophilized form each in a separate container or in the same container, such that they may be reconstituted at a subsequent time. In some embodiments, the kit further comprises instructions for reconstitution, mixing, administration, etc. In some embodiments, the instructions include a description of the methods described herein. Instructions can be in any suitable form, e.g., as a printed insert or a label. In some embodiments, the kit further comprises one or more syringes.

EXAMPLES

Example 1: Evaluating Immune Responses with Synthetic Nanocarriers Comprising Immunosuppressant and APC Presentable Antigen In Vivo Materials Ovalbumin peptide 323-339 ($OVA_{323-339}$), a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue # R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). Polyvinyl alcohol (85-89% hydrolyzed) was purchased from EMD Chemicals (Product Number 1.41350.1001).

Method for Preparing Synthetic Nanocarrier Containing Rapamycin and Ovalbumin (323-339)

Solutions were Prepared as Follows:

Solution 1: $OVA_{323-339}$ at 20 mg/mL in dilute hydrochloric acid aqueous solution. The solution was prepared by dissolving ovalbumin peptide in 0.13 M hydrochloric acid solution at room temperature.

Solution 2: PLGA at 100 mg/mL in methylene chloride. The solution was prepared by dissolving PLGA in pure methylene chloride.

Solution 3: PLA-PEG at 100 mg/mL in methylene chloride. The solution was prepared by dissolving PLA-PEG in pure methylene chloride.

Solution 4: Rapamycin at 50 mg/mL in methylene chloride. The solution was prepared by dissolving rapamycin in pure methylene chloride.

Solution 5: Polyvinyl alcohol at 50 mg/mL in 100 mM pH 8 phosphate buffer.

A primary water-in-oil emulsion was prepared first. W1/O1 was prepared by combining solution 1 (0.2 mL), solution 2 (0.75 mL), solution 3 (0.25 mL), and solution 4 (0.2 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amounts of peptide and rapamycin in the synthetic nanocarriers were determined by HPLC analysis. The total dry-synthetic nanocarrier mass per mL of suspension was determined by a gravimetric method.

Method for Synthetic Nanocarrier Containing Rapamycin

A primary water-in-oil emulsion was prepared first. W1/O1 was prepared by combining 0.13 M hydrochloric acid solution (0.2 mL), solution 2 (0.75 mL), solution 3 (0.25 mL), and solution 4 (0.2 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amount of rapamycin in the synthetic nanocarrier was determined by HPLC analysis. The total dry-synthetic nanocarrier mass per mL of suspension was determined by a gravimetric method.

Method for Measuring Rapamycin Load

Approximately 3 mg of synthetic nanocarriers were collected and centrifuged to separate supernatant from synthetic nanocarrier pellet. Acetonitrile was added to the pellet, and the sample was sonicated and centrifuged to remove any insoluble material. The supernatant and pellet were injected on RP-HPLC and absorbance was read at 278 nm. The μg found in the pellet were used to calculate % entrapped (load), μg in supernatant and pellet were used to calculate total μg recovered.

Method for Measuring Ovalbumin (323-339) Load

Approximately 3 mg of synthetic nanocarriers were collected and centrifuged to separate supernatant from synthetic nanocarrier pellet. Trifluoroethanol was added to the pellet and the sample was sonicated to dissolve the polymer, 0.2% trifluoroacetic acid was added and sample was sonicated and then centrifuged to remove any insoluble material. The supernatant and pellet were injected on RP-HPLC and absorbance was read at 215 nm. The μg found in the pellet were used to calculate % entrapped (load), μg in supernatant and pellet were used to calculate total μg recovered.

Immunization

The purpose of this experiment was to assess the effects of encapsulated immunosuppressant on ongoing antibody responses by measuring antigen-specific immunoglobulins. One group of animals remained unimmunized as a control. Two groups of animals were immunized using Chicken Ovalbumin (OVA) and CpG with 3 injections (d0, d14 and d28) in the footpad followed by an assessment of antibody titers. For immunization, animals received 20 μl/limb of OVA+CpG (12.5 μg OVA+10 μg CpG), both hind limbs s.c. The treatment, administered on the same days, included administration i.v. (200 μl) or s.c. (20 μl). Nanocarriers were diluted in such a manner that the same amounts of $OVA_{323-339}$ were injected in the treated groups.

Measurement of IgG

The level of IgG antibodies were measured. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4 L, EMD Chemicals, Catalog #6505) and 18 Liters of deionized water.

OVA protein at a stock concentration of 5 mg/ml was used as a coating material. A 1:1000 dilution to 5 µg/ml was used as a working concentration. Each well of the assay plates was coated with 100 µl diluted OVA per well, plates were sealed with sealing film (VWR catalog #60941-120), and incubated overnight at 4° C. Costar 9017 96-well Flat bottom plates were used as assay plates (Costar 9017).

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 µl diluent were added to each well of assay plate(s) to block non-specific binding and plates were incubated at least 2 hours at room temperature. Serum samples were prepared in the setup plate at appropriate starting dilutions. Starting dilutions were sometimes also prepared in 1.5 ml tubes using diluent and then transferred to the set-up plate. Appropriate starting dilutions were determined based on previous data, where available. Where no previous data was available, the lowest starting dilution was 1:40. Once diluted, 200 µl of the starting dilution of the serum sample was transferred from the tube to the appropriate well of the setup plate.

An exemplary setup plate layout is described as follows: Columns 2 and 3 contained anti-Ovalbumin monoclonal IgG2b isotype (AbCam, ab17291) standard, diluted to 0.25 µg/mL (1:4000 dilution). Columns 3-11 contained serum samples (at appropriate dilutions). Columns 1 and 12 were not used for samples or standards to avoid any bias of measurements due to edge effect. Instead, columns 1 and 12 contained 200 µl diluent. Normal mouse serum diluted 1:40 was used as a negative control. Anti-mouse IgG2a diluted 1:500 from 0.5 mg/mL stock (BD Bioscience) was used as an isotype control.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 µL of diluent was added to all wells in rows B-H of the assay plates. A 12-channel pipet was used to transfer samples from the setup plate to the assay plate. Samples were mixed prior to transfer by pipetting 150 µl of diluted serum up and down 3 times. After mixing, 150 µl of each sample was transferred from the setup plate and added to row A of the respective assay plate.

Once the starting dilutions of each sample were transferred from the setup plate to row A of the assay plate, serial dilutions were pipetted on the assay plate as follows: 50 µl of each serum sample was removed from row A using 12-channel pipet and mixed with the 100 µl of diluent previously added to each well of row B. This step was repeated down the entire plate. After pipetting the dilution of the final row, 50 µl of fluid was removed from the wells in the final row and discarded, resulting in a final volume of 100 µl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated, AbCam ab98717) was diluted 1:1500 (0.33 µg/mL) in diluent and 100 µl of the diluted antibody was added to each well. Plates were incubated for 1 hour at room temperature and then washed three times with wash buffer, with each washing step including a soak time of at least 30 seconds.

After washing, detection substrate was added to the wells. Equal parts of substrate A and substrate B (BD Biosciences TMB Substrate Reagent Set, catalog #555214) were combined immediately before addition to the assay plates, and 100 µl of the mixed substrate solution were added to each well and incubated for 10 minutes in the dark. The reaction was stopped by adding 50 µl of stop solution (2N $H_2SO_4$) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v5.4. A four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per column).

Results

Figure 2:
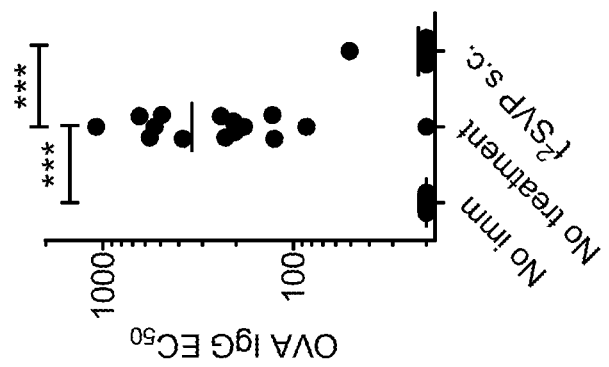
FIG. 2 shows the level of circulating antigen-specific antibody production with a concomitant administration as provided herein.

The results demonstrate the ability to reduce an antigen-specific antibody response using an immunosuppressant dose in combination with the antigen, both the immunosuppressant and antigen being attached to the nanocarriers. FIG. 1 shows a decrease in circulating antigen-specific antibody production with nanocarriers comprising peptide antigen and immunosuppressant when administered intravenously. Two independent experiments were performed using 5 animals in each experiment. FIG. 2 shows a decrease in circulating antigen-specific antibody production with nanocarriers comprising peptide antigen and immunosuppressant when administered subcutaneously. Three independent experiments were performed using 5 animals in each experiment. P values were calculated using a Bonferroni post-test of a regular one-way ANOVA test (*=p<0.05, =p<0.01 and *=p<0.001).

These results demonstrate that an enhanced effect can be obtained using the same amount of ovalbumin protein, when administered under conditions that would ordinarily produce a significant anti-ovalbumin antibody response. Furthermore, this pharmacodynamic effect could have been obtained with a reduced pharmacodynamically effective dose, as the results suggest. Finally, the reproduction of the results supports that a protocol was established that was demonstrated to result in a pharmacodynamic effect with the reduced pharmacodynamically effective dose of the therapeutic macromolecule upon concomitant administration with the immunosuppressant dose.

Example 2: Evaluating Immune Responses Following Concomitant Administration of Synthetic Nanocarriers Comprising Immunosuppressant and Therapeutic Proteins Materials Rapamycin was purchased from TSZ CHEM (185 Wilson Street, Framingham, Mass. 01702; Product Catalogue # R1017). PLGA with 76% lactide and 24% glycolide content and an inherent viscosity of 0.69 dL/g was purchased from SurModics Pharmaceuticals (756 Tom Martin Drive, Birmingham, Ala. 35211. Product Code 7525 DLG 7A.) PLA-PEG block co-polymer with a PEG block of approximately 5,000 Da and PLA block of approximately 40,000 Da was purchased from SurModics Pharmaceuticals (756 Tom Martin Drive, Birmingham, Ala. 35211; Product Code 100 DL mPEG 5000 5CE). Polyvinyl alcohol (85-89% hydrolyzed) was purchased from EMD Chemicals (Product Number 1.41350.1001).

Method for Preparing Synthetic Nanocarriers

Solutions were Prepared as Follows:

Solution 1: PLGA at 75 mg/mL and PLA-PEG at 25 mg/mL in methylene chloride. The solution was prepared by dissolving PLGA and PLA-PEG in pure methylene chloride.

Solution 2: Rapamycin at 100 mg/mL in methylene chloride. The solution was prepared by dissolving rapamycin in pure methylene chloride.

Solution 3: Polyvinyl alcohol at 50 mg/mL in 100 mM pH 8 phosphate buffer.

An oil-in-water emulsion was used to prepare the nanocarriers. The O/W emulsion was prepared by combining solution 1 (1 mL), solution 2 (0.1 mL), and solution 3 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 75,000×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 227 | 6.4 |

Responses to Ovalbumin

Figure 3:
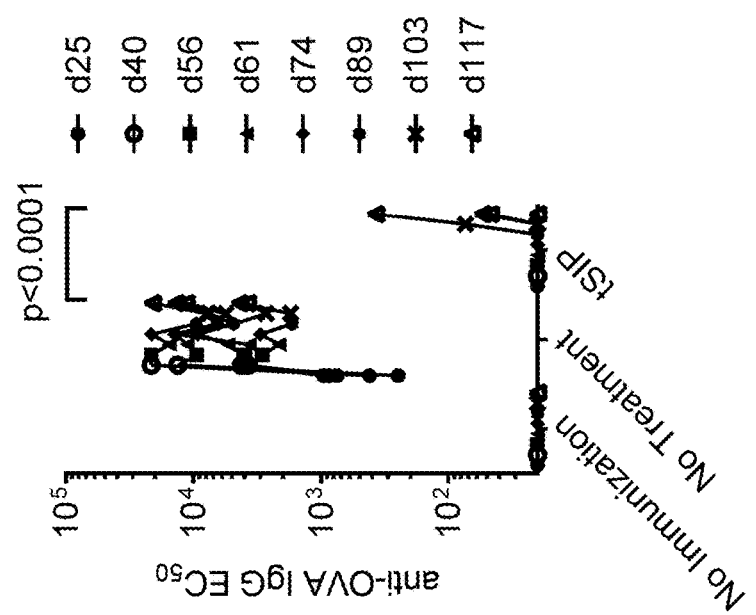
FIG. 3 provides the anti-OVA antibody titers with a concomitant administration as provided herein.

C57BL/6 age-matched (5-6 weeks) female mice (5 per group, 3 groups: naïve control, untreated control, and treatment with synthetic nanocarriers with rapamycin were injected intravenously with 25 µg of chicken ovalbumin induced using high sheer to form aggregates in order to increase its immunogenicity (aggOVA). After these i.v. injections to prime and boost the immune response (administrations on day 0, 14 and 28), subsequent boosts of 25 µg ovalbumin were performed intraperitoneally (i.p. on days 42 and 57), and subcutaneously a 12.5 µg pOVA challenge in the left hind limb (s.c. d62) followed by challenges using the same aggOVA combined with CpG (s.c. day 90, 105 and 135). FIG. 3 shows the results of such immunization protocol. At days 25 and 40, a prominent anti-OVA antibody (Ab) response can be detected in these animals using ELISA (technique generally as described in Example 1). Subsequent injections of aggOVA were observed to maintain these titers or even boost the response. In contrast, when mice were treated using the synthetic nanocarriers administered i.v. (dose calculated to provide 100 µg of rapamycin) concomitantly with aggOVA during only the three first encounters with the antigen on d0, 14 and 28, no IgG response can be detected for the next 60 days even after 4 injections with the immunogenic mixture including aggOVA. See FIG. 3. It is only after the 3 s.c. injections (s.c. day 90, 105 and 135) with aggOVA/KLH and CpG, an extremely immunogenic combination, that a very modest anti-aggOVA IgG response can be detected in treated animals.

Responses to Keyhole Limpet Hemocyanin, a Second Antigen

The same mice as above were also injected with 0.05 µg of a second Ag, Keyhole Limpet Hemocyanin (KLH), with the KLH being mixed with the aggOVA, and administered according to the schedule noted above for the aggOVA. Anti-KLH IgG antibody titer was determined using a method similar to the anti-OVA IgG titer method described in Example 1.

Figure 4:
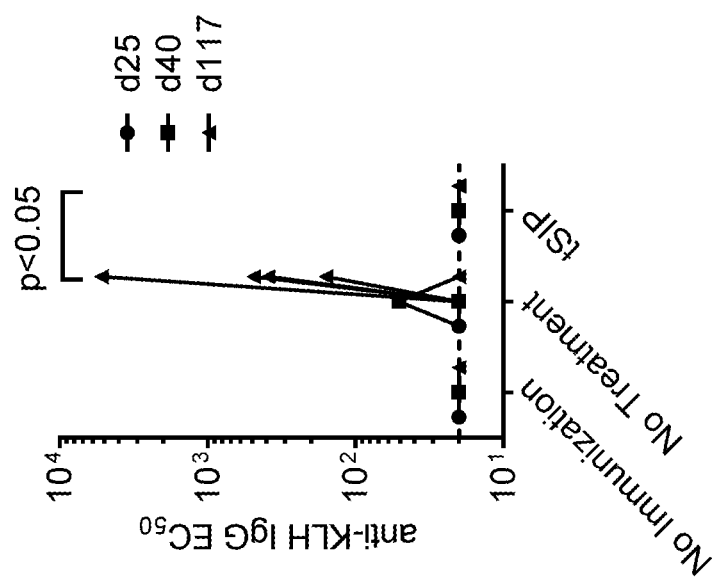
FIG. 4 provides the anti-KLH antibody titers with a concomitant administration as provided herein.

The results in FIG. 4 show that, unlike aggOVA, KLH is not immunogenic in the first phase of encounters with the Ag (d0-40). However, KLH was immunogenic in animals that were not treated with the synthetic nanocarriers after 3 immunizations of KLH in presence of CpG s.c. (s.c. day 90, 105 and 135). A strong anti-KLH response can be observed in these control mice, whereas the mice that received the 3 treatments with synthetic nanocarriers with immunosuppressant in combination with the antigens at the beginning of this protocol have no detectable response even after the KLH/CpG challenges.

These results demonstrate that an enhanced effect can be obtained with the compositions and methods provided herein when administered under conditions that would ordinarily produce a significant antibody response. Also, the results support that a protocol was established that was demonstrated to result in a pharmacodynamic effect.

Example 3: Method for Preparing Nanocarriers Attached to Rapamycin

Materials

Rapamycin was purchased from TSZ CHEM (185 Wilson Street, Framingham, Mass. 01702; Product Code R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: Polyvinyl alcohol @ 50 mg/mL in 100 mM pH 8 phosphate buffer.

An oil-in-water (O/W) emulsion was used to prepare the nanocarriers. The O/W emulsion was prepared by combining Solution 1 (1.0 mL) and Solution 2 (3.0 mL) in a small pressure tube and sonicating at 30% amplitude for 60 seconds using a Branson Digital Sonifier 250. The O/W emulsion was added to a beaker containing 70 mM pH 8 phosphate buffer solution and stirred at room temperature for 2 hours to allow the methylene chloride to evaporate and for the nanocarriers to form. A portion of the nanocarriers was washed by transferring the nanocarrier suspension to a centrifuge tube and centrifuging at 75,600×g and 4° C. for 50 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering and presented in Table 1. The amount of rapamycin in the nanocarrier was determined by HPLC analysis (Table 1). The total dry-nanocarrier mass per mL of suspension was determined by a gravimetric method.

Effective Diameter and Rapamycin Content of Nanocarriers Attached to Rapamycin

| Nanocarrier ID | Effective Diameter (nm) | Rapamycin Content (% w/w) |
|---|---|---|
| 1 | 238 | 10.6 |
| 2 | 241 | 11.1 |
| 3 | 241 | 11.5 |

Materials

Rapamycin was purchased from TSZ CHEM (185 Wilson Street, Framingham, Mass. 01702; Product Code R1017). PLGA with a lactide:glycolide ratio of 1:1 and an inherent viscosity of 0.24 dL/g was purchased from SurModics Pharmaceuticals (756 Tom Martin Drive, Birmingham, Ala. 35211; Product Code 5050 DLG 2.5A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: Polyvinyl alcohol at 50 mg/mL in 100 mM pH 8 phosphate buffer.

Solution 3: 70 mM phosphate buffer, pH 8.

A an oil-in-water emulsion was created by mixing Solutions 1 (1.0 mL) and Solution 2 (3.0 mL) in a small glass pressure tube and sonicating at 30% amplitude for 60 seconds using a Branson Digital Sonifier 250. The emulsion was added to an open 50 mL beaker containing Solution 3 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 40 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The amount rapamycin in the nanocarrier was determined by HPLC analysis. The total dry-nanocarrier mass per mL of suspension was determined by a gravimetric method.

Effective Diameter and Rapamycin Content of Nanocarriers Attached to Rapamycin

| Nanocarrier ID | Effective Diameter (nm) | Rapamycin Load (% w/w) |
|---|---|---|
| 4 | 218 | 9.9 |

Materials

Rapamycin was purchased from TSZ CHEM (185 Wilson Street, Framingham, Mass. 01702; Product Code R1017). PLGA with a lactide:glycolide ratio of 1:1 and an inherent viscosity of 0.24 dL/g was purchased from SurModics Pharmaceuticals (756 Tom Martin Drive, Birmingham, Ala. 35211; Product Code 5050 DLG 2.5A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). F8II.1723 peptide was purchased from AnaSpec (34801 Campus Drive, Fremont, Calif. 94555). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: F8II.1723 (ERLWDYGMSSSPHVL) at 10 mg/mL and sucrose at 100 mg/mL in 50 mM pH 11.5 phosphate buffer. The solution was prepared by dissolving the sucrose in 50 mM pH 11.5 phosphate buffer and then adding the F8II.1723 peptide as a dry powder.

Solution 3: Polyvinyl alcohol at 50 mg/mL in 100 mM pH 8 phosphate buffer.

Solution 4: 70 mM pH 8 phosphate buffer.

A primary (W1/O) emulsion was first created by mixing Solution 1 (1.0 mL) and Solution 2 (0.2 mL) in a small glass pressure tube and sonicating at 50% amplitude for 40 seconds using a Branson Digital Sonifier 250.

A secondary (W1/O/W2) emulsion was then formed by adding Solution 3 (3.0 mL) to the primary emulsion, vortexing to create a crude dispersion, and then sonicating at 30% amplitude for 60 seconds using the Branson Digital Sonifier 250.

The secondary emulsion was added to an open 50 mL beaker containing Solution 4 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The amount rapamycin in the nanocarrier was determined by HPLC analysis. The amount of F8II.1723 in the nanocarrier was determined using a fluorescamine-based assay. The total dry-nanocarrier mass per mL of suspension was determined by a gravimetric method.

Effective Diameter and Rapamycin Content of Nanocarriers Attached to Rapamycin

| Nanocarrier ID | Effective Diameter (nm) | Rapamycin Content (% w/w) | Peptide content (% w/w) |
| --- | --- | --- | --- |
| 5 | 202 | 8.9 | 1.1 |

Materials

Rapamycin was purchased from TSZ CHEM (185 Wilson Street, Framingham, Mass. 01702; Product Code R1017). PLGA with a lactide:glycolide ratio of 1:1 and an inherent viscosity of 0.24 dL/g was purchased from SurModics Pharmaceuticals (756 Tom Martin Drive, Birmingham, Ala. 35211; Product Code 5050 DLG 2.5A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). F8II.75 peptide was purchased from AnaSpec (34801 Campus Drive, Fremont, Calif. 94555). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: F8II.75 (VHLFNIAKPRPPWMG) at 10 mg/mL and sucrose at 100 mg/mL in 50 mM pH 2 phosphate buffer. The solution was prepared by dissolving the sucrose in 50 mM pH 2 phosphate buffer and then adding the F8II.75 peptide as a dry powder.

Solution 3: Polyvinyl alcohol at 50 mg/mL in 100 mM pH 8 phosphate buffer.

Solution 4: 70 mM pH 8 phosphate buffer.

A primary (W1/O) emulsion was first created by mixing Solution 1 (1.0 mL) and Solution 2 (0.2 mL) in a small glass pressure tube and sonicating at 50% amplitude for 40 seconds using a Branson Digital Sonifier 250.

A secondary (W1/O/W2) emulsion was then formed by adding Solution 3 (3.0 mL) to the primary emulsion, vortexing to create a crude dispersion, and then sonicating at 30% amplitude for 60 seconds using the Branson Digital Sonifier 250.

The secondary emulsion was added to an open 50 mL beaker containing Solution 4 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The amount rapamycin in the nanocarrier was determined by HPLC analysis. The amount of F8II.75 in the nanocarrier was determined using a fluorescamine-based assay. The total dry-nanocarrier mass per mL of suspension was determined by a gravimetric method.

Effective Diameter and Rapamycin Content of Nanocarriers Attached to Rapamycin

| Nanocarrier ID | Effective Diameter (nm) | Rapamycin Content (% w/w) | Peptide content (% w/w) |
| --- | --- | --- | --- |
| 6 | 199 | 9.3 | 1.1 |

Materials

Rapamycin was purchased from TSZ CHEM (185 Wilson Street, Framingham, Mass. 01702; Product Code R1017). PLGA with a lactide:glycolide ratio of 1:1 and an inherent viscosity of 0.24 dL/g was purchased from SurModics Pharmaceuticals (756 Tom Martin Drive, Birmingham, Ala. 35211; Product Code 5050 DLG 2.5A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). F8II.2210 peptide was purchased from AnaSpec (34801 Campus Drive, Fremont, Calif. 94555). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: F8II.2210 (TASSYFTNMFATWSPSKAR) at 10 mg/mL and sucrose at 100 mg/mL in 50 mM pH 2 phosphate buffer. The solution was prepared by dissolving the sucrose in 50 mM pH 2 phosphate buffer and then adding the F8II.2210 peptide as a dry powder.

Solution 3: Polyvinyl alcohol at 50 mg/mL in 100 mM pH 8 phosphate buffer.

Solution 4: 70 mM pH 8 phosphate buffer.

A primary (W1/O) emulsion was first created by mixing Solution 1 (1.0 mL) and Solution 2 (0.2 mL) in a small glass pressure tube and sonicating at 50% amplitude for 40 seconds using a Branson Digital Sonifier 250.

A secondary (W1/O/W2) emulsion was then formed by adding Solution 3 (3.0 mL) to the primary emulsion, vortexing to create a crude dispersion, and then sonicating at 30% amplitude for 60 seconds using the Branson Digital Sonifier 250.

The secondary emulsion was added to an open 50 mL beaker containing Solution 4 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The amount rapamycin in the nanocarrier was determined by HPLC analysis. The amount of F8II.2210 in the nanocarrier was determined using a fluorescamine-based assay. The total dry-nanocarrier mass per mL of suspension was determined by a gravimetric method.

Effective Diameter and Rapamycin Content of Nanocarriers Attached to Rapamycin

| Nanocarrier ID | Effective Diameter (nm) | Rapamycin Content (% w/w) | Peptide content (% w/w) |
|---|---|---|---|
| 7 | 215 | 9.3 | 1.6 |

Materials

PLGA with a lactide:glycolide ratio of 1:1 and an inherent viscosity of 0.24 dL/g was purchased from SurModics Pharmaceuticals (756 Tom Martin Drive, Birmingham, Ala. 35211; Product Code 5050 DLG 2.5A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL and PLA-PEG-OMe at 25 mg/mL in methylene chloride. The solution was prepared by dissolving PLGA and PLA-PEG-OMe in pure methylene chloride.

Solution 2: Polyvinyl alcohol at 50 mg/mL in 100 mM pH 8 phosphate buffer.

Solution 3: 70 mM phosphate buffer, pH 8.

A an oil-in-water emulsion was created by mixing Solutions 1 (1.0 mL) and Solution 2 (3.0 mL) in a small glass pressure tube and sonicating at 30% amplitude for 60 seconds using a Branson Digital Sonifier 250. The emulsion was added to an open 50 mL beaker containing Solution 3 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 40 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The total dry-nanocarrier mass per mL of suspension was determined by a gravimetric method.

| Nanocarrier ID | Effective Diameter (nm) |
|---|---|
| 8 | 183 |

Example 4: Evaluating Immune Responses to FVIII

Figure 5:
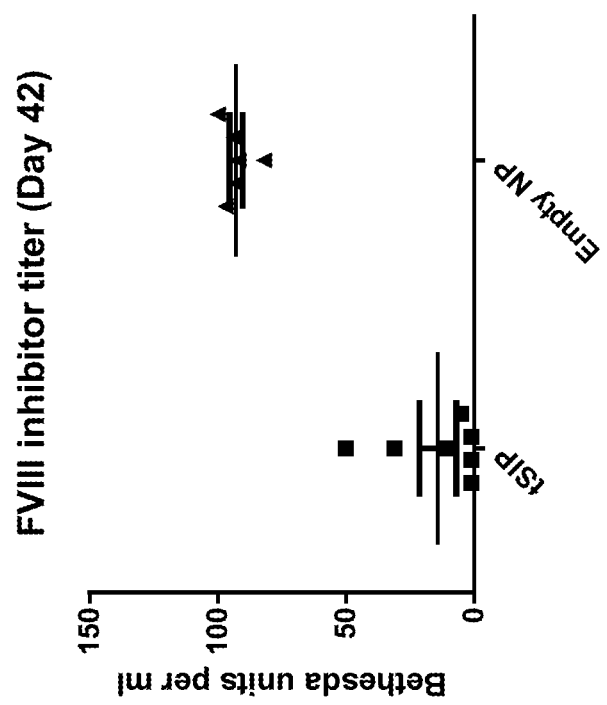
FIG. 5 shows the antibody recall response to FVIII one month following a final nanocarrier and FVIII dosing.

Hemophilia A mice (E16 mice) (n=8 at day 0) received weekly concomitant intravenous (i.v.) injections of the blood clotting protein, Factor VIII (FVIII), and the synthetic nanocarriers attached to rapamycin (Nanocarrier ID 4), or empty nanoparticles (NP) (Nanocarrier ID 8) and FVIII or IVIG (intravenous immunoglobulin) and FVIII for 5 consecutive weeks. To evaluate the antibody recall response to FVIII one month after the final dose of FVIII and nanocarrier attached to rapamycin, the inhibitor titer was determined by Bethesda assay using a chromogenic FVIII activity assay kit (Coatest SP4 FVIII), as presented in FIG. 5.

Figure 6:
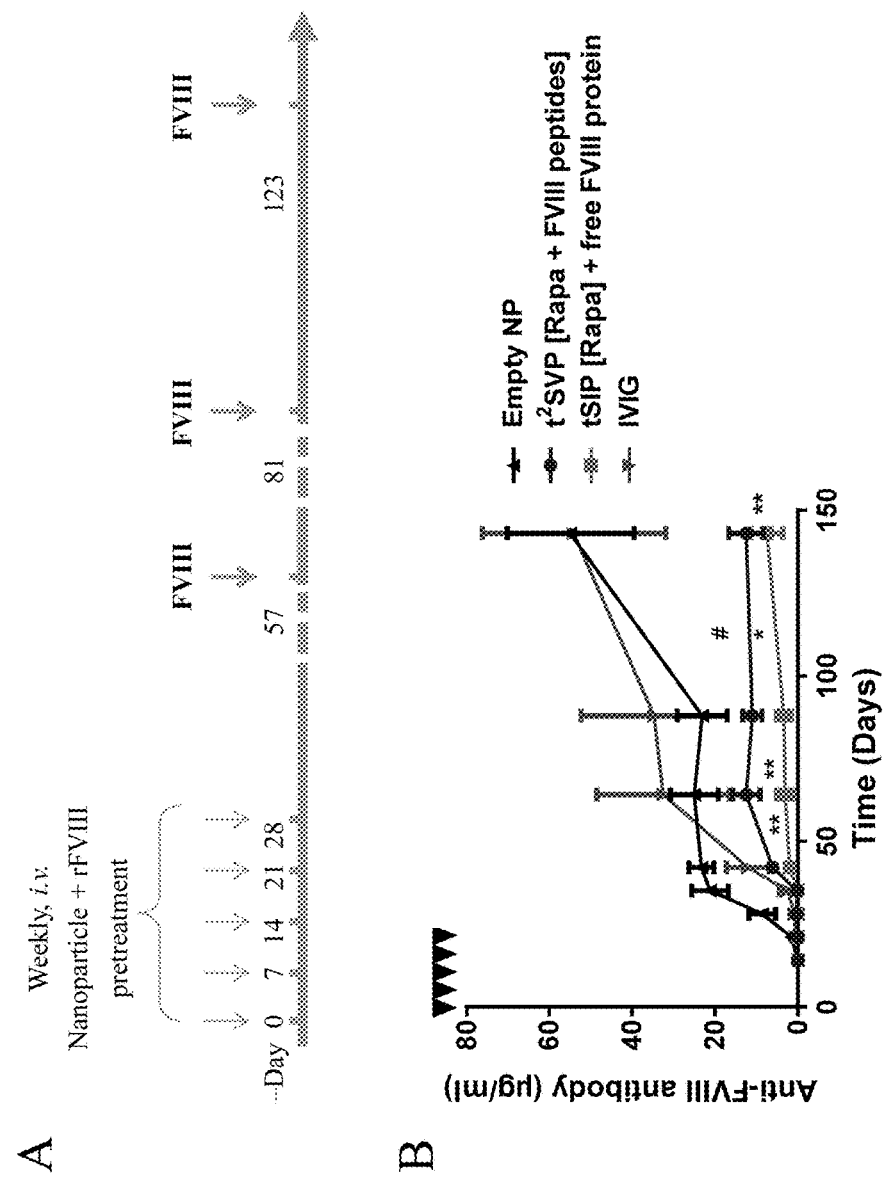
FIGS. 6A and 6B show the efficacy of nanocarrier and FVIII dosing in Hemophilia A mice.

To further assess the lasting tolerance induced by treatment of FVIII and nanocarriers attached to rapamycin, Hemophilia A mice (E16 mice) (n=8 at day 0) received weekly concomitant i.v. injections of synthetic nanocarriers and FVIII peptides (Nanocarrier IDs 5, 6 and 7 mixed to get a 1:1:1 peptide mass ratio and injected together), or nanocarriers attached to rapamycin (Nanocarrier ID 4) and FVIII protein, or empty NP (Nanocarrier ID 8) and FVIII, or IVIG (intravenous immunoglobulin) and FVIII for 5 weeks, as schematically presented in FIG. 6A. At days 57, 81, and 125, the mice were challenged with FVIII (i.v. or i.p.) in the absence of further treatment. Anti-FVIII antibody levels were determined by ELISA. Results at selected time points are presented in FIG. 6B. Data at each time point are expressed as mean±SEM. For statistical analysis, the nanocarrier groups (with protein or peptides) were compared with the empty nanoparticle control group using the student t-test with two tailed distribution. *$p<0.05$ and **$p<0.01$, between Nanocarrier ID 4 with protein and empty NP groups; #$p<0.05$ and ##$p<0.01$, between the nanocarrier and peptide (Nanocarrier IDs 5, 6 and 7) and empty NP groups. All injections of FVIII were 1 µg per injection. All injections of Nanocarrier ID 4 were 100 µg per injection.

The data show that the administration of immunosuppressant attached to synthetic nanocarriers with FVIII or peptides thereof can reduce the anti-Factor FVIII antibody response. This was true using the immunosuppressant synthetic nanocarriers in combination with unattached Factor FVIII protein as well as Factor FVIII peptides also attached to the synthetic nanocarriers. The data also show that such administration can result in improved activity of Factor VIII. This demonstrates the reduction of an undesired immune response against a protein as well as improved efficacy with concomitant administration of immunosuppressant attached to synthetic nanocarriers. Finally, the results support that a protocol was established as provided herein.

Example 5: Evaluating Responses to HUMIRA/Adalimumab

Figure 7:
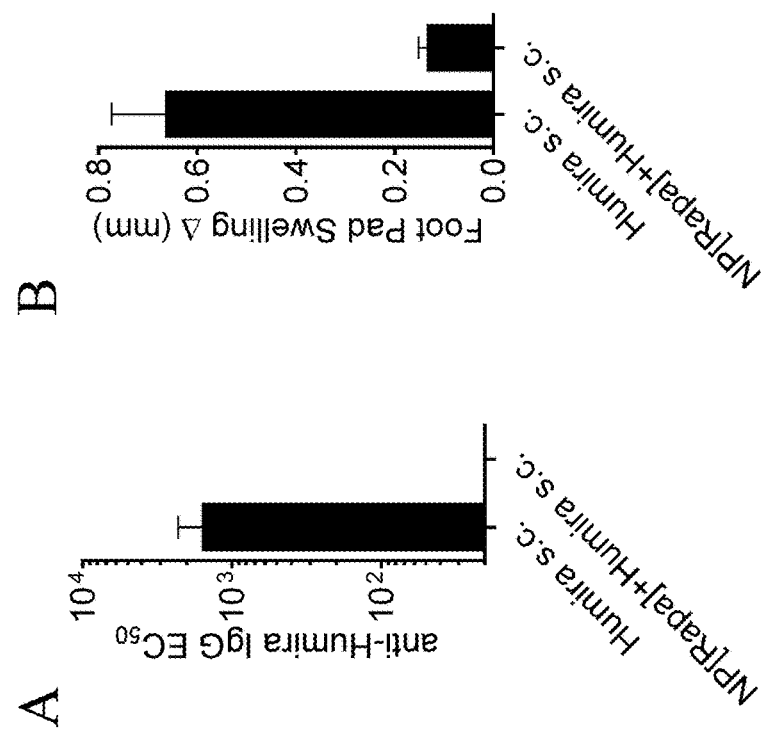
FIGS. 7A and 7B show immune responses to HUMIRA in mice that were treated with HUMIRA/adalimumab with or without nanocarriers attached to rapamycin.
Figure 8:
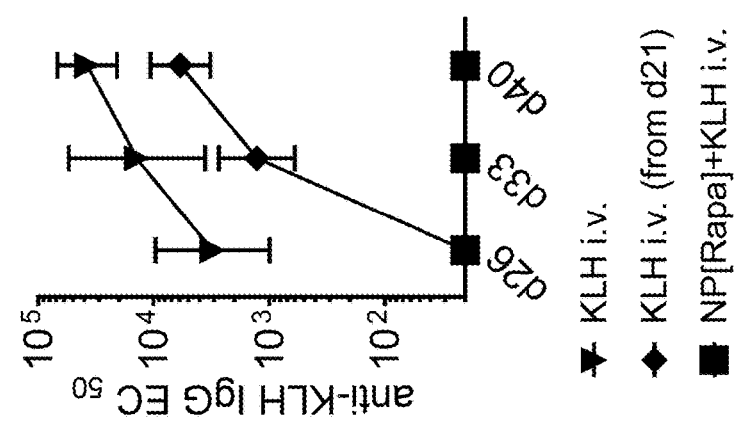
FIG. 8 shows anti-Keyhole Limpet Hemocyanin (KLH) antibody titers in mice that were treated with KLH with or without nanocarriers attached to rapamycin.
Figure 9:
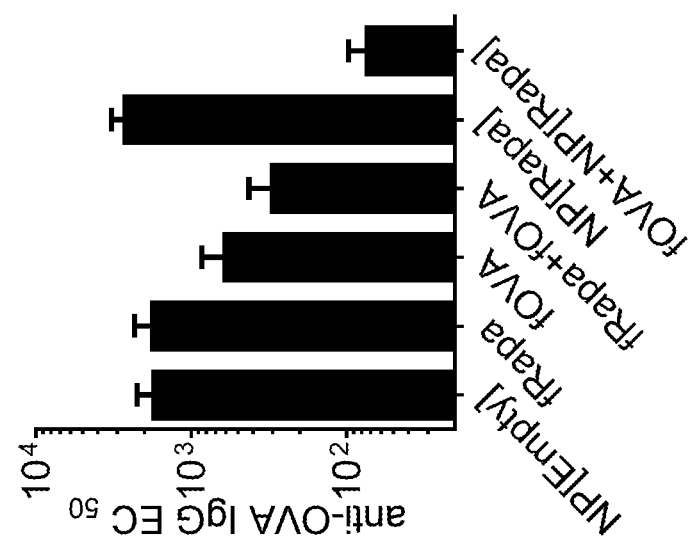
FIG. 9 shows anti-ovalbumin (OVA) antibody titers in mice that were treated with OVA with or without nanocarriers attached to rapamycin.
Figure 10:
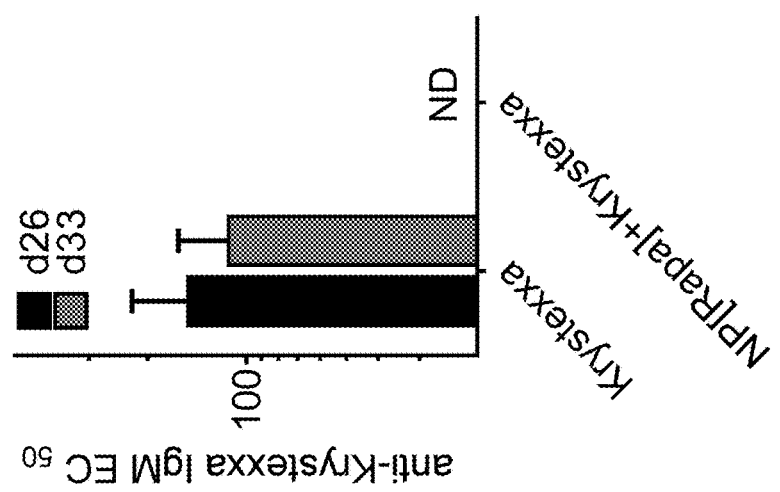
FIG. 10 shows anti-KRYSTEXXA antibody titers in mice that were treated with KRYSTEXXA with or with nanocarriers attached to rapamycin.

Control C57BL/6 age-matched (5-6 weeks) females were injected subcutaneously (s.c.) in the front limbs with 60 µg of HUMIRA once a week until day 29 (on d0, 7, 14, 22, 29, across all groups and conditions). Another group received similar injections, but 0.9 mg of nanocarrier attached to rapamycin (Nanocarrier ID 1, 2 or 3) were admixed to the solution of HUMIRA on the priming day 0. The results presented in FIG. 7A show the antibody titers in the blood of all animals at day 21. The control animals develop a robust antibody response against HUMIRA while treated animals remain completely negative even after 20 days and two injections of HUMIRA without treatment. At day 29, the animals received another challenge in one hind limb while the other hind limb received saline in order to test the local antibody-mediated type I hypersensitivity response. For this, the thickness of the hind limbs were measured with the help of a caliper one hour after the injection. The difference in thickness between the two limbs is presented in FIG. 7B. Similar to the antibody results, the treatment with the nanocarriers abolished the inflammatory response induced by local administration of HUMIRA.

Figure 11:
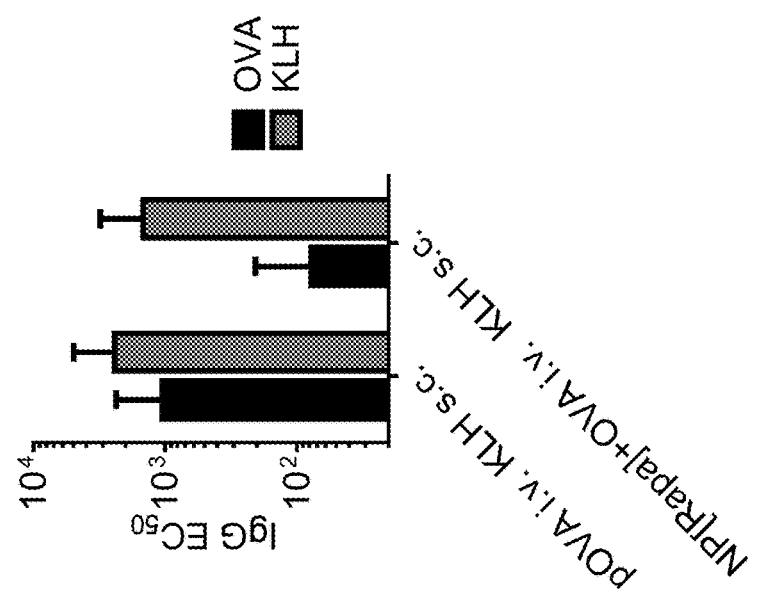
FIG. 11 shows antibody titers in mice that were treated with OVA and KLH either in the presence or absence of nanocarriers attached to rapamycin.

These results show that administration of immunosuppressant attached to synthetic nanocarriers with HUMIRA can reduce undesired anti-HUMIRA antibody response as well as eliminate undesired inflammatory reactions that can result from the administration of HUMIRA without the immunosuppressant nanocarrier composition. This demonstrates the reduction of undesired immune responses against a protein with concomitant administration of immunosuppressant attached to synthetic nanocarriers. Finally, the results support that a protocol was established as provided herein.

Example 6: Evaluating Responses to Keyhole Limpet Hemocyanin (KLH)

Control C57BL/6 age-matched (5-6 weeks) females were injected intravenously (i.v.) in the tail vain with 200 μg of Keyhole Limpet Hemocyanin (KLH) starting at day 0 or day 21 once a week until 34 (on d0, 7, 14, 21, 28, 34). Another group received similar injections from day 0 to day 34, but 0.47 mg of nanocarrier attached to rapamycin (Nanocarrier ID 1, 2 or 3) were admixed to the solution of KLH on days 0, 14 and 21 followed by KLH alone injections weekly between days 21 and 34 (on d21, 28, 34). The results presented in FIG. 8 show the antibody titers in the blood of all animals at the indicated time points. The control animals that started immunization at day 0 or at day 21 develop very similar responses (EC50=3-5×$10^3$) after three injections using the same amounts of KLH (day 26 and 40, respectively). In contrast, animals that received three injections of the nanocarriers remain completely negative after three injections of KLH alone.

The data show that the administration of immunosuppressant attached to synthetic nanocarriers with KLH can reduce the anti-KLH antibody response, and such a reduction can remain even after being administered KLH subsequent to the nanocarrier treatment. This demonstrates the reduction of an undesired immune response against a protein with concomitant administration of immunosuppressant attached to synthetic nanocarriers. Finally, the results support that a protocol was established as provided herein.

Example 7: Evaluating Responses to Ovalbumin

C57BL/6 age-matched (5-6 weeks) female were injected i.v. in the tail vein on days −21 and −13 with 1.2 mg of unattached nanoparticles (NP[Empty]) (Nanocarrier ID 8), free rapamycin (fRapa) (100 μg), 22 μg of free chicken Ovalbumin (fOVA), a combination of fRapa and fOVA, 1.2 mg of nanocarrier attached to rapamycin (NP[Rapa], 100 μg of rapamycin content) (Nanocarrier ID 1, 2 or 3) alone or in combination with 22 μg of fOVA. At day 0 all animals were injected s.c. in the hind limbs with 2.5 μg of particulate OVA (pOVA) admixed to 2 μg of CpG followed by injections of 2.5 μg pOVA on days 7 and 14. In the absence of any treatment (NP[Empty]), the animals develop a robust immune response toward OVA that can be measured by the anti-OVA IgG antibody titers. The antibody titers at day 22 shown in FIG. 9 demonstrate that 2 doses of synthetic nanocarriers administered concomitantly with OVA in the same solution (fOVA+NP[Rapa]) were effective in preventing antibody formation to OVA even after 1 injection of OVA+CpG and 2 injections of OVA alone.

The data show that the administration of immunosuppressant attached to synthetic nanocarriers with OVA can reduce the anti-OVA antibody response, and such a reduction can remain even after being administered OVA in combination with a strong adjuvant. This demonstrates the reduction of an undesired immune response against a protein with concomitant administration of immunosuppressant attached to synthetic nanocarriers. Finally, the results support that a protocol was established as provided herein.

Example 8: Evaluating Responses to KRYSTEXXA

A control group of C57BL/6 age-matched (5-6 weeks) female were injected i.v. in the tail vain with PBS while the treated group was injected with 0.9 mg of nanocarriers attached to rapamycin (Nanocarrier ID 1, 2 or 3) in combination with 40 μg of KRYSTEXXA on days −21 and −14. All animals received weekly injections from day 0 to day 28 of 100 μg of KRYSTEXXA combined to 20 μg of CpG s.c. in the hind limb (d0, 7, 12, 28). The control animals develop an immune response against KRYSTEXXA that can be measured by the anti-KRYSTEXXA IgM antibody titers. The results in FIG. 10 show that treating animals with synthetic nanocarriers administered concomitantly with KRYSTEXXA in the same solution were effective in preventing antibody formation to KRYSTEXXA for a prolonged period of time. The treated animals did not develop an anti-KRYSTEXXA response even after five injections of KRYSTEXXA+CpG without the nanocarriers.

The data show that the administration of immunosuppressant attached to synthetic nanocarriers with KRYSTEXXA can reduce the anti-KRYSTEXXA antibody response, and such a reduction can remain even after being administered KRYSTEXXA subsequent to the nanocarrier treatment with a strong adjuvant. This demonstrates the reduction of an undesired immune response against a protein with concomitant administration of immunosuppressant attached to synthetic nanocarriers. Finally, the results support that a protocol was established as provided herein.

Example 9: Evaluating Responses to Ovalbumin and KLH

The control group of C57BL/6 age-matched (5-6 weeks) female were injected i.v. in the tail vein with 2.5 μg of an immunogenic form of particulate Ovalbumin (pOVA) and 2 μg of Keyhole Limpet Hemocyanin (KLH) s.c. in the hind limb once a week for 49 days (d0, 7, 14, 20, 28, 35, 42, 49). The other group of animals received pOVA and KLH in the same routes and amounts but admixed to 0.2 mg of nanocarrier attached to rapamycin (Nanocarrier ID 1, 2 or 3) on days 0, 7 and 14 followed by pOVA injections between days 20 and 42 (same amounts as before). The control animals develop a robust immune response against OVA and KLH that can be measured by the anti-OVA or anti-KLH IgG antibody titers. The antibody titers at day 54 shown in FIG. 11 demonstrate that 3 doses of synthetic nanocarriers administered concomitantly with pOVA in the same solution were effective in reducing and preventing antibody formation to OVA for a prolonged period of time but not the KLH (that was injected in another location s.c.). The treated animals did not develop an anti-OVA response even after five injections of pOVA alone.

The data show that the concomitant administration of immunosuppressant attached to synthetic nanocarriers with a protein can reduce the anti-protein antibody response but that such a response is specific to the protein administered by the same route. This demonstrates the reduction of an undesired immune response against a protein with concomitant administration of immunosuppressant attached to synthetic nanocarriers. Finally, the results support that a protocol was established as provided herein.

Example 10: Evaluating Responses to KLH

Figure 12:
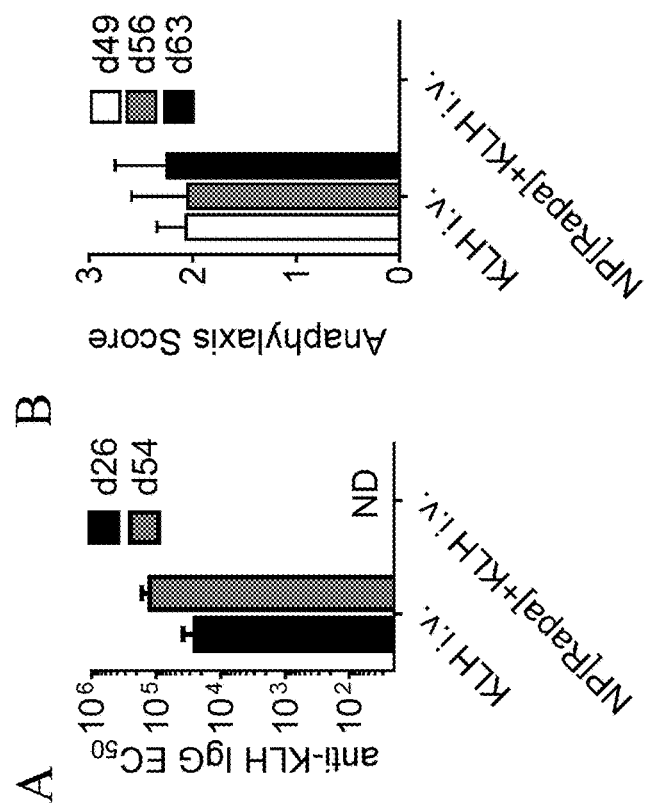
FIGS. 12A and 12B show immune responses to KLH in mice that were treated with KLH with or without nanocarriers attached to rapamycin.

Control C57BL/6 age-matched (5-6 weeks) female were injected i.v. in the tail vain with 200 µg of Keyhole Limpet Hemocyanin (KLH) once a week for 63 days (d0, 7, 14, 21, 28, 35, 42, 49, 56, 63). The other group received similar injections but 0.9 mg of nanocarriers attached to rapamycin (Nanocarrier ID 1, 2 or 3) were admixed to the solution of KLH at days 0, 7, 14 and 21 followed by KLH six injections (same amount) between days 28 and 63. The control animals developed a robust response to KLH that can be measured by the anti-KLH IgG antibody titers as well as the anaphylactic reaction induced by the injections. The results in FIG. 12A show the antibody titers in the blood of all animals at the indicated time points, and the anaphylaxis scores induced by the injection of the antigen are presented in FIG. 12B. Four doses of synthetic nanocarriers administered concomitantly with KLH were effective in reducing and preventing antibody formation and anaphylaxis for a prolonged period of time. Indeed, treated animals did not develop an anti-KLH response even after four injections of KLH alone which in control animals was largely sufficient to create a response (day 26).

These results show that compositions provided herein when administered over a period of time concomitantly with a protein can reduce or prevent antibody formation and anaphylaxis for prolonged periods of time. Anaphylaxis scores were determined by three independent observers as follows: 0=no symptom, 1=lethargy, 2=lethargy and inability to right, 3=moribund.

These results show that administration of immunosuppressant attached to synthetic nanocarriers with KLH can reduce undesired anti-KLH antibody response as well as eliminate undesired anaphylactic reactions that can result from the administration of KLH without the immunosuppressant nanocarrier composition. This demonstrates the reduction of undesired immune responses against a protein with concomitant administration of immunosuppressant attached to synthetic nanocarriers. Finally, the results support that a protocol was established as provided herein.

Example 11: Evaluating Anti-HUMIRA Immune Responses in Arthritic Animals

Transgenic animals overexpressing human tumor necrosis factor alpha (huTNFaTg) develop progressive rheumatoid arthritis over the course of 20 weeks from birth. This process can be prevented by using the fully human anti-human TNFα antibody HUMIRA/adalimumab. However, repetitive administration of the initial therapeutic dose of HUMIRA (60 µg) leads to anti-drug antibody formation (ADA) that neutralizes the therapeutic benefit. Only very high doses can then maintain the therapeutic benefit and surmount the neutralizing immune response. For example, it is thought that about 200 µg is needed to effect maximal inhibition of inflammation in an example of such a mouse model (Binder et al., Arthritis & Rheumatism, Vol. 65 (No. 3), March 2013, pp. 608-617).

Figure 13:
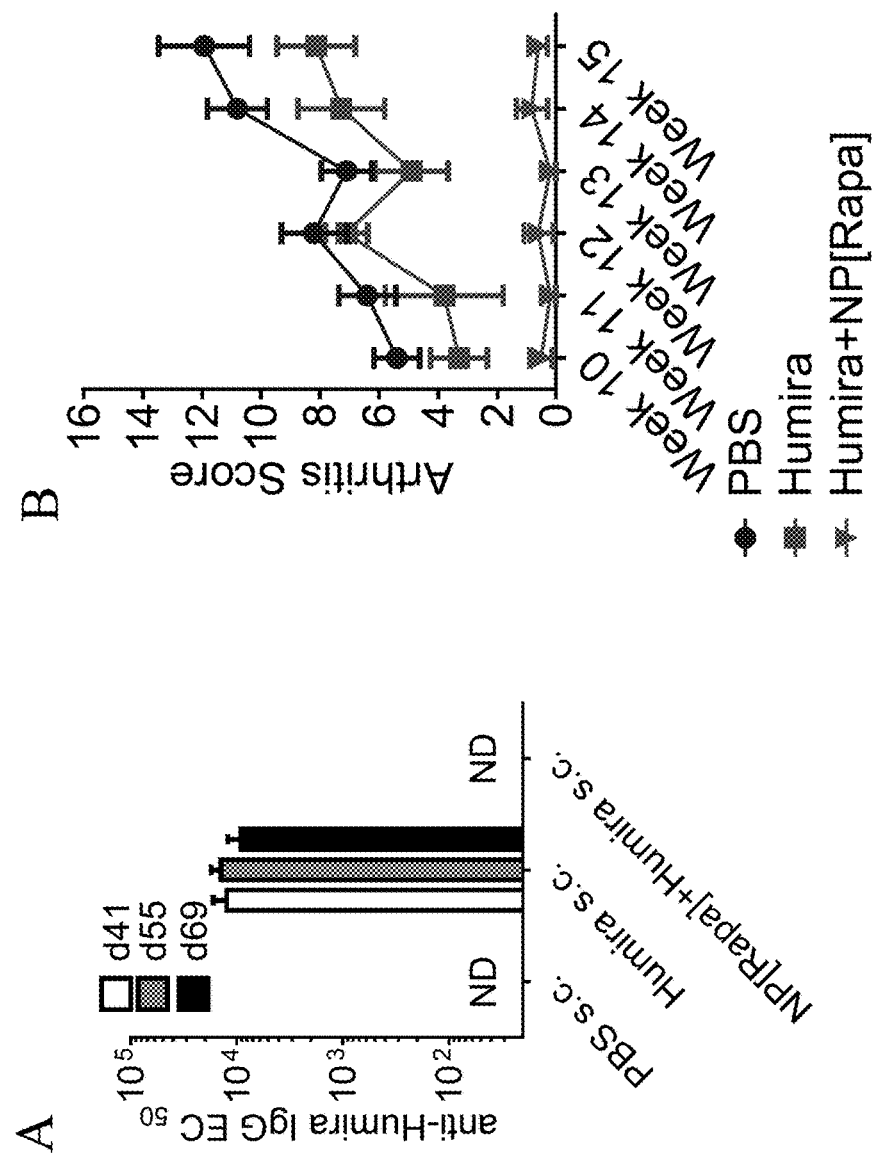
FIGS. 13A and 13B show immune responses to HUMIRA/adalimumab in mice that were treated with HUMIRA/adalimumab with or without nanocarriers attached to rapamycin.

Age-matched huTNFaTg 5 week old female animals were either injected s.c. in the subscapular area with saline (PBS) or 60 µg of HUMIRA weekly or with a mixture of HUMIRA and 0.87 mg of nanocarriers attached to rapamycin (Nanocarrier ID 1, 2 or 3) for the first 7 injections (day 0, 7, 14, 21, 28, 35, 42, weeks 5 to 12 of age) followed by 3 injections of HUMIRA alone (same amount) (day 49 to 63, weeks 13 to 15 of age). The results in FIG. 13A show the antibody titers in the blood of all animals at day 21. The control animals that did not receive HUMIRA have no anti-HUMIRA titers, as expected; whereas a robust antibody response can be observed in the control animals that received only HUMIRA. In contrast, the animals treated with the nanocarriers remain completely negative even after three injections of HUMIRA without treatment. The monitoring of the limbs of these animals revealed a progressive disease that was already evident at 10 weeks of age in the control animals. The animals treated with HUMIRA alone had a significant blockade of the disease progression however adding nanocarriers to this regimen dramatically blocked the emergence of arthritic symptoms. The scores here represent the total of 4 independent scorers as: 1) represents synovitis, joint effusions and soft tissue swelling 2) includes proliferating inflamed synovial tissue which grows into joint cavity and destroys cartilage 3) shows extensive loss of cartilage, erosion around the margins of joint, and deformities 4) is almost end stage of the disease with fibrous or bony stiffening of joint, which ends it's functional life.

These results show that administration of immunosuppressant attached to synthetic nanocarriers with HUMIRA can reduce undesired anti-HUMIRA antibody response. The benefit of the concomitant administration is also evidenced by the further reduced arthritic score which demonstrate improved efficacy of HUMIRA. This demonstrates not only the reduction of undesired immune responses against a therapeutic protein with concomitant administration of immunosuppressant attached to synthetic nanocarriers but also improved efficacy. This also demonstrates that a higher dose of the therapeutic is not needed with the inventive concomitant administration provided herein. Further, based on the level of reduction in the arthritic score with the same dose of HUMIRA, reduced amounts of HUMIRA could also be used that would provide improved efficacy as compared to the amounts of HUMIRA that would be needed without the concomitant administration of immunosuppressant doses as provided herein. It is important to note that the amount of HUMIRA used in this example was 60 µg, much reduced as compared with amounts used in the art of about 200 µg in order to effect maximal inhibition of inflammation by HUMIRA (Binder et al., Arthritis & Rheumatism, Vol. 65 (No. 3), March 2013, pp. 608-617). Finally, the results support that a protocol was established as provided herein.

Example 12: Mesoporous Silica Nanoparticles with Attached Ibuprofen (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 μL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Ibuprofen is loaded by suspending the particles in a solution of sodium ibuprofen (1 mg/L) for 72 h. Free ibuprofen is then washed from the particles by centrifugation and redispersing in water.

Example 13: Liposomes Containing Cyclosporine A (Prophetic)

The liposomes are formed using thin film hydration. 1,2-Dipalmitoyl-sn-glycero-3-phosphocholine (DPPC) (32 μmol), cholesterol (32 μmol), and cyclosporin A (6.4 μmol) are dissolved in pure chloroform (3 mL). This lipid solution is added to a 50 mL round-bottom flask, and the solvent is evaporated on a rotary evaporator at a temperature of 60° C. The flask is then flushed with nitrogen gas to remove remaining solvent. Phosphate buffered saline (2 mL) and five glass beads are added to the flask, and the lipid film is hydrated by shaking at 60° C. for 1 h to form a suspension. The suspension is transferred to a small pressure tube and sonicated at 60° C. for four cycles of 30 s pulses with a 30 s delay between each pulse. The suspension is then left undisturbed at room temperature for 2 h to allow for complete hydration. The liposomes are washed by centrifugation followed by resuspension in fresh phosphate buffered saline.

Example 14: Preparation of Gold Nanocarriers (AuNCs) Containing Rapamycin (Prophetic)

Preparation of HS-PEG-Rapamycin:

A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Formation of Gold NCs (AuNCs):

An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 μm membrane filter to give the AuNCs solution. The AuNCs are characterized using visible spectroscopy and transmission electron microscopy. The AuNCs are ca. 20 nm diameter capped by citrate with peak absorption at 520 nm.

AuNCs Conjugate with HS-PEG-Rapamycin:

A solution of 150 μl of HS-PEG-rapamycin (10 μM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC-S-PEG-rapamycin is then pellet washed with 1×PBS buffer. The purified Gold-PEG-rapamycin nanocarriers are then resuspended in suitable buffer for further analysis and bioassays.

Example 15: Liposomes Containing Rapamycin and Ovalbumin (Prophetic)

The liposomes are formed by thin film hydration. 1,2-Dipalmitoyl-sn-glycero-3-phosphocholine (DPPC) (32 μmol), cholesterol (32 μmol), and rapamycin (6.4 μmol) are dissolved in pure chloroform (3 mL). This lipid solution is added to a 10 mL glass tube and the solvent is removed under nitrogen gas stream and desiccated for 6 hr. under vacuum. Multilamellar vesicles are obtained by hydration of the film with 2.0 ml of 25 mM MOPS buffer pH 8.5, containing excess amount of Ovalbumin. The tube is vortexed until the lipid film is peeled off from the tube surface. To break the multilamellar vesicles into monolamellar, ten cycles of freezing (liquid nitrogen) and thawing (30° C. water bath) are applied. The sample is then diluted to 1 ml in 25 mM MOPS buffer pH 8.5. Size of the resulting liposome is homogenized by extrusion by passing the sample 10 fold through a 200 nm pore polycarbonate filters. The resulting liposomes are then used for further analysis and bioassays.

Example 16: Tolerogenic Responses to HUMIRA Prevent Formation of Neutralizing Anti-HUMIRA Responses in Arthritic Animals Materials Rapamycin was purchased from TSZ CHEM (185 Wilson Street, Framingham, Mass. 01702; Product Code R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride. Solution 2: Polyvinyl alcohol @ 50 mg/mL in 100 mM pH 8 phosphate buffer.

An oil-in-water emulsion was used to prepare the nanocarriers. The O/W emulsion was prepared by combining Solution 1 (1.0 mL) and Solution 2 (3.0 mL) in a small pressure tube and sonicating at 30% amplitude for 60 seconds using a Branson Digital Sonifier 250. The O/W emulsion was added to a beaker containing 70 mM pH 8 phosphate buffer solution and stirred at room temperature for 2 hours to allow the methylene chloride to evaporate and for the nanocarriers to form. A portion of the nanocarriers was washed by transferring the nanocarrier suspension to a centrifuge tube and centrifuging at 75,600×g and 4° C. for 50 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 241 | 11.5 |

Transgenic animals overexpressing human tumor necrosis factor alpha (huTNFαTg) develop progressive rheumatoid arthritis over the course of 20 weeks from birth. This process can be prevented by using the fully human anti-human TNFα antibody Adalimumab or HUMIRA. However repetitive administration of the initial therapeutic dose of HUMIRA (60 µg) leads to anti-drug antibody formation (ADA) that neutralizes the therapeutic benefit.

Figure 14:
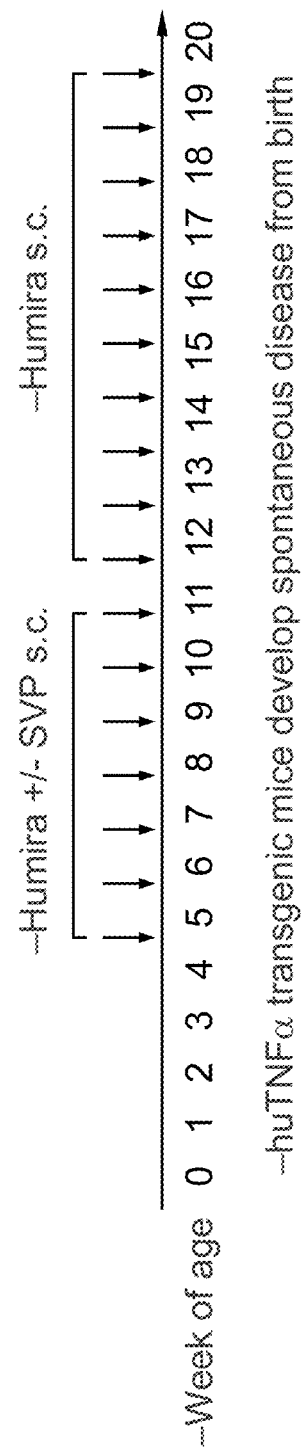
FIG. 14 provides an exemplary protocol for practicing the methods provided herein.

Age-matched HuTNFαTg 5 week old female animals were either injected s.c. in the subscapular area with saline (PBS) or 60 µg of HUMIRA weekly or with a mixture of HUMIRA and 0.87 mg of tolerogenic nanoparticles for the first 7 injections (day 0 to 42, weeks 5 to 11 of age) followed by 10 weekly injections of HUMIRA alone (same amounts) (day 49 to 107, weeks 12 to 20 of age). The protocol is shown in FIG. 14.

Figure 15:
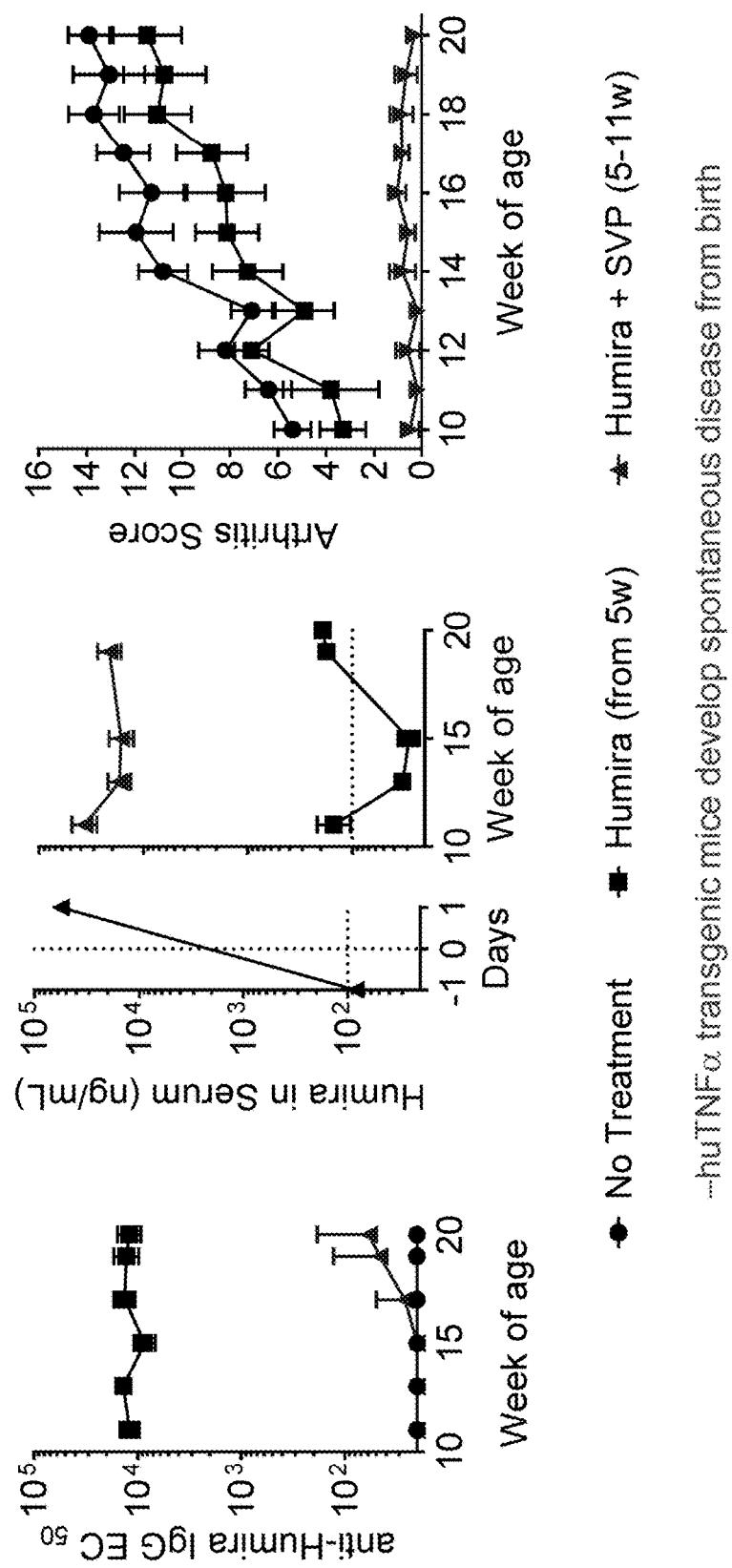
FIG. 15 shows the beneficial effects of practicing a method provided herein in regard to therapy with HUMIRA.

The results in FIG. 15 (left panel) show the antibody titers in the blood of all animals at different time points. The control mock-treated animals have no titers as expected whereas a robust anti-HUMIRA antibody response can be observed in the animals that received just HUMIRA. Treatment with tolerogenic nanocarriers from week 5 to week 11 of age led to a complete resistance to develop anti-HUMIRA titers even after 10 injections of HUMIRA without the tolerogenic treatment (weeks 12 to 20). The monitoring of the limbs of these animals revealed a progressive disease that was already evident at 10 weeks of age. HUMIRA alone had a significant blockade of the disease progression however adding tolerogenic nanocarriers to this regimen dramatically blocked the emergence of arthritic symptoms. The scores here represent the average total of 4 independent scorers as: 1) represents synovitis, joint effusions and soft tissue swelling 2) includes proliferating inflamed synovial tissue which grows into joint cavity and destroys cartilage 3) shows extensive loss of cartilage, erosion around the margins of joint, and deformities 4) is almost end stage of the disease with fibrous or bony stiffening of joint, which ends it's functional life.

These results show that compositions provided herein when administered over a period of time concomitantly with a protein can reduce or prevent antibody formation to a biological therapeutic and therefore improving its efficacy and therapeutic window for prolonged periods of time. These results also show that administration of immunosuppressant attached to synthetic nanocarriers with HUMIRA can reduce undesired anti-HUMIRA antibody response. The benefit of the concomitant administration is also evidenced by the further reduced arthritic score which demonstrates improved efficacy of HUMIRA. This demonstrates not only the reduction of undesired immune responses against a therapeutic protein with concomitant administration of immunosuppressant attached to synthetic nanocarriers but also improved efficacy. This also demonstrates that a higher dose of the therapeutic is not needed with the inventive concomitant administration provided herein. Further, based on the level of reduction in the arthritic score with the same dose of HUMIRA, reduced amounts of HUMIRA could also be used that would provide improved efficacy as compared to the amounts of HUMIRA that would be needed without the concomitant administration of immunosuppressant doses as provided herein. It is important to note that the amount of HUMIRA used in this example was 60 µg, much reduced as compared with amounts used in the art of about 200 µg in order to effect maximal inhibition of inflammation by HUMIRA (Binder et al., Arthritis & Rheumatism, Vol. 65 (No. 3), March 2013, pp. 608-617). Finally, the results support that a protocol was established as provided herein.

Example 17: Evaluating Anti-HUMIRA Immune Responses

Materials

Rapamycin was purchased from TSZ CHEM (185 Wilson Street, Framingham, Mass. 01702; Product Code R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were Prepared as Follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride. Solution 2: Polyvinyl alcohol @ 50 mg/mL in 100 mM pH 8 phosphate buffer.

An oil-in-water emulsion was used to prepare the nanocarriers. The O/W emulsion was prepared by combining Solution 1 (1.0 mL) and Solution 2 (3.0 mL) in a small pressure tube and sonicating at 30% amplitude for 60 seconds using a Branson Digital Sonifier 250. The O/W emulsion was added to a beaker containing 70 mM pH 8 phosphate buffer solution and stirred at room temperature for 2 hours to allow the methylene chloride to evaporate and for the nanocarriers to form. A portion of the nanocarriers was washed by transferring the nanocarrier suspension to a centrifuge tube and centrifuging at 75,600×g and 4° C. for 50 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 238 | 10.6 |

Rapamycin-containing nanocarriers were generated using the materials and methods described above. Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 241 | 11.5 |

Anti-HUMIRA immune and neutralizing responses in arthritic animals were evaluated. Transgenic animals overexpressing human tumor necrosis factor alpha (huTNFαTg) develop progressive rheumatoid arthritis over the course of 20 weeks from birth. This process can be prevented by using the fully human anti-human TNFα antibody Adalimumab or HUMIRA. However repetitive administration of the initial therapeutic dose of HUMIRA (60 µg) leads to anti-drug antibody formation (ADA) that neutralizes the therapeutic benefit. Higher quantities of Humira (200 µg) can be injected to overcome this antagonizing immune response to allow for the therapeutic effect of Humira.

Figure 16:
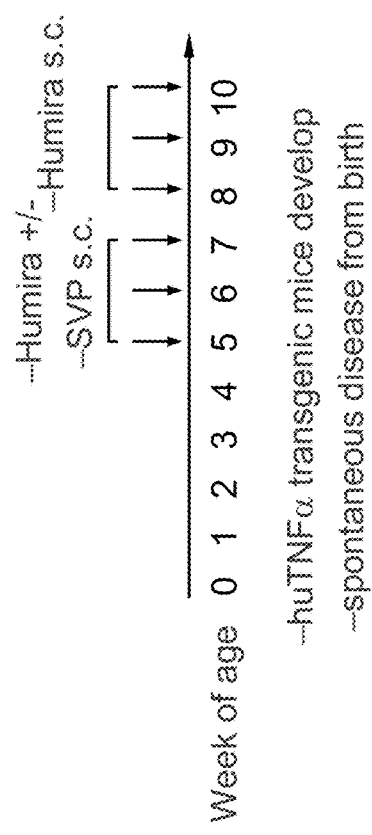
FIG. 16 provides an exemplary protocol for practicing the methods provided herein.
Figure 17:
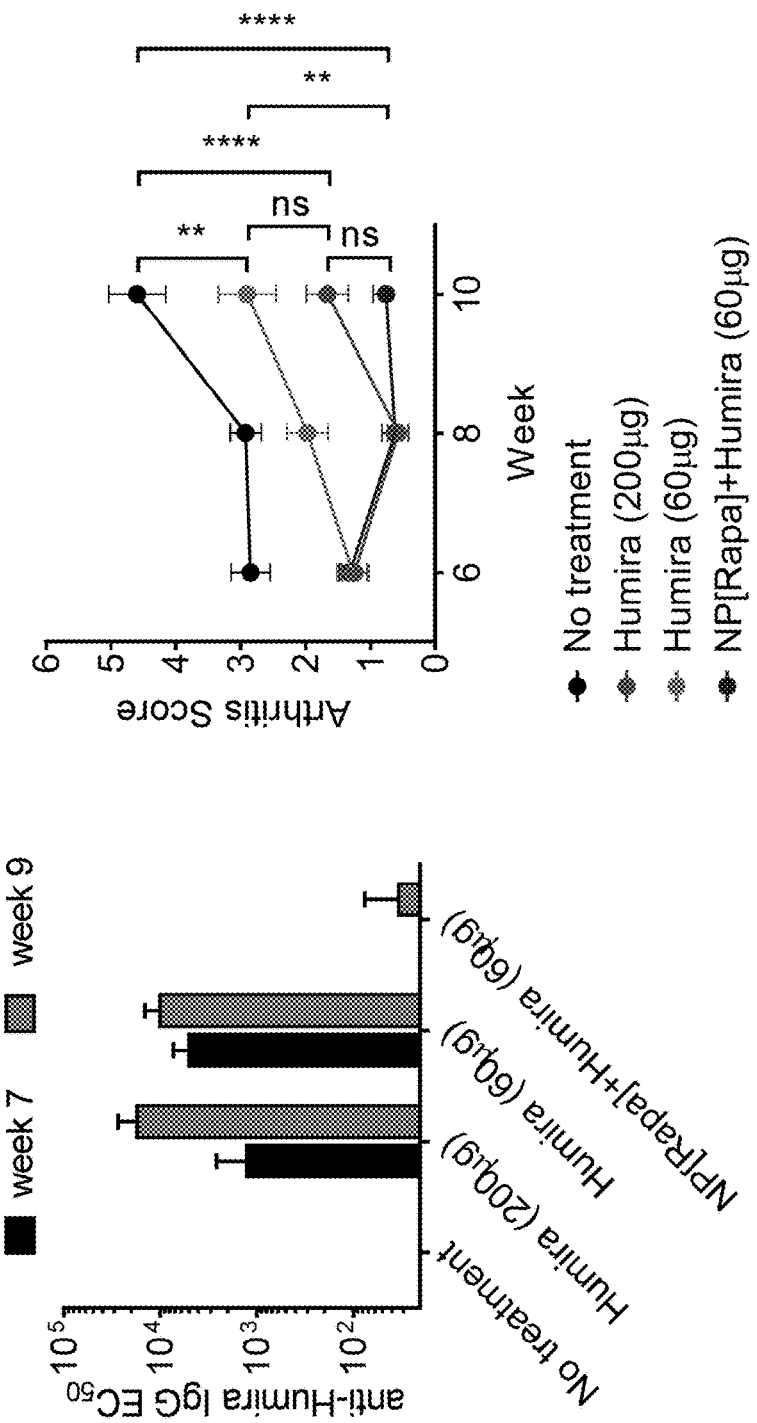
FIG. 17 shows the beneficial effects of practicing a method provided herein in regard to therapy with HUMIRA.

Age-matched HuTNFαTg 5 week old female animals were either injected s.c. in the subscapular area with saline (PBS) or 60 µg or 200 µg of HUMIRA weekly (weeks 5-10) or with a mixture of 60 µg of Humira and 0.87 mg of tolerogenic nanoparticles for the first 3 injections (week 5 to 7 of age) followed by 3 weekly injections of HUMIRA alone (same amounts) (weeks 8 to 10 of age). The results in FIG. 17 (left panel) show the antibody titers in the blood of all animals at different time points. The control mock-treated animals have no titers as expected whereas a robust anti-HUMIRA antibody response can be observed in the animals that received just HUMIRA. Treatment with the nanocarriers from week 5 to 7 of age led to a complete resistance to develop anti-HUMIRA titers even after 3 injections of HUMIRA without the treatment (weeks 8 to 10). Of note, three injections of HUMIRA led to very high titers on the control animals (week 7 titers) while three similar injections (for a total of six) in animals treated with the nanocarriers were totally resistant to develop titers (week 10). FIG. 16 illustrates the dosing regimen.

The monitoring of the limbs of these animals revealed a progressive disease that was already evident at 6 weeks of age. HUMIRA alone had a significant blockade of the disease progression however adding nanocarriers to this regimen dramatically blocked the emergence of arthritic symptoms. The scores (FIG. 17 (right panel)) represent the average total of 4 independent scorers as: 1) represents synovitis, joint effusions and soft tissue swelling 2) includes proliferating inflamed synovial tissue which grows into joint cavity and destroys cartilage 3) shows extensive loss of cartilage, erosion around the margins of joint, and deformities 4) is almost end stage of the disease with fibrous or bony stiffening of joint, which ends it's functional life.

These results show that methods and compositions provided herein can reduce or prevent antibody formation to a therapeutic protein and improve its efficacy. Specifically, as above, these results show that administration of immunosuppressant attached to synthetic nanocarriers with HUMIRA can reduce undesired anti-HUMIRA antibody response. The benefit of the concomitant administration is also evidenced by the further reduced arthritic score which demonstrate improved efficacy of HUMIRA. This demonstrates not only the reduction of undesired immune responses against a therapeutic protein with concomitant administration of immunosuppressant attached to synthetic nanocarriers but also improved efficacy. This also demonstrates that a higher dose of the therapeutic is not needed with the inventive concomitant administration provided herein. Further, based on the level of reduction in the arthritic score with the same dose of HUMIRA, reduced amounts of HUMIRA could also be used that would provide improved efficacy as compared to the amounts of HUMIRA that would be needed without the concomitant administration of immunosuppressant doses as provided herein. It is important to note that the amount of HUMIRA used in this example was 60 μg, much reduced as compared with amounts used in the art of about 200 μg in order to effect maximal inhibition of inflammation by HUMIRA (Binder et al., Arthritis & Rheumatism, Vol. 65 (No. 3), March 2013, pp. 608-617). Finally, the results support that a protocol was established as provided herein.

Example 18: Antigen-Specific Tolerogenic Responses to Chicken Ovalbumin with Encapsulated Rapamycin NP[Rapa] Materials and Methods
Materials Rapamycin was purchased from TSZ CHEM (185 Wilson Street, Framingham, Mass. 01702), product code R1017. PLGA with a lactide:glycolide ratio of 1:1 and an inherent viscosity of 0.24 dL/g was purchased from Lakeshore Biomaterials (756 Tom Martin Drive, Birmingham, Ala. 35211), product code 5050 DLG 2.5A. PLA-PEG-OMe block co-polymer with a methyl ether terminated PEG block of approximately 5,000 Da and an overall inherent viscosity of 0.50 DL/g was purchased from Lakeshore Biomaterials (756 Tom Martin Drive, Birmingham, Ala. 35211), product code 100 DL mPEG 5000 5CE. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027), product code 1.41350. Cellgro phosphate buffered saline 1× (PBS 1×) was purchased from Corning (9345 Discovery Blvd. Manassas, Va. 20109), product code 21-040-CV.

Method

Solutions were Prepared as Follows:
Solution 1: A polymer and rapamycin mixture was prepared by dissolving PLGA at 75 mg per 1 mL, PLA-PEG-Ome at 25 mg per 1 mL, and rapamycin as 12.5 mg per 1 mL in dichloromethane. Solution 2: Polyvinyl alcohol was prepared at 50 mg/mL in 100 mM pH 8 phosphate buffer.

An O/W emulsions was prepared by combining Solution 1 (1.0 mL) and Solution 2 (3.0 mL) in a small glass pressure tube and sonicating at 30% amplitude for 60 seconds using a Branson Digital Sonifier 250. The O/W emulsion was added to an open beaker containing 70 mM pH 8 phosphate buffer solution (60 mL). Three additional, identical O/W emulsions were prepared and added to the same beaker as the first. These were then stirred at room temperature for 2 hours to allow the dichloromethane to evaporate and for the nanocarriers to form. A portion of the nanocarriers was washed by transferring the nanocarrier suspension to centrifuge tubes and centrifuging at 75,600×g and 4° C. for 35 minutes, removing the supernatant, and re-suspending the pellet in PBS 1×. The wash procedure was repeated and then the pellet was re-suspended in PBS 1× to achieve a nanocarrier suspension having a nominal concentration of 10 mg/mL on a polymer basis. An identical formulation was prepared as above in a separate beaker, and combined with the first after the wash step. The mixed nanocarrier solution was then filtered using 1.2 μm PES membrane syringe filters from Pall part number 4656, and stored at −20° C.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 220 | 11.85 |

NP[OVA] Materials and Methods
Materials

Ovalbumin protein, was purchased from Worthington Biochemical Corporation (730 Vassar Avenue, Lakewood, N.J. 08701), product code LS003054). PLGA with 54% lactide and 46% glycolide content and an inherent viscosity of 0.24 dL/g was purchased from Lakeshore Biomaterials (756 Tom Martin Drive, Birmingham, Ala. 35211), product code 5050 DLG 2.5A). PLA-PEG block co-polymer with a methyl ether terminated PEG block of approximately 5,000 Da and Mw of 28,000 Da, inherent viscosity of 0.38 dL/g was purchased from Lakeshore Biomaterials (756 Tom Martin Drive, Birmingham, Ala. 35211), product code 100 DL mPEG 5000 4CE. EMPROVE® Polyvinyl Alcohol 4-88, USP, 85-89% hydrolyzed, viscosity of 3.4-4.6 mPa·s, was purchased from EMD Chemicals Inc. (480 South Democrat Road Gibbstown, N.J. 08027), product code 1.41350.1001. Cellgro Phosphate-buffered saline 1× (PBS 1×) was purchased from Corning (9345 Discovery Blvd. Manassas, Va. 20109), product code 21-040-CV.

Method

Solutions were Prepared as Follows:
Solution 1: Ovalbumin protein @ 50 mg/mL was prepared in 10 mM phosphate buffer pH 8 with 10% by weight sucrose. Solution 2: PLGA was prepared by dissolving PLGA at 100 mg per 1 mL of dichloromethane in the chemical fume hood. Solution 3: PLA-PEG-OMe was prepared by dissolving PLA-PEG-OMe at 100 mg per 1 mL of dichloromethane in the chemical fume hood. Solution 4: Polyvinyl alcohol @ 65 mg/mL in 100 mM phosphate buffer, pH 8.

A primary (W1/O) emulsion was first created by mixing Solutions 1 through 3. Solution 1 (0.2 mL), Solution 2 (0.75 mL), and Solution 3 (0.25 mL) were combined in a small glass pressure tube which was pre-chilled >4 minutes in an ice water bath, and sonicated at 50% amplitude for 40 seconds over an ice bath using a Branson Digital Sonifier 250. A secondary (W1/O/W2) emulsion was then formed by adding Solution 4 (3 mL) to the primary emulsion, vortex mixing to create a milky dispersion, and then sonicating at 30% amplitude for 60 seconds over an ice bath using the Branson Digital Sonifier 250. The secondary emulsion was added to an open 50 mL beaker containing PBS 1× (30 mL). A second identical double emulsion formulation was prepared as described above, and added to the same 50 mL beaker as the first. The two preparations were stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 75,600 rcf for 50 minutes, removing the supernatant, and re-suspending the pellet in PBS 1×. This washing procedure was repeated and then the pellet was re-suspended in PBS 1× to achieve a nanocarrier suspension having a nominal concentration of 10 mg/mL on a polymer basis. The suspension was stored frozen at −20 C until use.

| Effective Diameter (nm) | Ovalbumin Content (% w/w) |
|---|---|
| 164 | 5.81 |

NP[GSK1059615] Materials and Methods
Materials

GSK1059615 was purchased from MedChem Express (11 Deer Park Drive, Suite 102D Monmouth Junction, N.J. 08852), product code HY-12036. PLGA with a lactide:glycolide ratio of 1:1 and an inherent viscosity of 0.24 dL/g was purchased from Lakeshore Biomaterials (756 Tom Martin Drive, Birmingham, Ala. 35211), product code 5050 DLG 2.5A. PLA-PEG-OMe block co-polymer with a methyl ether terminated PEG block of approximately 5,000 Da and an overall inherent viscosity of 0.26 DL/g was purchased from Lakeshore Biomaterials (756 Tom Martin Drive, Birmingham, Ala. 35211; Product Code 100 DL mPEG 5000 5K-E). Cellgro phosphate buffered saline 1× pH 7.4 (PBS 1×) was purchased from Corning (9345 Discovery Blvd. Manassas, Va. 20109), product code 21-040-CV.

Method

Solutions were Prepared as Follows:

Solution 1: PLGA (125 mg), and PLA-PEG-OMe (125 mg), were dissolved in 10 mL of acetone. Solution 2: GSK1059615 was prepared at 10 mg in 1 mL of N-methyl-2-pyrrolidinone (NMP).

Nanocarriers were prepared by combining Solution 1 (4 mL) and Solution 2 (0.25 mL) in a small glass pressure tube and adding the mixture drop wise to a 250 mL round bottom flask containing 20 mL of ultra-pure water under stirring. The flask was mounted onto a rotary evaporation device, and the acetone was removed under reduced pressure. A portion of the nanocarriers was washed by transferring the nanocarrier suspension to centrifuge tubes and centrifuging at 75,600 rcf and 4° C. for 50 minutes, removing the supernatant, and re-suspending the pellet in PBS 1×. The washing procedure was repeated, and the pellet was re-suspended in PBS 1× to achieve a nanocarrier suspension having a nominal concentration of 10 mg/mL on a polymer basis. The washed nanocarrier solution was then filtered using 1.2 μm PES membrane syringe filters from Pall, part number 4656. An identical nanocarrier solution was prepared as above, and pooled with the first after the filtration step. The homogenous suspension was stored frozen at −20° C.

Nanocarrier size was determined by dynamic light scattering. The amount of GSK1059615 in the nanocarrier was determined by UV absorption at 351 nm. The total dry-nanocarrier mass per mL of suspension was determined by a gravimetric method.

| Effective Diameter (nm) | GSK1059615 Content (% w/w) |
|---|---|
| 143 | 1.02 |

C57BL/6 age-matched (5-6 weeks) female mice were injected i.v. in the tail vein on days −21 and −14 with saline (No Treatment), 1.1 mg of whole Ovalbumin-loaded nanocarriers (NP[OVA]) combined to either 1.2 mg of rapamycin-containing nanocarriers (NP[Rapa]) or 8 mg of GSK1059615-loaded nanocarriers (NP[GSK1059615]).

Figure 18:
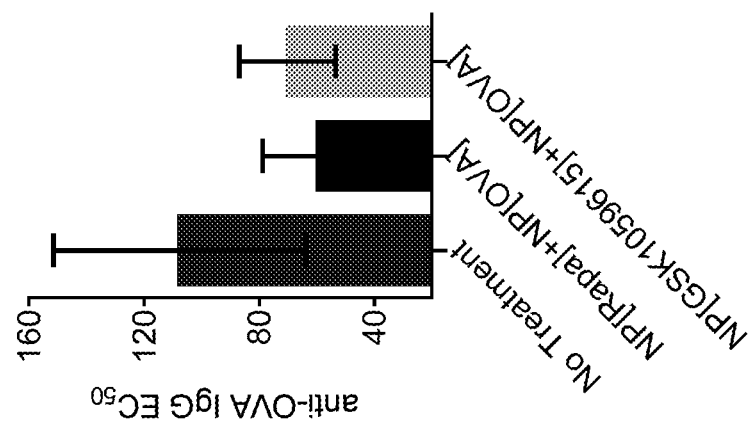
FIG. 18 demonstrates the reduction in anti-protein antibody responses as a result of two different immunosuppressants attached to synthetic nanocarriers.

At day 0 all animals were injected s.c. in the hind limbs with 25 μg of particulate OVA (pOVA) admixed to 2 μg of CpG followed by injections of just 25 μg pOVA on days 7 and 14. Antibody titers were measured on day 21. In absence of any treatment, the animals developed a robust immune response against OVA that can be measured by the anti-OVA IgG antibody titers. The antibody titers at day 21 shown in FIG. 18 demonstrate that 2 doses of synthetic tolerogenic nanocarriers administered concomitantly with encapsulated OVA in the same solution (NP[OVA]+NP[Rapa] or NP[GSK1059615]) were effective in reducing antibody formation to OVA even after 1 injection of OVA+CpG and 2 injections of OVA alone.

These results show that encapsulated immunosuppressants (such as rapamycin and GSK10596151) when concomitantly delivered with a protein can prevent antibody formation to that protein for multiple challenges and periods of time. This demonstrates not only the reduction of undesired immune responses against a protein with concomitant administration of two different kinds of immunosuppressant. Finally, the results support that a protocol was established as provided herein.

Example 19: Inventive Method Using Reduced Pharmacodynamically Effective Dose (Prophetic)

Three thousand two hundred human subjects suffering from rheumatoid arthritis are recruited for a series of clinical trials. In a pilot dose ranging trial, 1,200 subjects are divided into four arms (placebo and 3 different dose levels of synthetic nanocarriers of Example 3). Each subject in each of the four arms receives two rounds of HUMIRA 40 mg s.c. concomitantly with either placebo or synthetic nanocarrier. The synthetic nanocarrier dose that most reduces the mean level of anti-HUMIRA antibodies in an arm is declared to be the “Immunosuppressant Dose” for the trial.

In another pilot trial, the recruited human subjects are divided into 4 Test Arms of 500 subjects each. Placebo, HUMIRA, and synthetic nanocarriers of Example 3 are administered concomitantly (except for Test Arm 1) according to the following table, with the synthetic nanocarriers being administered at the Immunosuppressant Dose.

| Test Arm Number | HUMIRA dose | NC Admin (sc) |
|---|---|---|
| 1 | 40 mg sc | − |
| 2 | 40 mg sc | + |
| 3 | 20 mg sc | + |
| 4 | 10 mg sc | + |
| 5 | Placebo | Placebo |

The target pharmacodynamic effects (“PD effect”) are evaluated, which in this case are the means of ACR 20, 50 and 70 responses for the subjects in each Test Arm. The PD effect for subjects in Test Arm 1 is noted, and the HUMIRA dose in Test Arm 1 is arbitrarily defined as the pharmacodynamically effective dose (“PD Effective Dose”) of HUMIRA.

The PD effect for Test Arms 2-4 are then evaluated, and the lowest dose at which the PD effect is not significantly different from the Test Arm 1 PD effect is declared to be the reduced pharmacodynamically effective dose of HUMIRA.

In an application of the information established during the pilot trials, a reduced pharmacodynamically effective dose of HUMIRA is administered concomitantly with the Immunosuppressant Dose (containing synthetic nanocarriers of Example 3) to subjects diagnosed with rheumatoid arthritis and at risk of developing antibodies to HUMIRA. In a further embodiment, a protocol using the information established during the pilot trials is prepared to guide concomitant dosing of Humira™ and synthetic nanocarriers of Example 3 to human subjects diagnosed with rheumatoid arthritis and have or are expected to have antibodies to HUMIRA. This protocol is then used to guide concomitant administration of a reduced pharmacodynamically effective dose of HUMIRA, and synthetic nanocarriers of Example 3, to human subjects.

Example 20: Inventive Method Demonstrating Enhanced Pharmacodynamic Effect (Prophetic)

Three thousand seven hundred human subjects suffering from rheumatoid arthritis are recruited for a series of clinical trials. In a pilot dose ranging trial, 1,200 subjects are divided into four arms (placebo and 3 different dose levels of synthetic nanocarriers of Example 3). Each subject in each of the four arms receives two rounds of HUMIRA 40 mg s.c. concomitantly with either placebo or synthetic nanocarrier. The synthetic nanocarrier dose that most reduces the mean level of anti-HUMIRA antibodies in an arm is declared to be the "Immunosuppressant Dose" for the trial.

In another pilot trial, the recruited human subjects are divided into 3 Test Arms, with two active Test Arms having 1000 subjects each, and one placebo arm of 500 subjects. Placebo, HUMIRA, and synthetic nanocarriers of Example 3 are administered concomitantly (except for Test Arm 1) according to the following table, with the synthetic nanocarriers being administered at the Immunosuppressant Dose.

| Test Arm Number | HUMIRA dose | NC Admin (sc) |
|---|---|---|
| 1 | 40 mg sc | – |
| 2 | 40 mg sc | + |
| 3 | Placebo | Placebo |

The target pharmacodynamic effects ("PD effect") are evaluated, which in this case are the means of ACR 20, 50 and 70 responses for the subjects in each Test Arm. The PD effect for subjects in Test Arm 1 is noted and compared to the PD effect in Test Arm 2. Any enhancement of the pharmacodynamic effect of HUMIRA upon concomitant administration with the Immunosuppressant Dose in Test Arm 2 is noted, as compared with the PD effect observed in Test Arm 1.

In an application of the information established during the pilot trials, the standard 40 mg dose of HUMIRA is administered concomitantly with the Immunosuppressant Dose (containing synthetic nanocarriers of Example 3) to subjects diagnosed with rheumatoid arthritis and at risk of developing antibodies to HUMIRA. In a further embodiment, a protocol using the information established during the pilot trials is prepared to guide concomitant dosing of HUMIRA and synthetic nanocarriers of Example 3 to human subjects diagnosed with rheumatoid arthritis and known or believed to have antibodies to HUMIRA. This protocol is then used to guide concomitant administration of HUMIRA, and synthetic nanocarriers of Example 3, to human subjects. Any enhanced pharmacodynamic effect following the concomitant administration is recorded using the approaches disclosed herein.

Example 21: Inventive Method Demonstrating Enhanced Pharmacodynamic Effect (Prophetic)

Three thousand two hundred human subjects suffering from chemotherapy-related anemia are recruited for a series of clinical trials. In a pilot dose ranging trial, modified mRNA encoding erythropoietin is prepared according to U.S. Patent application 2013/0115272 to de Fougerolles et al. ("mmRNA"). Twelve hundred subjects are divided into four arms (placebo and 3 different dose levels of synthetic nanocarriers of Example 3). Each subject in each of the four arms receives a therapeutic dose of mmRNA concomitantly with either placebo or synthetic nanocarrier. The synthetic nanocarrier dose that most reduces the mean level of anti-mmRNA antibodies in an arm is declared to be the "Immunosuppressant Dose" for the trial.

In another pilot trial, the recruited human subjects are divided into 4 Test Arms of 500 subjects each. Placebo, mmRNA, and synthetic nanocarriers of Example 3 are administered concomitantly (except for Test Arm 1) according to the following table, with the synthetic nanocarriers being administered at the Immunosuppressant Dose.

| Test Arm Number | mmRNA dose | NC Admin (sc) |
|---|---|---|
| 1 | Therapeutic dose sc | – |
| 2 | Therapeutic dose sc | + |
| 3 | ½ Therapeutic dose sc | + |
| 4 | ¼ Therapeutic dose sc | + |
| 5 | Placebo | Placebo |

The target pharmacodynamic effects ("PD effect") are evaluated, which in this case are the means of chemotherapy-induced anemia responses for the subjects in each Test Arm. The PD effect for subjects in Test Arm 1 is noted, and the mmRNA dose in Test Arm 1 is arbitrarily defined as the pharmacodynamically effective dose ("PD Effective Dose") of mmRNA. The PD effect for Test Arms 2-4 are then evaluated, and the lowest dose at which the PD effect is not significantly different from the Test Arm 1 PD effect is declared to be the reduced pharmacodynamically effective dose of mmRNA. In an application of the information established during the pilot trials, a reduced pharmacodynamically effective dose of mmRNA is administered concomitantly with the Immunosuppressant Dose (containing synthetic nanocarriers of Example 3) to subjects diagnosed with chemotherapy-related anemia and at risk of developing antibodies to mmRNA.

In a further embodiment, a protocol using the information established during the pilot trials is prepared to guide concomitant dosing of mmRNA and synthetic nanocarriers of Example 3 to human subjects diagnosed with chemotherapy-related anemia and known or believed to have antibodies to mmRNA. This protocol is then used to guide concomitant administration of a reduced pharmacodynamically effective dose of mmRNA, and synthetic nanocarriers of Example 3, to human subjects.

Example 22: Method to Maintain Efficacy of a Biologic Drug During a Period of Multidosing Biologic drugs often lose activity over time after multiple doses. A common cause of loss of efficacy is the formation of ADAs. ADAs can cause loss of drug efficacy, for example by 1) enhancing clearance of the drug, such that the PK of the drug after multiple doses is substantially less than the PK of the drug after a single dose or by 2) neutralizing the activity of the drug, such that the biological activity of the drug after multiple doses is substantially less than the biological activity after a single dose. It would be desirable to maintain activity of the biologic drug over the course of multiple dosing.

Transgenic mice expressing human TNF-α spontaneously develop arthritis over a period of 5-20 weeks of age. Mice were treated weekly with HUMIRA (60 μg/injection) with or without synthetic nanocarriers from Example 16 from weeks 5-11. Panel B (FIG. 19) shows the serum levels of HUMIRA after the first dose (Day 1). After 6 doses of HUMIRA, the blood levels of HUMIRA are close to baseline in mice treated with HUMIRA alone and remain low through week 20 (Panel C, FIG. 19, black squares). In contrast, mice treated with HUMIRA and the synthetic nanocarriers show serum levels of HUMIRA (panel C, FIG. 19, blue triangles) that are similar to that after the first dose, indicating that synthetic nanocarrier treatment enabled effective blood levels of HUMIRA to be maintained after multiple dosing.

Figure 19:
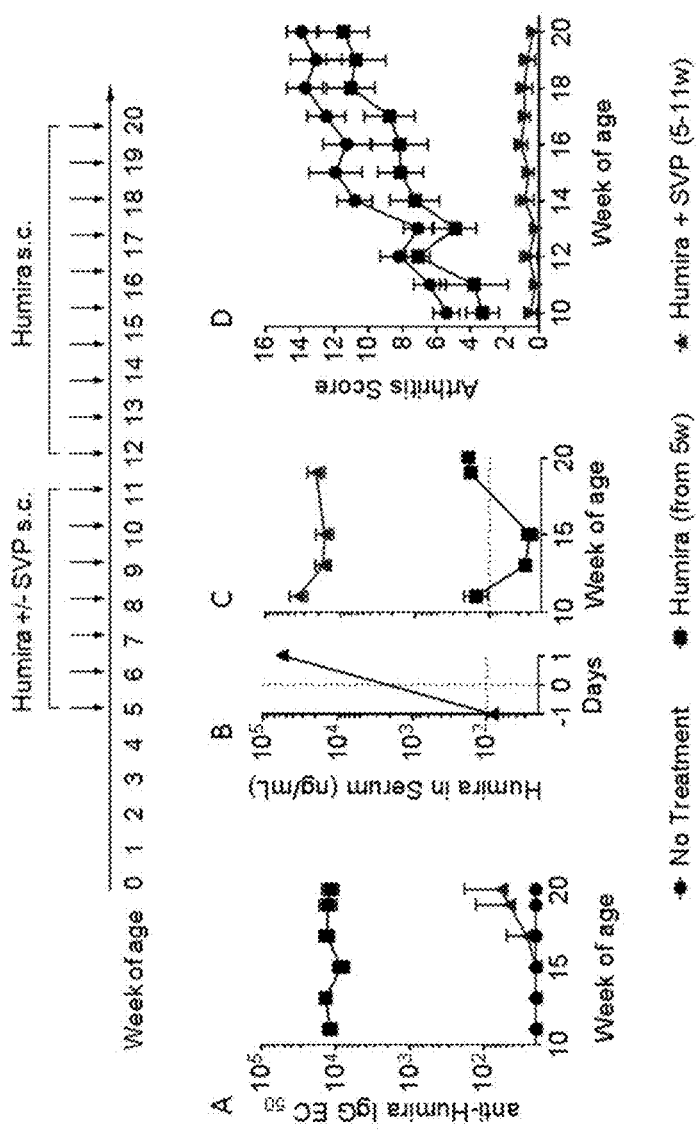
FIG. 19 shows another exemplary protocol and the beneficial effects of practicing a method provided herein in regard to therapy with HUMIRA.

The reduction in serum HUMIRA blood levels in mice treated with HUMIRA alone can be attributed to the development of ADAs. By week 11, mice treated with HUMIRA alone developed high titer anti-drug antibodies (Panel A, FIG. 19, black square symbols). In contrast mice treated with the synthetic nanocarriers show little or no anti-HUMIRA antibody response (Panel A, FIG. 19, blue triangles). The impact of the reduction of HUMIRA serum levels with multiple dosing is apparent in the arthritis disease scores as above in Example 16 (Panel D, FIG. 19). Mice treated with HUMIRA alone show suboptimal attenuation of arthritis scores from week 10-20 (Panel D, FIG. 19, compare black squares to black circles). In contrast, mice treated with synthetic nanocarriers show strong inhibition of arthritis (Panel C, FIG. 19, blue triangles).

These results indicate that maintenance of drug levels with multiple dosing is important for drug efficacy, and that the immunosuppressants attached to synthetic nanocarriers maintain drug levels with multiple dosing by inhibiting the ADA response. Accordingly, these results demonstrate the benefits of repeatedly dosing therapeutic macromolecules concomitantly with immunosuppressants as provided herein. The results further demonstrate the ability to determine protocols that can accomplish the desired therapeutic effects and/or reduced ADA responses in subjects.

Example 23: Inventive Method Demonstrating Enhanced Pharmacodynamic Effect (Prophetic)

Three thousand seven hundred human subjects suffering from rheumatoid arthritis are recruited for a series of clinical trials. In a pilot dose ranging trial, 1,200 subjects are divided into four arms (placebo and 3 different dose levels of nanocrystalline rapamycin). Each subject in each of the four arms receives two rounds of HUMIRA 40 mg s.c. concomitantly with either placebo or nanocrystalline rapamycin. The nanocrystalline rapamycin dose that most reduces the mean level of anti-HUMIRA antibodies in an arm is declared to be the "Immunosuppressant Dose" for the trial.

In another pilot trial, the recruited human subjects are divided into 3 Test Arms, with two active Test Arms having 1000 subjects each, and one placebo arm of 500 subjects. Placebo, HUMIRA, and nanocrystalline rapamycin are administered concomitantly (except for Test Arm 1) according to the following table, with the synthetic nanocarriers being administered at the Immunosuppressant Dose.

| Test Arm Number | HUMIRA dose | Immunosuppressant dose (sc) |
|---|---|---|
| 1 | 40 mg sc | – |
| 2 | 40 mg sc | + |
| 3 | Placebo | Placebo |

The target pharmacodynamic effects ("PD effect") are evaluated, which in this case are the means of ACR 20, 50 and 70 responses for the subjects in each Test Arm. The PD effect for subjects in Test Arm 1 is noted and compared to the PD effect in Test Arm 2. Any enhancement of the pharmacodynamic effect of HUMIRA upon concomitant administration with the Immunosuppressant Dose in Test Arm 2 is noted, as compared with the PD effect observed in Test Arm 1.

In an application of the information established during the pilot trials, the standard 40 mg dose of HUMIRA is administered concomitantly with the Immunosuppressant Dose (containing nanocrystalline rapamycin) to subjects diagnosed with rheumatoid arthritis and at risk of developing antibodies to HUMIRA. In a further embodiment, a protocol using the information established during the pilot trials is prepared to guide concomitant dosing of HUMIRA and nanocrystalline rapamycin to human subjects diagnosed with rheumatoid arthritis and known or believed to have antibodies to HUMIRA. This protocol is then used to guide concomitant administration of HUMIRA and nanocrystalline rapamycin, to human subjects. Any enhanced pharmacodynamic effect following the concomitant administration is recorded using the approaches disclosed herein.

Example 24: Inventive Method Demonstrating Enhanced Pharmacodynamic Effect (Prophetic)

Three thousand two hundred human subjects suffering from chemotherapy-related anemia are recruited for a series of clinical trials. In a pilot dose ranging trial, modified mRNA encoding erythropoietin is prepared according to U.S. Patent application 2013/0115272 to de Fougerolles et al. ("mmRNA"). Twelve hundred subjects are divided into four arms (placebo and 3 different dose levels of nanocrystalline rapamycin). Each subject in each of the four arms receives a therapeutic dose of mmRNA concomitantly with either placebo or nanocrystalline rapamycin. The nanocrystalline rapamycin dose that most reduces the mean level of anti-mmRNA antibodies in an arm is declared to be the "Immunosuppressant Dose" for the trial.

In another pilot trial, the recruited human subjects are divided into 4 Test Arms of 500 subjects each. Placebo, mmRNA, and synthetic nanocarriers of Example 3 are administered concomitantly (except for Test Arm 1) according to the following table, with the nanocrystalline rapamycin being administered at the Immunosuppressant Dose.

| Test Arm Number | mmRNA dose | Nanocrystalline rapamycin (sc) |
|---|---|---|
| 1 | Therapeutic dose sc | – |
| 2 | Therapeutic dose sc | + |
| 3 | ½ Therapeutic dose sc | + |
| 4 | ¼ Therapeutic dose sc | + |
| 5 | Placebo | Placebo |

The target pharmacodynamic effects ("PD effect") are evaluated, which in this case are the means of chemotherapy-induced anemia responses for the subjects in each Test Arm. The PD effect for subjects in Test Arm 1 is noted, and the mmRNA dose in Test Arm 1 is arbitrarily defined as the pharmacodynamically effective dose ("PD Effective Dose") of mmRNA. The PD effect for Test Arms 2-4 are then evaluated, and the lowest dose at which the PD effect is not significantly different from the Test Arm 1 PD effect is declared to be the reduced pharmacodynamically effective dose of mmRNA. In an application of the information established during the pilot trials, a reduced pharmacodynamically effective dose of mmRNA is administered concomitantly with the Immunosuppressant Dose (containing nanocrystalline rapamycin) to subjects diagnosed with chemotherapy-related anemia and at risk of developing antibodies to mmRNA.

In a further embodiment, a protocol using the information established during the pilot trials is prepared to guide concomitant dosing of mmRNA and nanocrystalline rapamycin to human subjects diagnosed with chemotherapy-related anemia and known or believed to have antibodies to mmRNA. This protocol is then used to guide concomitant administration of a reduced pharmacodynamically effective dose of mmRNA and nanocrystalline rapamycin, to human subjects.

What is claimed is:

1. A method comprising:
   (i) providing an immunosuppressant dose, wherein the immunosuppressant dose is attached to synthetic nanocarriers; and
   administering a reduced pharmacodynamically effective dose of a therapeutic macromolecule concomitantly with the immunosuppressant dose to a subject in which an anti-therapeutic macromolecule antibody response is expected to occur;
   wherein the concomitant administration is according to a protocol that has been demonstrated to result in a pharmacodynamic effect with the reduced pharmacodynamically effective dose of the therapeutic macromolecule upon concomitant administration with the immunosuppressant dose, as compared to administration of the therapeutic macromolecule when not administered concomitantly with the immunosuppressant dose and in the presence of an anti-therapeutic macromolecule antibody response.

2. The method of claim 1, wherein the method further comprises determining the protocol.

3. The method of claim 1, wherein the method further comprises determining the reduced pharmacodynamically effective dose.

4. The method of claim 1, wherein the method further comprises assessing the pharmacodynamic effect in the subject prior to and/or after the administration.

5. A method comprising:
   (i) providing an immunosuppressant dose, wherein the immunosuppressant dose is attached to synthetic nanocarriers; and
   administering a pharmacodynamically effective dose of a therapeutic macromolecule concomitantly with the immunosuppressant dose to a subject in which an anti-therapeutic macromolecule antibody response is expected to occur;
   wherein the concomitant administration is according to a protocol that has been demonstrated to enhance a pharmacodynamic effect of the therapeutic macromolecule upon concomitant administration with the immunosuppressant dose, as compared to administration of the therapeutic macromolecule when not administered concomitantly with the immunosuppressant dose, and each in the presence of an anti-therapeutic macromolecule antibody response.

6. The method of claim 5, wherein the method further comprises determining the protocol.

7. The method of claim 5, wherein the method further comprises determining the pharmacodynamically effective dose.

8. The method of claim 5, wherein the method further comprises assessing the pharmacodynamic effect in the subject prior to and/or after the administration.

9. The method of claim 1, wherein the therapeutic macromolecule is not attached to the synthetic nanocarriers.

10. The method of claim 1, wherein the therapeutic macromolecule is attached to the synthetic nanocarriers.

11. The method of claim 1, wherein the reduced pharmacodynamically effective dose of the therapeutic macromolecule is at least 30% less than a pharmacodynamically effective dose of the therapeutic macromolecule that: (A) is administered in the presence of an anti-therapeutic macromolecule antibody response, and (B) is not administered concomitantly with the immunosuppressant dose.

12. The method of claim 1, wherein the immunosuppressant dose comprises a statin, an mTOR inhibitor, a TGF-β signaling agent, a corticosteroid, an inhibitor of mitochondrial function, a P38 inhibitor, an NF-Kκβ inhibitor, an adenosine receptor agonist, a prostaglandin E2 agonist, a phosphodiesterase 4 inhibitor, an HDAC inhibitor or a proteasome inhibitor.

13. The method of claim 1, wherein the therapeutic macromolecule comprises a therapeutic protein.

14. The method of claim 13, wherein the therapeutic protein is for protein replacement or protein supplementation therapy.

15. The method of claim 1, wherein the therapeutic macromolecule comprises a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease.

16. The method of claim 1, wherein a load of immunosuppressant attached to the synthetic nanocarriers, on average across the synthetic nanocarriers, is between 0.1% and 50%.

17. The method of claim 1, wherein the synthetic nanocarriers comprise lipid nanoparticles, polymeric nanoparticles, metallic nanoparticles, surfactant-based emulsions, dendrimers, buckyballs, nanowires, virus-like particles or peptide or protein particles.

18. The method of claim 1, wherein the mean of a particle size distribution obtained using dynamic light scattering of the synthetic nanocarriers is a diameter greater than 100 nm.

19. The method of claim 1, wherein an aspect ratio of the synthetic nanocarriers is greater than 1:1, 1:1.2, 1:1.5, 1:2, 1:3, 1:5, 1:7 or 1:10.

20. A method comprising:
   providing an immunosuppressant dose, wherein the immunosuppressant dose is attached to synthetic nanocarriers; and
   administering a reduced pharmacodynamically effective dose of a therapeutic macromolecule concomitantly with the immunosuppressant dose;
   wherein the reduced pharmacodynamically effective dose of the therapeutic macromolecule is less than a pharmacodynamically effective dose of the therapeutic macromolecule that: (A) is administered in the presence of an anti-therapeutic macromolecule antibody response, and (B) is not administered concomitantly with the immunosuppressant dose.

21. A method comprising:
   providing an immunosuppressant dose, wherein the immunosuppressant dose is attached to synthetic nanocarriers;
   administering a pharmacodynamically effective dose of a therapeutic macromolecule concomitantly with the immunosuppressant dose to a subject in which an anti-therapeutic macromolecule antibody response is expected to occur; and
   recording an enhanced pharmacodynamic effect following the concomitant administration.

22. A method comprising:
   providing therapeutic macromolecules that cause or are expected to cause anti-therapeutic macromolecule antibodies upon repeated dosing in one or more subjects;
   providing an immunosuppressant dose, wherein the immunosuppressant dose is attached to synthetic nanocarriers; and
   repeatedly dosing at the same or a lower dose a subject with the therapeutic macromolecules concomitantly with the immunosuppressant dose.

* * * * *